(12) United States Patent
Han et al.

(10) Patent No.: US 10,752,884 B2
(45) Date of Patent: Aug. 25, 2020

(54) METHOD OF INDUCING BETA CELLS FROM URINE-DERIVED CELLS USING SMALL MOLECULES

(71) Applicant: UNIVERSITY OF SOUTH AUSTRALIA, Adelaide (AU)

(72) Inventors: Yanchuang Han, Hallett Cove (AU); Xin-Fu Zhou, Hallett Cove (AU); WooKyung Kim, Incheon (KR); JunYong Yang, Incheon (KR); JiHee Kim, Incheon (KR)

(73) Assignee: University of South Australia (AU)

( * ) Notice: Subject to any disclaimer, the term of this patent is extended or adjusted under 35 U.S.C. 154(b) by 0 days.

(21) Appl. No.: 15/538,465

(22) PCT Filed: Dec. 22, 2015

(86) PCT No.: PCT/AU2015/000760
§ 371 (c)(1),
(2) Date: Jun. 21, 2017

(87) PCT Pub. No.: WO2016/101010
PCT Pub. Date: Jun. 30, 2016

(65) Prior Publication Data
US 2018/0016556 A1    Jan. 18, 2018

(30) Foreign Application Priority Data

Dec. 22, 2014  (AU) ................................ 2014905202

(51) Int. Cl.
*C12N 5/071*        (2010.01)
(52) U.S. Cl.
CPC ........ *C12N 5/0676* (2013.01); *C12N 2500/38* (2013.01); *C12N 2501/16* (2013.01); *C12N 2501/385* (2013.01); *C12N 2501/724* (2013.01); *C12N 2506/25* (2013.01)
(58) Field of Classification Search
CPC ............ C12N 5/0676; C12N 2501/724; C12N 2500/38; C12N 2501/16; C12N 2501/385; C12N 2506/25
See application file for complete search history.

(56) References Cited

U.S. PATENT DOCUMENTS

2016/0272944 A1* 9/2016 Ding ..................... C12N 5/0696

FOREIGN PATENT DOCUMENTS

| WO | WO 2011/081222 | | 7/2011 |
| WO | WO 2012/089669 A1 | | 7/2012 |
| WO | WO 2013/086570 | | 6/2013 |

OTHER PUBLICATIONS

Zhang et al. Urine-derived stem cells: A novel and versatile progenitor source for cell-based therapy and regenerative medicine. Genes & Diseases (2014) 1, 8-17 (Year: 2014).*
Esteban et al. Vitamin C Enhances the Generation of Mouse and Human Induced Pluripotent Stem Cells. Cell Stem Cell 6, 71-79, Jan. 8, 2010 (Year: 2010).*
Cao et al. Ascorbic acid enhances the cardiac differentiation of induced pluripotent stem cells through promoting the proliferation of cardiac progenitor cells. Cell Research (2012) 22:219-236. (Year: 2012).*
Hosoya et al. Preparation of pancreatic β-cells from human iPS cells with small molecules. Islets 4:3, 249-252; May/Jun. 2012 (Year: 2012).*
Yuan et al. A small-molecule inducer of PDX1 expression identified by highthroughput screening. Chem Biol. Dec. 19, 2013; 20(12): 1513-1522. (Year: 2013).*
Hoveizi et al. Definitive endoderm differentiation of human-induced pluripotent stem cells using signaling molecules and IDE1 in three-dimensional polymer scaffold. J Biomed Mater Res Part A: 102A: 4027-4036, 2014. (Year: 2014).*
Li et al. Advances in understanding the cell types and approaches used for generating induced pluripotent stem cells. Journal of Hematology & Oncology 2014, 7:50; p. 1-18 (Year: 2014).*
Zhou et al. Generation of Induced Pluripotent Stem Cells from Urine. J Am Soc Nephrol 22: 1221-1228, 2011. (Year: 2011).*
Efe et al. The evolving biology of small molecules: controlling cell fate and identity. Phil. Trans. R. Soc. B (2011) 366, 2208-2221 (Year: 2011).*
Borowiak et al. Small Molecules Efficiently Direct Endodermal Differentiation of Mouse and Human Embryonic Stem Cells. Cell Stem Cell 4, 348-358, Apr. 3, 2009 (Year: 2009).*
Kumar et al. Recent Developments in (3-Cell Differentiation of Pluripotent Stem Cells Induced by Small and Large Molecules. Int. J. Mol. Sci. 2014, 15, 23418-23447 (Year: 2014).*
Ringsrud. Cells in the Urine Sediment. CE update. laboratory medicine. No. 3, vol. 32. p. 153-155 (Year: 2001).*
International Search Report and Written Opinion prepared by the Australian Patent Office dated Feb. 22, 2016, for International Application No. PCT/AU2015/000760.

(Continued)

*Primary Examiner* — Taeyoon Kim
(74) *Attorney, Agent, or Firm* — Sheridan Ross P.C.

(57) ABSTRACT

The disclosure relates to a method of producing induced beta cells from urine-derived cells, the method comprising providing urine-derived cells; inducing the urine-derived cells by culturing said urine-derived cells in a primary induction culture medium comprising an effective amount of at least one small molecule reprogramming factor(s) for a first period of time to obtain induced endoderm cells; inducing the induced endoderm cells by culturing said induced endoderm cells in a secondary induction culture medium comprising an effective amount of at least one small molecule reprogramming factor(s) for a second period of time to obtain induced pancreatic precursor cells; and inducing the induced pancreatic precursor cells by culturing said pancreatic precursor cells in a tertiary induction culture medium comprising an effective amount of at least one small molecule reprogramming factor(s) for a third period of time to obtain induced beta cells.

11 Claims, 16 Drawing Sheets
Specification includes a Sequence Listing.

(56) References Cited

OTHER PUBLICATIONS

Pagliuca, F.W. et al., "Generation of Functional Human Pancreatic β Cells In Vitro", Cell, 2014, vol. 159, pp. 428-439.

Li, K. et al., "Small Molecules Facilitate the Reprogramming of Mouse Fibroblasts into Pancreatic Lineages", Cell Stem Cell, Feb. 2014, vol. 14, pp. 228-236.

Tateishi, K. et al., "Generation of Insulin-secreting Islet-like Clusters from Human Skin Fibroblasts", The Journal of Biological Chemistry, 2008, vol. 283, No. 46, pp. 31601-31607.

Bharadwaj, S. et al., "Characterization of Urine-Derived Stem Cells Obtained from Upper Urinary Tract for Use in Cell-Based Urological Tissue Engineering"; Tissue Engineering: Part A, vol. 17, Nos. 15 and 16, 2011, pp. 2123-2132.

Lang, R. et al., "Self-Renewal and Differentiation Capacity of Urine-Derived Stem Cells after Urine Preservation for 24 Hours"; PLOS ONE, Jan. 2013, vol. 8, Issue 1, e53980, pp. 1-11.

Zhou, T. et al., "Generation of Induced Pluripotent Stem Cells from Urine," J Am Soc Nephrol 22; pp. 1221-1228, 2011.

Bharadwaj et al. "Multipotential Differentiation of Human Urine-Derived Stem Cells: Potential for Therapeutic Applications in Urology," Stem Cells, 2013, vol. 31, pp. 1840-1856.

Takahashi et al. "Generation of pancreatic beta-cells from pluripotent stem cells," Organ Biology, 2014, vol. 21, No. 2, 9 pages (English abstract).

Official Action with English Translation for Japan Patent Application No. 2017-533549, dated Sep. 26, 2019, 8 pages.

\* cited by examiner

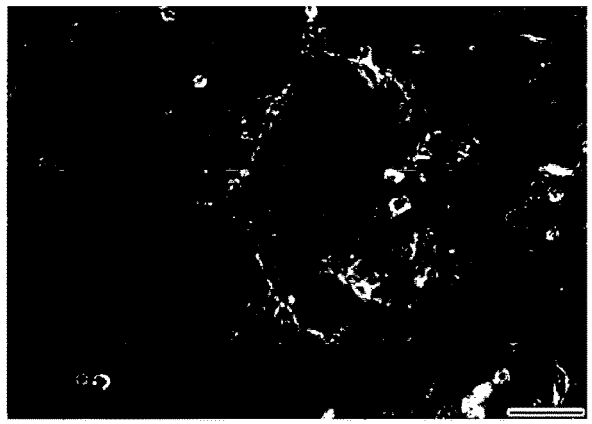 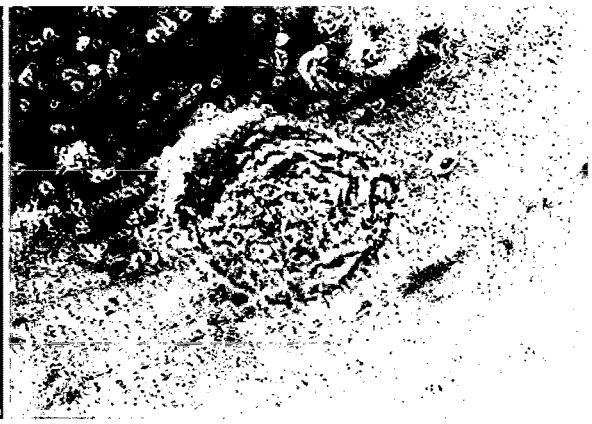
FIGURE 5A  FIGURE 5B
 
FIGURE 6A  FIGURE 6B

SEQUENCE LISTING

```
<160> NUMBER OF SEQ ID NOS: 75

<210> SEQ ID NO 1
<211> LENGTH: 21
<212> TYPE: DNA
<213> ORGANISM: Homo sapiens

<400> SEQUENCE: 1
gctttcatgg tgtgggctaa g                                                 21

<210> SEQ ID NO 2
<211> LENGTH: 19
<212> TYPE: DNA
<213> ORGANISM: Homo sapiens

<400> SEQUENCE: 2
cgacttgccc agcatcttg                                                    19

<210> SEQ ID NO 3
<211> LENGTH: 25
<212> TYPE: DNA
<213> ORGANISM: Homo sapiens

<400> SEQUENCE: 3
agcagaatcc agacctgcac aacgc                                             25

<210> SEQ ID NO 4
<211> LENGTH: 18
<212> TYPE: DNA
<213> ORGANISM: Homo sapiens

<400> SEQUENCE: 4
cgggcgagtt aaagtatg                                                     18

<210> SEQ ID NO 5
<211> LENGTH: 18
<212> TYPE: DNA
<213> ORGANISM: Homo sapiens

<400> SEQUENCE: 5
tctgcatagt agctgctc                                                     18

<210> SEQ ID NO 6
<211> LENGTH: 20
<212> TYPE: DNA
<213> ORGANISM: Homo sapiens

<400> SEQUENCE: 6
ccttccatct tcaccgctcc                                                   20

<210> SEQ ID NO 7
<211> LENGTH: 19
<212> TYPE: DNA
<213> ORGANISM: Homo sapiens

<400> SEQUENCE: 7
cagcgttgga acagaggtt                                                    19
```

```
<210> SEQ ID NO 8
<211> LENGTH: 19
<212> TYPE: DNA
<213> ORGANISM: Homo sapiens

<400> SEQUENCE: 8
ctctgtaggc cctgtttct                                                    19

<210> SEQ ID NO 9
<211> LENGTH: 20
<212> TYPE: DNA
<213> ORGANISM: Homo sapiens

<400> SEQUENCE: 9
tccacagcca gctggaactt                                                   20

<210> SEQ ID NO 10
<211> LENGTH: 18
<212> TYPE: DNA
<213> ORGANISM: Homo sapiens

<400> SEQUENCE: 10
ggttgtgttc cagtttca                                                     18

<210> SEQ ID NO 11
<211> LENGTH: 19
<212> TYPE: DNA
<213> ORGANISM: Homo sapiens

<400> SEQUENCE: 11
gacagcttgg agatgataa                                                    19

<210> SEQ ID NO 12
<211> LENGTH: 26
<212> TYPE: DNA
<213> ORGANISM: Homo sapiens

<400> SEQUENCE: 12
cttatcctgc ctggtattgt catcct                                            26

<210> SEQ ID NO 13
<211> LENGTH: 21
<212> TYPE: DNA
<213> ORGANISM: Homo sapiens

<400> SEQUENCE: 13
tgctagagct ggagaaggag t                                                 21

<210> SEQ ID NO 14
<211> LENGTH: 20
<212> TYPE: DNA
<213> ORGANISM: Homo sapiens

<400> SEQUENCE: 14
tcttgatgtg tctctcggtc                                                   20

<210> SEQ ID NO 15
<211> LENGTH: 28
<212> TYPE: DNA
<213> ORGANISM: Homo sapiens

<400> SEQUENCE: 15
ctattcaaca agtacatctc acggccgc                                          28
```

<210> SEQ ID NO 16
<211> LENGTH: 19
<212> TYPE: DNA
<213> ORGANISM: Homo sapiens

<400> SEQUENCE: 16
aagagcgagt tggcactga                                                  19

<210> SEQ ID NO 17
<211> LENGTH: 20
<212> TYPE: DNA
<213> ORGANISM: Homo sapiens

<400> SEQUENCE: 17
gatgtagttg tgggcgaagc                                                 20

<210> SEQ ID NO 18
<211> LENGTH: 26
<212> TYPE: DNA
<213> ORGANISM: Homo sapiens

<400> SEQUENCE: 18
caatcgaatg cacaacctca actcgg                                          26

<210> SEQ ID NO 19
<211> LENGTH: 18
<212> TYPE: DNA
<213> ORGANISM: Homo sapiens

<400> SEQUENCE: 19
ggacaaagac aagaggaa                                                   18

<210> SEQ ID NO 20
<211> LENGTH: 18
<212> TYPE: DNA
<213> ORGANISM: Homo sapiens

<400> SEQUENCE: 20
cctcatagct tgaccttc                                                   18

<210> SEQ ID NO 21
<211> LENGTH: 20
<212> TYPE: DNA
<213> ORGANISM: Homo sapiens

<400> SEQUENCE: 21
cgctcattct ggacggcttc                                                 20

<210> SEQ ID NO 22
<211> LENGTH: 18
<212> TYPE: DNA
<213> ORGANISM: Homo sapiens

<400> SEQUENCE: 22
ggcaagacaa atgatgag                                                   18

<210> SEQ ID NO 23
<211> LENGTH: 19
<212> TYPE: DNA
<213> ORGANISM: Homo sapiens

<400> SEQUENCE: 23
catggtagaa cagatgaga 19

<210> SEQ ID NO 24
<211> LENGTH: 21
<212> TYPE: DNA
<213> ORGANISM: Homo sapiens

<400> SEQUENCE: 24
agatgtccgc tcaatggctc a 21

<210> SEQ ID NO 25
<211> LENGTH: 18
<212> TYPE: DNA
<213> ORGANISM: Homo sapiens

<400> SEQUENCE: 25
cttccctttt aagcaagg 18

<210> SEQ ID NO 26
<211> LENGTH: 18
<212> TYPE: DNA
<213> ORGANISM: Homo sapiens

<400> SEQUENCE: 26
ccagagttca agtttcag 18

<210> SEQ ID NO 27
<211> LENGTH: 20
<212> TYPE: DNA
<213> ORGANISM: Homo sapiens

<400> SEQUENCE: 27
cgcctcacct gctcttcaag 20

<210> SEQ ID NO 28
<211> LENGTH: 19
<212> TYPE: DNA
<213> ORGANISM: Homo sapiens

<400> SEQUENCE: 28
cagtcacagc ggagtgaat 19

<210> SEQ ID NO 29
<211> LENGTH: 21
<212> TYPE: DNA
<213> ORGANISM: Homo sapiens

<400> SEQUENCE: 29
cttttgcatc tgcatgggtc t 21

<210> SEQ ID NO 30
<211> LENGTH: 19
<212> TYPE: DNA
<213> ORGANISM: Homo sapiens

<400> SEQUENCE: 30
ccactgccgg actccaccc 19

<210> SEQ ID NO 31
<211> LENGTH: 20
<212> TYPE: DNA
<213> ORGANISM: Homo sapiens

<400> SEQUENCE: 31
gcatctgctc cctctaccag                                          20

<210> SEQ ID NO 32
<211> LENGTH: 20
<212> TYPE: DNA
<213> ORGANISM: Homo sapiens

<400> SEQUENCE: 32
ggttcaaggg ctttattcca                                          20

<210> SEQ ID NO 33
<211> LENGTH: 28
<212> TYPE: DNA
<213> ORGANISM: Homo sapiens

<400> SEQUENCE: 33
tggagaacta ctgcaactag acgcagcc                                 28

<210> SEQ ID NO 34
<211> LENGTH: 20
<212> TYPE: DNA
<213> ORGANISM: Homo sapiens

<400> SEQUENCE: 34
ccaaccagac ggagaatgat                                          20

<210> SEQ ID NO 35
<211> LENGTH: 20
<212> TYPE: DNA
<213> ORGANISM: Homo sapiens

<400> SEQUENCE: 35
tagccgggtt tgagttagca                                          20

<210> SEQ ID NO 36
<211> LENGTH: 28
<212> TYPE: DNA
<213> ORGANISM: Homo sapiens

<400> SEQUENCE: 36
atgaaatgag gcttgagctg cagagatc                                 28

<210> SEQ ID NO 37
<211> LENGTH: 18
<212> TYPE: DNA
<213> ORGANISM: Homo sapiens

<400> SEQUENCE: 37
ggacctgcaa tttcattg                                            18

<210> SEQ ID NO 38
<211> LENGTH: 18
<212> TYPE: DNA
<213> ORGANISM: Homo sapiens

<400> SEQUENCE: 38
ctccagcaaa gaggaaaa                                            18

<210> SEQ ID NO 39
<211> LENGTH: 23
<212> TYPE: DNA
<213> ORGANISM: Homo sapiens

```
<400> SEQUENCE: 39
taaggtccac agaagtccgc aat                                              23

<210> SEQ ID NO 40
<211> LENGTH: 18
<212> TYPE: DNA
<213> ORGANISM: Homo sapiens

<400> SEQUENCE: 40
cacgatgaat ttgagaga                                                    18

<210> SEQ ID NO 41
<211> LENGTH: 18
<212> TYPE: DNA
<213> ORGANISM: Homo sapiens

<400> SEQUENCE: 41
cagagaaaga accatcag                                                    18

<210> SEQ ID NO 42
<211> LENGTH: 24
<212> TYPE: DNA
<213> ORGANISM: Homo sapiens

<400> SEQUENCE: 42
cttcaacaat ggcgacctct tctg                                             24

<210> SEQ ID NO 43
<211> LENGTH: 20
<212> TYPE: DNA
<213> ORGANISM: Homo sapiens

<400> SEQUENCE: 43
cccgtttgga taaagaattg                                                  20

<210> SEQ ID NO 44
<211> LENGTH: 18
<212> TYPE: DNA
<213> ORGANISM: Homo sapiens

<400> SEQUENCE: 44
ccttcacttg cttcagtc                                                    18

<210> SEQ ID NO 45
<211> LENGTH: 24
<212> TYPE: DNA
<213> ORGANISM: Homo sapiens

<400> SEQUENCE: 45
attgtattca tcagcagcag ccat                                             24

<210> SEQ ID NO 46
<211> LENGTH: 18
<212> TYPE: DNA
<213> ORGANISM: Homo sapiens

<400> SEQUENCE: 46
ctccttgctg aatctgag                                                    18

<210> SEQ ID NO 47
<211> LENGTH: 19
<212> TYPE: DNA
<213> ORGANISM: Homo sapiens
```

```
<400> SEQUENCE: 47
ccacaaagat tgctatcac                                            19

<210> SEQ ID NO 48
<211> LENGTH: 20
<212> TYPE: DNA
<213> ORGANISM: Homo sapiens

<400> SEQUENCE: 48
caaccaccat caaggcacgg                                           20

<210> SEQ ID NO 49
<211> LENGTH: 18
<212> TYPE: DNA
<213> ORGANISM: Homo sapiens

<400> SEQUENCE: 49
ctcccagaca tctttgag                                             18

<210> SEQ ID NO 50
<211> LENGTH: 18
<212> TYPE: DNA
<213> ORGANISM: Homo sapiens

<400> SEQUENCE: 50
gcggtggtta atttcatc                                             18

<210> SEQ ID NO 51
<211> LENGTH: 20
<212> TYPE: DNA
<213> ORGANISM: Homo sapiens

<400> SEQUENCE: 51
agtcctccac cacatcctgc                                           20

<210> SEQ ID NO 52
<211> LENGTH: 18
<212> TYPE: DNA
<213> ORGANISM: Homo sapiens

<400> SEQUENCE: 52
gctcaaaacc agatacag                                             18

<210> SEQ ID NO 53
<211> LENGTH: 19
<212> TYPE: DNA
<213> ORGANISM: Homo sapiens

<400> SEQUENCE: 53
gacacatcca agaatactg                                            19

<210> SEQ ID NO 54
<211> LENGTH: 20
<212> TYPE: DNA
<213> ORGANISM: Homo sapiens

<400> SEQUENCE: 54
tctccacgct caaccgctta                                           20

<210> SEQ ID NO 55
<211> LENGTH: 18
<212> TYPE: DNA
```

<213> ORGANISM: Homo sapiens

<400> SEQUENCE: 55
acctctactt tgccaatg                                                    18

<210> SEQ ID NO 56
<211> LENGTH: 18
<212> TYPE: DNA
<213> ORGANISM: Homo sapiens

<400> SEQUENCE: 56
ctgtcaatca tgctgttg                                                    18

<210> SEQ ID NO 57
<211> LENGTH: 21
<212> TYPE: DNA
<213> ORGANISM: Homo sapiens

<400> SEQUENCE: 57
acctccgaca accactcaga c                                                21

<210> SEQ ID NO 58
<211> LENGTH: 18
<212> TYPE: DNA
<213> ORGANISM: Homo sapiens

<400> SEQUENCE: 58
cgtcttcatc atcttcac                                                    18

<210> SEQ ID NO 59
<211> LENGTH: 18
<212> TYPE: DNA
<213> ORGANISM: Homo sapiens

<400> SEQUENCE: 59
tgggatagaa gctttgta                                                    18

<210> SEQ ID NO 60
<211> LENGTH: 24
<212> TYPE: DNA
<213> ORGANISM: Homo sapiens

<400> SEQUENCE: 60
tgctcctggt tctgttcttc atct                                             24

<210> SEQ ID NO 61
<211> LENGTH: 18
<212> TYPE: DNA
<213> ORGANISM: Homo sapiens

<400> SEQUENCE: 61
cagagcaact ggaagaag                                                    18

<210> SEQ ID NO 62
<211> LENGTH: 18
<212> TYPE: DNA
<213> ORGANISM: Homo sapiens

<400> SEQUENCE: 62
ctcgttgtcc ttcttgaa                                                    18

<210> SEQ ID NO 63
<211> LENGTH: 21

<212> TYPE: DNA
<213> ORGANISM: Homo sapiens

<400> SEQUENCE: 63
tggtggctcg ttctccttct c                                             21

<210> SEQ ID NO 64
<211> LENGTH: 18
<212> TYPE: DNA
<213> ORGANISM: Homo sapiens

<400> SEQUENCE: 64
gacctgctca atgttaag                                                 18

<210> SEQ ID NO 65
<211> LENGTH: 19
<212> TYPE: DNA
<213> ORGANISM: Homo sapiens

<400> SEQUENCE: 65
caaccgtctt aatcagaag                                                19

<210> SEQ ID NO 66
<211> LENGTH: 26
<212> TYPE: DNA
<213> ORGANISM: Homo sapiens

<400> SEQUENCE: 66
cttgacattg agattgccac ctacag                                        26

<210> SEQ ID NO 67
<211> LENGTH: 18
<212> TYPE: DNA
<213> ORGANISM: Homo sapiens

<400> SEQUENCE: 67
gtgctaaagg tgccaatg                                                 18

<210> SEQ ID NO 68
<211> LENGTH: 18
<212> TYPE: DNA
<213> ORGANISM: Homo sapiens

<400> SEQUENCE: 68
gtccttgaac accaacag                                                 18

<210> SEQ ID NO 69
<211> LENGTH: 21
<212> TYPE: DNA
<213> ORGANISM: Homo sapiens

<400> SEQUENCE: 69
tcctggtatt gctggtgctc c                                             21

<210> SEQ ID NO 70
<211> LENGTH: 22
<212> TYPE: DNA
<213> ORGANISM: Homo sapiens

<400> SEQUENCE: 70
gggaatggag caaaacagtc tt                                            22

<210> SEQ ID NO 71

```
<211> LENGTH: 21
<212> TYPE: DNA
<213> ORGANISM: Homo sapiens

<400> SEQUENCE: 71
ccaacgtcca caccaaattc t                                              21

<210> SEQ ID NO 72
<211> LENGTH: 27
<212> TYPE: DNA
<213> ORGANISM: Homo sapiens

<400> SEQUENCE: 72
tcgaacacgc aaggctgtga gactacc                                        27

<210> SEQ ID NO 73
<211> LENGTH: 20
<212> TYPE: DNA
<213> ORGANISM: Homo sapiens

<400> SEQUENCE: 73
accacagtcc atgccatcac                                                20

<210> SEQ ID NO 74
<211> LENGTH: 20
<212> TYPE: DNA
<213> ORGANISM: Homo sapiens

<400> SEQUENCE: 74
tccaccaccc tgttgctgta                                                20

<210> SEQ ID NO 75
<211> LENGTH: 21
<212> TYPE: DNA
<213> ORGANISM: Homo sapiens

<400> SEQUENCE: 75
ctgcaccacc aactgcttag c                                              21
```

METHOD OF INDUCING BETA CELLS FROM URINE-DERIVED CELLS USING SMALL MOLECULES

CROSS-REFERENCE TO RELATED APPLICATIONS

The present application is a national state application under 35 U.S.C. 371 and claims the benefit of PCT Application No. PCT/AU2015/000760 having an international filing date of 22 Dec. 2015, which designated the United States, which PCT application claimed the benefit of Australian patent application no. 2014905202 filed on 22 Dec. 2014, the disclosures of each of which are incorporated herein by reference.

INCORPORATION BY REFERENCE

The following co-pending patent application is referred to herein:
PCT/AU2012/001525 titled "Method of producing multipotent stem cells", published as WO 2013/086570.
The content of this application is hereby incorporated by reference in its entirety.

TECHNICAL FIELD

The present disclosure relates to a method of inducing cells, and the cells induced by the method. In a particular form, the present disclosure relates to inducing beta cells.

BACKGROUND

The term Diabetes mellitus (DM), or simply diabetes, refers to a group of metabolic diseases in which a subject has "high blood sugar", either because the pancreas is not producing sufficient insulin or otherwise, because cells within the subject are insensitive or "resistant" to insulin (ie do not respond properly to the insulin that is produced). The classical symptoms of these diseases are polyuria (ie frequent urination), polydipsia (ie increased thirst) and polyphagia (ie increased hunger), and there are two main types, namely type 1 DM and type 2 DM. Type 1 DM results from the body's failure to produce insulin and medical intervention currently requires that the subject administers insulin usually either by injection or via an insulin pump. Type 2 DM on the other hand results from insulin resistance, a condition in which the cells fail to use insulin properly, sometimes combined with an absolute insulin deficiency. As a principal hormone, insulin regulates the uptake of glucose from the blood into most cells (primarily muscle and fat cells, but not central nervous system cells). Therefore, a deficiency of insulin or insensitivity in the insulin receptors plays a central role in all forms of DM.

DM is an enormous medical problem with, globally, an estimated 285 million patients affected (with type 2 DM affecting about 90% of those patients). Worryingly, the incidence of DM is increasing rapidly and, by 2030, it is anticipated that the present numbers of affected patients could be doubled (Wild et al., 2004). Accordingly, there is a need to identify alternative therapies for DM which, desirably, are less invasive and more efficacious than the present standard treatment options. In this regard, there has been considerable research conducted into the potential use of stem cell therapies to generate new insulin-secreting pancreatic cells (ie beta islet cells or beta cells) in patients. In a recent report, a group from the Harvard University have produced fully mature, glucose-responsive beta cells from both human embryonic stem cells (ESCs) and human induced pluripotent stem cells (iPSCs) and transplanted these into a diabetic mouse model to "cure" the mouse of the disease within a few days (Pagliuca et al., 2014). Moreover, a competing group at Viacyte, Inc. (San Diego, Calif., United States of America) is shortly to undertake a clinical trial involving the transplantation of somewhat less mature ES cell-derived islet cells contained within an immunoprotective capsule (D'Amour et al., 2006). In addition, insulin-secreting beta cells have been generated from other stem cell types such as rat and human neural stem cells (Hori et al., 2005, and Kuwabara et al., 2011), and also induced from human fibroblast cells (a mature cell type) using a small molecule inducer, namely 5-azacytidine (AzaC) (Pennarossa et al., 2013).

The induction of stem cells and/or immature cell types from mature cells is of considerable interest to the present applicant since it offers the potential of generating cells of therapeutic significance from readily available and comparably non-invasive sources of autologous cells. However, typically, the protocols for reprogramming cells into iPSCs involves introducing to the cells one or more polynucleotide molecules encoding polypeptide reprogramming factors, or by directly introducing polypeptide reprogramming factors (eg transcription factors and other factors associated with reprogramming, such as Oct-3/4 (Pou5fl), Sox family (eg Sox1, Sox2, Sox3, Sox15, Sox18, etc), Myc family (eg c-Myc, N-mvc, L-myc), Klf family (eg Klf1, Klf2, Klf4, Kfl5, etc), Nanog, Lin28 etc). Such polynucleotide molecules or polypeptide reprogramming factors can be introduced into cells as genetic material using viral transfection vectors (eg retroviruses), or plasmids, or be introduced as mRNA or miRNAs, or as polypeptides (eg recombinant polypeptides). There has been considerable concern over the risks associated with such viral transfection vectors and/or exogenous and potentially oncogenic transcription factors and related factors associated with reprogramming (eg potential to induce cancer), which has to-date caused some limitation on the use of iPSCs in therapy.

Recently, research has elucidated a way by which various small molecules can be used to replace certain polypeptide or polynucleotide reprogramming factors (such that fewer transcription factors can be used in the induction) so as to improve the stem cell induction efficiency and diversity in the reprogramming process (see, for example, Shi et al., 2008; Huangfu et al., 2008; and Maherali & Hochedlinger, 2009). Intrigued by such research, the present applicant previously conducted experimentation to determine whether it may be possible to produce iPSCs using only small molecules. Using a selection of one or more small molecules, their work, while being unsuccessful in producing iPSCs, did achieve the induction of somatic cells such as fibroblasts into multipotent cells such as neural stem cells (denoted as small molecule-induced neural stem (SMINS) cells). The protocols for production of SMINS are described in PCT/AU2012/001525 (WO 2013/086570), the content of which is hereby incorporated by reference.

In work leading to the present disclosure, the present applicant sought to identify whether similar protocols, using only small molecules (thereby avoiding the use of polypeptide reprogramming factors and polynucleotide molecules encoding polypeptide reprogramming factors), could be developed for the generation of cells such as beta cells capable of secreting insulin. Desirably, the present applicant sought protocols which avoid the use of otherwise toxic molecules such as the small molecule inducer mentioned above (ie AzaC) which is known to be mutagenic.

SUMMARY

According to a first aspect of the present disclosure, there is provided a method of producing induced beta cells from urine-derived cells, the method comprising:
(a) providing urine-derived cells;
(b) inducing the urine-derived cells provided in step (a) by culturing said urine-derived cells in a primary induction culture medium comprising an effective amount of at least one small molecule reprogramming factor(s) for a first period of time to obtain induced endoderm cells;
(c) inducing the induced endoderm cells obtained in step (b) by culturing said induced endoderm cells in a secondary induction culture medium comprising an effective amount of at least one small molecule reprogramming factor(s) for a second period of time to obtain induced pancreatic precursor cells; and
(d) inducing the induced pancreatic precursor cells obtained in step (c) by culturing said pancreatic precursor cells in a tertiary induction culture medium comprising an effective amount of at least one small molecule reprogramming factor(s) for a third period of time to obtain induced beta cells.

In an embodiment, the primary induction medium comprises an effective amount of at least one small molecule reprogramming factor(s) selected from the group consisting of a definitive endoderm inducer, a glycogen synthase kinase 3 (GSK3) inhibitor and Vitamin C.

In an embodiment, the primary induction medium comprises an effective amount of a combination of small molecule reprogramming factor(s) comprising a definitive endoderm inducer, a glycogen synthase kinase 3 (GSK3) inhibitor and Vitamin C.

In an embodiment, the secondary induction medium comprises an effective amount of at least one small molecule reprogramming factor(s) selected from the group consisting of a PKC activator, a sonic hedgehog (SSH) inhibitor, a retinoic acid receptor (RAR) agonist, Vitamin C, an activin receptor-like kinase (ALK) receptor inhibitor, and a Pdx1 inducer.

In an embodiment, the secondary induction medium comprises an effective amount of at least one small molecule reprogramming factor(s) selected from the group consisting of a PKC activator, a sonic hedgehog (SSH) inhibitor, a retinoic acid receptor (RAR) agonist, Vitamin C, an activin receptor-like kinase (ALK) receptor inhibitor, a Pdx1 inducer and a bone morphogenetic protein (BMP) inhibitor.

In an embodiment, the second period of time consists of a first portion and a second portion, and wherein the secondary induction medium comprises an effective amount of at least one small molecule reprogramming factor(s) selected from the group consisting of:
a PKC activator, a sonic hedgehog (SSH) inhibitor, a retinoic acid receptor (RAR) agonist, Vitamin C, an activin receptor-like kinase (ALK) receptor inhibitor, and a Pdx1 inducer for a first portion of the second period of time, and
a PKC activator, a sonic hedgehog (SSH) inhibitor, Vitamin C, an activin receptor-like kinase (ALK) receptor inhibitor, and a Pdx1 inducer for a second portion of the second period of time.

In an embodiment, the second period of time consists of a first portion, a second portion and a third portion, and wherein the secondary induction medium comprises an effective amount of at least one small molecule reprogramming factor(s) selected from the group consisting of:
Vitamin C for the first portion of the second period of time;
Vitamin C, a RAR agonist, a SSH inhibitor, a PKC activator and a BMP nhibitor for a second portion of the second period of time; and
Vitamin C, a RAR agonist, and a SSH inhibitor for a third portion of the second period of time.

In an embodiment, the third induction medium comprises an effective amount of at least one small molecule reprogramming factor(s) selected from the group consisting of a mitogen-activated protein kinase kinase (MEK) inhibitor, Vitamin C and a notch inhibitor.

In an embodiment, the tertiary induction medium comprises an effective amount of at least one small molecule reprogramming factor(s) selected from the group consisting of a mitogen-activated protein kinase kinase (MEK) inhibitor, Vitamin C, a notch inhibitor, an ALK receptor inhibitor, triiodothyronine, an RAR agonist, and a SSH inhibitor.

In an embodiment, the definitive endoderm inducer is IDE1. In an embodiment, the GSK inhibitor is lithium chloride. In an embodiment, the PKC activator is indolactam V. In an embodiment, the SSH inhibitor is cyclopamine-KAAD. In an embodiment, the RAR agonist is retinoic acid. In an embodiment, the ALK receptor inhibitor is A83-01. In an embodiment, the Pdx-1 inducer is BRD 7552. In an embodiment, the MEK inhibitor is SB2033580. In an embodiment, the notch inhibitor is DAPT. In an embodiment, the BMP inhibitor is dorsomorpin.

In an embodiment:
the primary induction medium comprises an effective amount of IDE1, lithium chloride and Vitamin C;
the secondary induction medium comprises an effective amount of
Indolactam V, cyclopamine-KAAD, Vitamin C, retinoic acid, A83-01, and BRD 7552 for a first portion of the second period of time, and
Indolactam V, cyclopamine-KAAD, Vitamin C, A83-01, and BRD 7552 for a second portion of the second period of time; and
the third induction medium comprises an effective amount of SB203580, Vitamin C and DAPT.

In an embodiment:
the primary induction medium comprises an effective amount of IDE1, lithium chloride and Vitamin C;
the secondary induction medium comprises an effective amount of
Vitamin C for a first portion of the second period of time;
Vitamin C, RA, cyclopamine-KAAD, Indolactam V and dorsomorphin for a second portion of the second period of time; and
Vitamin C, RA, and cyclopamine-KAAD for a third portion of the second period of time; and
the tertiary induction medium comprises an effective amount of
Vitamin C, RA, cyclopamine-KAAD, DAPT, A83-01, and triiodothyronine for a first portion of the third period of time,
Vitamin C, RA, DAPT, A83-01, and triiodothyronine for a second portion of the third period of time, and
Vitamin C and triiodothyronine for a third portion of the third period of time.

In an embodiment, the urine-derived cells are obtained from a urine sample of a subject. In an embodiment, the urine-derived cells are human cells.

In an embodiment, step (a) further comprises expanding the urine-derived cells by culturing the urine-derived cells in an appropriate tissue culture medium.

In an embodiment, the method excludes the use of reprogramming factors that are not small molecules.

In a second aspect, the present disclosure provides a method of producing an induced endoderm cell from a urine-derived cell, the method comprising:
(a) providing urine-derived cells; and
(b) inducing the urine-derived cells obtained in step (a) by culturing said urine-derived cells in a primary induction culture medium comprising an effective amount of at least one small molecule reprogramming factor(s) for a first period of time to obtain induced endoderm cells.

In a third aspect, the present disclosure provides a method of producing an induced pancreatic precursor cell from a urine-derived cell, the method comprising:
(a) providing urine-derived cells;
(b) inducing the urine-derived cells obtained in step (a) by culturing said urine-derived cells in a primary induction culture medium comprising an effective amount of at least one small molecule reprogramming factor(s) for a first period of time to obtain induced endoderm cells; and
(c) inducing the induced endoderm cells obtained in step (b) by culturing said induced endoderm cells in a secondary induction culture medium comprising an effective amount of at least one small molecule reprogramming factor(s) for a second period of time to obtain induced pancreatic precursor cells.

In a fourth aspect, the present disclosure provides a method of producing an induced pancreatic precursor cell from an endoderm cell, the method comprising:
providing endoderm cells; and
inducing the obtained endoderm cells by culturing said endoderm cells in an induction culture comprising an effective amount of at least one small molecule reprogramming factor(s) selected from the group consisting of a PKC activator, a sonic hedgehog (SSH) inhibitor, a retinoic acid receptor (RAR) agonist, Vitamin C, an activin receptor-like kinase (ALK) receptor inhibitor, and a Pdx1 inducer for a period of time to obtain induced pancreatic precursor cells.

In a fifth aspect, the present disclosure provides a method of producing an induced beta cell from a pancreatic precursor cell, the method comprising:
providing pancreatic precursor cells; and
inducing the obtained pancreatic precursor cells by culturing said pancreatic precursor cells in an induction culture medium comprising an effective amount of at least one small molecule reprogramming factor(s) selected from the group consisting of a mitogen-activated protein kinase kinase (MEK) inhibitor, Vitamin C and a notch inhibitor for a period of time to obtain induced beta cells.

In a sixth aspect, the present disclosure provides cells obtained using the method of any one of the aspects of the disclosure.

BRIEF DESCRIPTION OF FIGURES

FIG. 5 provides micrograph images of cells collected from human urine following primary induction with primary induction media containing Activin A, LiCl, and Vitamin C for 6 days and secondary induction in secondary induction media containing Indolactam V, L-glutamine, and B27, retinoic acid (RA), Vitamin C (VC) and A83-01 for one day, and then Vitamin C and A83-01 for seven days, scale bar=100 μm;

FIG. 6 provides (a) a phase contrast image and (b) fluorescent micrograph image of cells, collected from human urine, following primary induction with primary induction media containing Activin A, LiCl, and Vitamin C for 6 days and secondary induction in secondary induction media containing Indolactam V, L-glutamine, B27, retinoic acid (RA), Vitamin C (VC) and A83-01 for one day, and then Vitamin C and A83-01 for seven days, which were then infected with Pdx1-cy3-insulin-488 lentivirus, scale bar=100 μm;

DETAILED DESCRIPTION

Figure 1:
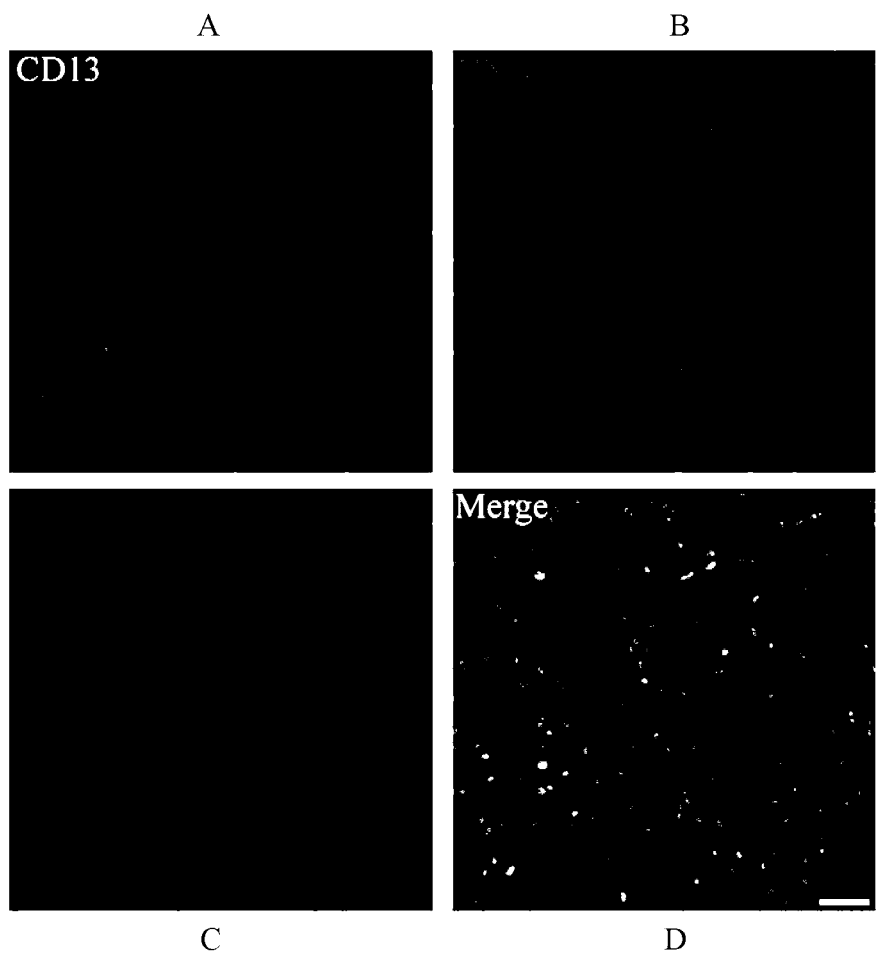
FIG. 1 provides fluorescent micrograph images of human urine cells (HUC) collected from a 35 year old human male donor ("M-35") stained for (a) CD13 expression, (b) human nuclear antigen (HNA) expression, (c) DAPI, and (d) merged images, scale bar: 100 μm.

The present applicant has identified a novel and safe method to efficiently induce beta cells from somatic cells such as urine-derived cells using three inducing steps, each utilising at least one induction culture medium comprising at least one small molecule reprogramming molecule(s) for the induction. In some embodiments, the method excludes the use of reprogramming factor(s) that are not small molecules. Advantageously, the method reduces the concerns of integrating potentially harmful viral transfection vectors and/or the introduction of polynucleotide or polypeptide reprogramming factors such as oncogenic transcription factors, and seeks to avoid the use of otherwise toxic molecules such as the small molecule inducer mentioned above (ie AzaC) which is known to be mutagenic. Additionally, this method is particularly advantageous as it utilises cells that are readily available, that can be collected through non-invasive methods. Accordingly, this method may represent an important step forward towards the tailoring of individualised cell-based therapies for subjects with diseases involving insulin deficiencies or insensitivities such as Diabetes mellitus (DM).

According to a first aspect of the present disclosure, there is provided a method of producing an induced beta cell from a urine-derived cell, the method comprising:
(a) providing urine-derived cells;
(b) inducing the urine-derived cells provided in step (a) by culturing said urine-derived cells in a primary induction culture medium comprising an effective amount of at least one small molecule reprogramming factor(s) for a first period of time to obtain induced endoderm cells;
(c) inducing the induced endoderm cells obtained in step (b) by culturing said induced endoderm cells in a secondary induction culture medium comprising an effective amount of at least one small molecule reprogramming factor(s) for a second period of time to obtain induced pancreatic precursor cells; and
(d) inducing the induced pancreatic precursor cells obtained in step (c) by culturing said pancreatic precursor cells in a tertiary induction culture medium comprising an effective amount of at least one small molecule reprogramming factor(s) for a third period of time to obtain induced beta cells.

As used herein, the term "small molecule" is to be understood as referring to a low molecular weight compound that has a biological function, as would be understood by the person skilled in the art. By definition, a small molecule is not a polymer, unless it is a very small oligomer (eg consisting of two or possibly three monomers). Accordingly, a small molecule is not a polynucleotide or polypeptide such as a gene, a primer, transposon, or other DNA polynucleotide molecule, an RNA polynucleotide molecule that encodes a protein or polypeptide (eg double-stranded RNA, mRNA (ie sense RNA), or the complement to mRNA (ie antisense strand of a RNA duplex)), a microRNA (miRNA) molecule or interfering RNA (RNAi) molecule, or other RNA polynucleotide molecule, or a polypeptide, or a fragment of any of these polynucleotide or polypeptide molecules, unless said fragment is a monomer or a very small oligomer such as a dinucleotide, dipeptide or tripeptide. A small molecule of the present disclosure is typically an organic compound; however, some non-organic chemicals may be a small molecule of the present disclosure, such as lithium chloride or sodium butyrate. The upper molecular weight limit for a small molecule is generally considered to be approximately 800 g/mol (ie approximately 800 Daltons).

However, the person skilled in the art will appreciate that a small molecule could have an upper molecular weight limit of approximately 900 g/mol. A small molecule generally binds in a specific manner to a biopolymer such as a polypeptide or polynucleotide molecule, etc, and alters the activity or function of that polypeptide or polynucleotide molecule (eg activates or inhibits the function of a particular enzyme, etc).

As used herein, the term "reprogramming factor" is intended to refer to a molecule that is associated with cell "reprogramming", that is, differentiation, and/or de-differentiation, and/or transdifferentiation, such that a cell converts to a different cell type or phenotype. Reprogramming factors generally affect expression of genes associated with cell differentiation, de-differentiation and/or transdifferentiation. Transcription factors are examples of reprogramming factors.

The person skilled in the art will appreciate that "differentiation" as used herein refers to the process by which a less specialised cell (ie a more naïve cell with a higher cell potency) becomes a more specialised cell type (ie a less naïve cell with a lower cell potency); and that the term "de-differentiation" refers to the process by which a more specialised cell becomes a less specialised cell type (ie a more naïve cell with a higher cell potency); and that the term "transdifferentiation" refers to the process by which a cell of a particular cell type converts to another cell type without significantly changing its "cell potency" or "naivety" level. Without wishing to be bound by theory, it is thought that cells "transdifferentiate" when they convert from one lineage-committed cell type or terminally differentiated cell type to another lineage-committed cell type or terminally differentiated cell type, without significantly changing their "cell potency" or "naivety" level. As used herein, the term "cell potency" is to be understood as referring to the ability of a cell to differentiate into cells of different lineages. For example, a pluripotent cell (eg a stem cell) has the potential to differentiate into cells of any of the three germ layers, that is, endoderm (interior stomach lining, gastrointestinal tract, the lungs), mesoderm (muscle, bone, blood, urogenital), or ectoderm (epidermal tissues and nervous system), and accordingly has high cell potency; a multipotent cell (eg a stem cell or an induced stem cell of a certain type) has the ability to give rise to cells from a multiple, but limited, number of lineages (such as haematopoietic stem cells, cardiac stem cells, or neural stem cells, etc) comparatively has a lower cell potency than pluripotent cells. Cells that are committed to a particular lineage or are terminally differentiated would have yet a lower cell potency. Specific examples of transdifferentiation known in the art include the conversion of fibroblasts to muscle cells (Davis et al. 1987), neurons (Vierburchen et al., 2010), beta cells (Pennarossa et al. 2013) or cardiomyocytes (Efe et al, 2011) or from pancreatic exocrine cells to beta cells (Zhou et al., 2008); etc.

Accordingly, the cell may be caused to differentiate into a more naïve cell (eg a terminally differentiated cell may be differentiated to be multipotent or pluripotent); or the cell may be caused to de-differentiate into a less naïve cell (eg a multipotent or pluripotent cell may be differentiated into a lineage-committed cell or a terminally differentiated cell). However, in an embodiment, the cell may be caused to convert or transdifferentiate from one cell type (or phenotype) to another cell type (or phenotype), for example, with a similar cell potency level. Accordingly, in an embodiment of the present disclosure, the inducing steps of the present disclosure may reprogram the cells of the present disclosure to differentiate, de-differentiate and/or transdifferentiate. In an embodiment of the present disclosure, the inducing steps of the present disclosure may reprogram the cells to transdifferentiate.

A "polynucleotide or polypeptide reprogramming factor" as used herein is to be understood as referring to a polynucleotide or polypeptide molecule that is associated with differentiation, de-differentiation, and/or transdifferentiation. It is to be understood that the polynucleotide or polypeptide reprogramming factor could, for example, be a gene, a primer, transposon, or other DNA polynucleotide molecule, an RNA polynucleotide molecule that encodes a protein or peptide (eg double-stranded RNA, mRNA (ie sense RNA), or the complement to mRNA (ie antisense strand of a RNA duplex)), a microRNA (miRNA) molecule or interfering RNA (RNAi) molecule, or other RNA polynucleotide molecule, or a polypeptide, or a fragment of any of these polynucleotide or polypeptide molecules, providing said fragment is not a monomer or a very small oligomer such as a dinucleotide, dipeptide or tripeptide.

Methods of reprogramming or inducing a particular type of cell to become another type of cell, for example, by differentiation, de-differentiation and/or transdifferentiation using one or more exogenous polynucleotide or polypeptide reprogramming factors are known to the person skilled in the art. Such methods may rely on the introduction of genetic material encoding one or more transcription factor(s) or other polypeptide(s) associated with cell reprogramming. For example, Pdx1, Ngn3 and MafA, or functional fragments thereof are all known to encode peptides that can induce cell differentiation, de-differentiation and/or transdifferentiation of the cells of the present disclosure. In some methods known to the person skilled in the art, exogenous polypeptides (eg recombinant polypeptides) encoded by reprogramming genes (such as the above genes) are contacted with the cells to induce, for example, cells of the present disclosure. The person skilled in the art will appreciate that other genes may be associated with reprogramming of cells, and exogenous molecules encoding such genes (or functional fragments thereof) and the encoded polypeptides are also considered to be polynucleotide or polypeptide reprogramming factors (eg polynucleotides or polypeptides that in turn affect expression levels of another gene associated with cell reprogramming). For example, it has been shown that the introduction of exogenous polynucleotide or polypeptide epigenetic gene silencers that decrease p53 inactivation increase the efficiency of inducing induced pluripotent stem cells (iPSC). Accordingly, exogenous polynucleotides or polypeptides encoding epigenetic silencers and other genes or proteins that may be directly or indirectly involved in cell reprogramming or increasing cell programming efficiency would be considered to constitute an exogenous polynucleotide or polypeptide reprogramming factor. The person skilled in the art will appreciate that other methods of influencing cell reprogramming exist, such as introducing RNAi molecules (or genetic material encoding RNAi molecules) that can knock down expression of genes involved in inhibiting cell reprogramming. Accordingly, any exogenous polynucleotide molecule or polypeptide molecule that is associated with cell reprogramming, or enhances cell reprogramming, is to be understood to be an exogenous polynucleotide or polypeptide reprogramming factor as described herein.

As would be appreciated, the term "small molecule reprogramming factor" refers to reprogramming factors that are small molecules as defined herein. Such small molecules are described in detail elsewhere herein.

In some embodiments of the present disclosure, the method excludes the use of reprogramming factor(s) that are not small molecules. However, it will be appreciated that the method may utilise "routine" tissue culture components such as culture media, serum, serum substitutes, supplements, antibiotics, etc, such as RPMI, Renal Epithelial Basal Medium (REBM), Dulbecco's Modified Eagle Medium (DMEM), MCDB131 medium, CMRL 1066 medium, F12, foetal calf serum (FCS), foetal bovine serum (FBS), bovine serum albumin (BSA), D-glucose, L-glutamine, Gluta-MAX™-1 (dipeptide, L-alanine-L-glutamine), B27, heparin, progesterone, putrescine, laminin, nicotinamide, insulin, transferrin, sodium selenite, selenium, ethanolamine, human epidermal growth factor (hEGF), basic fibroblast growth factor (bFGF), hydrocortisone, epinephrine, normacin, penicillin, streptomycin, gentamicin and amphotericin, etc. It is to be understood that these typical tissue culture components (and other similar tissue culture components that are routinely used in tissue culture) are not small molecule reprogramming molecules for the purposes of the present disclosure. Indeed, these components are either not small molecules as defined herein and/or are not reprogramming factors as defined herein.

Accordingly, in an embodiment, the present disclosure does not involve a culturing step of the cell(s) with one or more exogenous polynucleotide or polypeptide reprogramming factor(s). Accordingly, in an embodiment, the method of the present disclosure does not involve the introduction of one or more exogenous polynucleotide or polypeptide reprogramming factor(s), eg by introducing transposons, viral transgenic vectors (such as retroviral vectors), plasmids, mRNA, miRNA, peptides, or fragments of any of these molecules, that are involved in producing induced beta cells or, otherwise, inducing cells of the present disclosure to differentiate, de-differentiation and/or transdifferentiate.

That is, in an embodiment, the method occurs in the absence of one or more exogenous polynucleotide or polypeptide reprogramming factor(s). Accordingly, it is to be understood that in an embodiment, the method of the present disclosure utilises only small molecules to reprogram cells, without the addition of polypeptide transcription factors; other polypeptide factors specifically associated with inducing differentiation, de-differentiation, and/or transdifferentiation; polynucleotide sequences encoding polypeptide transcription factors, polynucleotide sequences encoding other polypeptide factors specifically associated with inducing differentiation, de-differentiation, and/or transdifferentiation; mRNA; interference RNA; microRNA and fragments thereof. Notably, in an embodiment, the method of the present disclosure does not include the addition of one or more polynucleotides or polypeptides selected from the group consisting of pdx1, ngn3 and/or MafA, etc, and functional fragments thereof. Instead, the method may utilise an effective amount of at least one small molecule reprogramming factor(s) to induce reprogramming of cells. Notwithstanding this, as described elsewhere herein, in an embodiment, the present disclosure may further comprise utilising the polypeptides Activin A and/or Nodal (or active fragments thereof, or polynucleotides encoding said polypeptides or active fragments thereof) as a reprogramming factor(s). In this embodiment, it will be understood by the person skilled in the art that Activin A and Nodal are not small molecules.

The term "induced" as used herein with reference to an "induced cell" is intended to refer to a cell that has undergone changes in vitro due to the application of particular factors in tissue culture, and it is to be understood that the induced cell has phenotypic characteristics (eg morphology and/or expression of cell-type-specific markers) that are the same as or similar to the same cell type as would be found in vivo, or alternatively, in some cases, in vitro following typical tissue culture techniques (ie that do not involve the application of reprogramming factors). That is, the induced cell has been reprogrammed to be a different cell type or have a different phenotype. For example, an induced beta cell may have similar morphology and express the same peptide or genetic cell markers as beta cells found in vivo; an induced endoderm cell may have similar morphology and express the same peptide or genetic cell markers as endoderm cells found in vivo; and/or an induced pancreatic precursor cell may have similar morphology and express the same peptide or genetic cell markers as pancreatic precursor cells found in vivo.

The phrase "cells of the present disclosure" as used herein is intended to refer to urine-derived cells, induced endoderm cells, induced pancreatic precursor cells and/or induced beta cells as described herein. The phrase "induced cells of the present disclosure" as used herein is intended to refer to the induced endoderm cells, induced pancreatic precursor cells and/or induced beta cells as described herein.

The term "effective amount" as used herein, for example, with respect to the small molecule reprogramming factor will be any suitable amount of the reprogramming factor that will elicit an effect in the cells of the present disclosure. For example, an effective amount may be a sufficient amount to facilitate or contribute towards the reprogramming of the cells as described herein. Examples of suitable concentration ranges that constitute an effective amount of the small molecule reprogramming factors are described elsewhere herein. However, it is to be understood that the concentrations described herein may vary and still fall within the scope of the invention, as long as the amount of small molecule reprogramming factor used in the methods of the present disclosure is suitable to elicit an effect in the cells.

A large number of small molecule reprogramming factors are known to the person skilled in art. A small molecule reprogramming factor typically binds in a specific manner to a biopolymer such as a polypeptide or polynucleotide molecule that is involved in cell reprogramming, etc, and alters the activity or function of that polypeptide or polynucleotide molecule (for example, activates or inhibits the function of a particular enzyme that is involved in cell reprogramming, etc), and in this manner, induces cell reprogramming. A small molecule reprogramming factor(s) of the present disclosure has a molecular weight of less than 1000 g/mol. In an embodiment, the small molecule reprogramming factor(s) of the present disclosure has a molecular weight of less than 900 g/mol. In an embodiment, the small molecule reprogramming factor(s) has a molecular weight of less than 800 g/mol. In an embodiment, the small molecule reprogramming factor(s) has a molecular weight of less than 700 g/mol. In an embodiment, the small molecule reprogramming factor(s) has a molecular weight of 600 g/mol or less.

Small molecule reprogramming factors are known to include G9a histone methyltransferase (G9a HMTase) inhibitor(s), DNA methyltransferase inhibitor(s), MEK inhibitor(s), histone deacetylase (HDAC) inhibitor(s), glycogen synthase kinase 3 (GSK3) inhibitor(s), Vitamin C, Activin receptor-like kinase (ALK) receptor inhibitor(s), inducers of definitive endoderm (IDEs), protein kinase C (PKC) inducers, sonic hedgehog (SSH) inhibitors, retinoic acid receptor activators, PDX1 inducers, notch inhibitors, bone morphogenetic protein (BMP) inhibitors and triiodothyronine. Many of these small molecules are described in PCT/AU2012/001525 mentioned above.

In an embodiment of the present disclosure, the method of the present utilises an inducer of definitive endoderm (IDE) as a reprogramming factor. IDEs include peptides Activin A and Nodal and small molecules IDE1 and IDE2 (Borowiak et al., 2009). IDE1 and IDE2 function in part via activation of TGF-β signalling, as evidenced by Smad2 phosphorylation (Borowiak et al., 2009). Suitable IDEs for use in the present disclosure include Activin A, Nodal, IDE1 (1-[2-[(2-Carboxyphenyl)methylene]hydrazide]heptanoic acid; molecular weight=306.31 g/mol), IDE2 (Heptanedioic acid-1-(2-cyclopentylidenehydrazide); molecular weight=240.3 g/mol), etc. Activin A and Nodal are not small molecules, but nonetheless may be used as an IDE in an embodiment of the present disclosure. However, in an alternative embodiment, the present disclosure excludes the use of reprogramming factors that are not small molecules. In an embodiment, the IDE is Activin A. In an embodiment, the IDE is IDE1. Suitable IDEs for use in the present disclosure may include those shown in Table 1. However, the person skilled in the art will appreciate that the list in Table 1 is not exhaustive and that other small molecule IDEs may be suitable for use in the present disclosure.

TABLE 1

Small molecule IDEs

| Chemical name | Synonyms | Molecular weight (g/mol) |
|---|---|---|
| 1-[2-[(2-Carboxyphenyl)methylene]-hydrazide]heptanoic acid | IDE1 | 306.31 |
| Heptanedioic acid-1-(2-cyclo-pentylidenehydrazide) | IDE2 | 240.3 |

The person skilled in the art will understand that an effective amount of an IDE may vary depending upon, for example, the particular selected IDE or combination of IDEs employed. In embodiments, the IDE may be used in the concentration range of 5 nM to 50 mM. In some embodiments, the IDE may be used in a concentration ranges selected from about 5 nM to 50 nM, 50 nM to 500 nM, 0.5 µM to 5 µM, 5 µM to 50 µM, 50 µM to 500 µM, and/or 5 mM to 50 mM. 5 nM to 50 mM, 0.01 µM to 100 µM, 0.1 mM to 10 mM, or 0.05 mM to 2 mM. However, generally, the IDE will be provided at a concentration in the range of 5 nM to 50 mM, or 0.01 to 10 µM. In an embodiment, for Activin A, the concentration may be in the range of 0.1 ng/ml to 100 µg/ml, or in the range of 1 ng/ml to 10 µg/ml, or approximately 10 ng/ml to 1 µg/ml. In another embodiment, for IDE1, the concentration may be in the range of 5 nM to 5 mM, or in the range of 1 µM to 1 mM, or in the range of 10 µM to 1.0 µM. Typically, the effective amount of the IDE will be provided in a culture medium suitable for the culture of the cells of the present disclosure as detailed elsewhere herein.

In an embodiment of the present disclosure, the method of the present utilises a glycogen synthase kinase 3 (GSK3) inhibitor as a small molecule reprogramming factor. Suitable GSK3 inhibitors for use in the present disclosure include lithium chloride (LiCl; molecular weight=42.39), CHIR98014 (2,6-pyridinediamine, N6-[2-[[4-(2,4-dichlorophenyl)-5-(1H-imidazol-1-yl)-2-pyrimidinyl]amino]ethyl]-3-nitro-; molecular weight=486.31 g/mol), SB216763 (3-(2,4-dichlorophenyl)-4-(1-methyl-1H-indol-3-yl)-1H-pyrrole-2,5-dione; molecular weight=371.22 g/mol), TWS 119 (3-[6-(3-aminophenyl)-7H-pyrrolo[2,3-d]pyrimidin-4-yloxy]phenol; molecular weight=318.33 g/mol) and bisindolylmaleimide I (BIM). An example of one GSK3 inhibitor is lithium chloride. Lithium chloride has been found to inhibit GSK-3β, but has not been reported to inhibit other protein kinases. In an embodiment, the GSK3 inhibitor may be CHIR 99021. Other suitable GSK3 inhibitors may include those shown in Table 2. However, the person skilled in the art will appreciate that the list in Table 2 is not exhaustive and that other small molecule GSK3 inhibitors may be suitable for use in the present disclosure.

TABLE 2

Small molecule GSK3 inhibitors

| Chemical name | Synonyms | Molecular weight (g/mol) |
|---|---|---|
| LiCl | Lithium chloride | 42.39 |
| 2,6-pyridinediamine, N6-[2-[[4-(2,4-dichlorophenyl)-5-(1H-imidazol-1-yl)-2-pyrimidinyl]amino]ethyl]-3-nitro- | CHIR98014 | 486.3 |
| 3-(2,4-dichlorophenyl)-4-(1-methyl-1H-indol-3-yl)-1H-pyrrole-2,5-dione | SB216763 | 371.2 |
| (3-[6-(3-aminophenyl)-7H-pyrrolo[2,3-d]pyrimidin-4-yloxy]phenol | TWS 119 | 318.3 |
| 6-{2-[4-(2,4-dichloro-phenyl)-5-(4-methyl-1H-imidazol-2-yl)-pyrimidin-2-ylamino]-ethylamino}-nicotinonitrile | CHIR99021, CT99021 | 465.3 |
| 3-(3-chloro-4-hydroxyphenylamino)-4-(2-nitrophenyl)-1H-pyrrole-2,5-dione | SB 415286 | 359.72 |
| 1,2,4-Thiadiazolidine-3,5-dione, 2-(1-naphthalenyl)-4-(phenylmethyl)- | Tideglusib NP031112, NP-12 | 334.39 |

The person skilled in the art will understand that an effective amount of a GSK3 inhibitor may vary depending upon, for example, the particular selected GSK3 inhibitor or combination of GSK3 inhibitors employed. In embodiments, the GSK inhibitor may be used in the concentration range of 5 nM to 50 mM. In some embodiments, the GSK inhibitor may be used in a concentration ranges selected from about 5 nM to 50 nM, 50 nM to 500 nM, 0.5 µM to 5 µM, 5 µM to 50 µM, 50 µM to 500 µM, and/or 5 mM to 50 mM. 5 nM to 50 mM, 0.01 µM to 100 µM, 0.1 mM to 10 mM, or 0.05 mM to 2 mM. In an embodiment, lithium chloride may be used in the range of 0.01 mM to 100 µM, or 0.1 mM to 10 mM, or in the range of about 0.05 mM to 2 mM. However, generally, the GSK3 inhibitor(s) will be provided for the culturing of the cell(s) of the present disclosure at a concentration in the range of 0.01 µM to 100 mM, or 0.1 µM to 10 mM, or about 0.3 µM to 1.0 mM. Typically, the effective amount of the GSK3 inhibitor(s) will be provided in a culture medium suitable for the culture of cells of the present disclosure.

In an embodiment of the present disclosure, the method utilises the small molecule reprogramming factor Vitamin C (Vc; (R)-5-((S)-1,2-dihydroxyethyl)-3,4-dihydroxyfuran-2 (5H)-one; also known as ascorbic acid and L-ascorbate; molecular weight=176.12 g/mol). Vc is a cofactor in reactions driven by dioxygenases including collagen prolyl hydroxylases, hypoxia-inducible factor (HIF), prolyl hydroxylases and histone demethylases (Shi, 2007). The person skilled in the art will understand that an effective amount of Vc may vary depending upon, for example, the particular combination of small molecule reprogramming factor(s) inhibitors employed, and the particular cell(s) undergoing reprogramming. In embodiments, Vc may be used in the concentration range of 5 nM to 50 mM. In some embodiments, Vc may be used in a concentration ranges selected from about 5 nM to 50 nM, 50 nM to 500 nM, 0.5 µM to 5 µM, 5 µM to 50 µM, 50 µM to 500 µM, and/or 5 mM to 50 mM. In an embodiment, Vc will be provided for the culturing of the cell(s) at a concentration in the range of 1 µM to 10 mM, or 10 µM to 1 mM, or about 0.1 mM to 0.5 mM. Typically, the effective amount of Vc will be provided in a culture medium suitable for the culture of the cells of the present disclosure.

In an embodiment of the present disclosure, the method utilises a sonic hedgehog (SSH) inhibitor as a small molecule reprogramming factor. Suitable SSH inhibitors for use in the present disclosure may include those shown in Table 3. However, the person skilled in the art will appreciate that the list in Table 3 is not exhaustive and that other small molecule SSH inhibitors may be suitable for use in the present disclosure. An example of one SSH inhibitors is KAAD-cyclopamine (N-[2-[(3'R,7'aR)-3',6',10,11b-tetramethyl-3-oxospiro[1,2,4,6,6a,6b,7,8,11,11a-decahydrobenzo [a]fluorene-9,2'-3,3a,5,6,7,7a-hexahydrofuro[3,2-b]pyridine]-4'-yl]ethyl]-6-(3-phenylpropanoylamino)hexanamide; molecular weight=697.99). KAAD-Cyclopamine is a sonic hedgehog inhibitor known to target Smoothened (Pasca di Magliano & Hebrok, 2003). Hedgehog signaling is involved in embryogenesis as well as cancer progression.

TABLE 3

Small molecule SSH inhibitors

| Chemical name | Synonyms | Molecular weight (g/mol) |
|---|---|---|
| N-[2-[(3'R,7'aR)-3',6',10,11b-tetramethyl-3-oxospiro[1,2,4,6,6a,6b,7,8,11,11a-decahydrobenzo[a]fluorene-9,2'-3,3a,5,6,7,7a-hexahydrofuro[3,2-b]pyridine]-4'-yl]ethyl]-6-(3-phenylpropanoylamino)hexanamide | KAAD-Cyclopamine | 697.99 |
| (3S,3'R,3'aS,6'S,6aS,6bS,7'aR,9R,11aS,11bR)-3',6',10,11b tetramethylspiro[2,3,4,6,6a,6b,7,8,11,11a-decahydro-1H-benzo[a]fluorene-9,2'-3a,4,5,6,7,7a-hexahydro-3H-furo[3,2-b]pyridine]-3-ol | Cyclopamine | 411.62 |
| [(3R,4aR,5S,6S,6aS,10S,10aR,10bS)-3-ethenyl-6,10,10b-trihydroxy-3,4a,7,7,10a-pentamethyl-1-oxo-5,6,6a,8,9,10-hexahydro-2H-benzo[f]chromen-5-yl]acetate | Forskolin | 410.50 |
| N-(4-ethoxyphenyl)-4-(2-methylimidazol[1,2-a]pyridine-3-yl)thiazol-2-amine | SHH Inhibitor, JK184 | 350.44 |

The person skilled in the art will understand that an effective amount of a SSH inhibitor may vary depending upon, for example, the particular selected SSH inhibitor or combination of SSH inhibitor employed. In embodiments, the SSH inhibitor may be used in the range of 5 nM to 50 mM. In some embodiments, the SSH inhibitor may be used in the ranges of about 5 nM to 50 nM, 50 nM to 500 nM, 0.5 µM to 5 µM, 5 µM to 50 µM, 50 µM to 500 µM, and/or 5 mM to 50 mM. In an embodiment, KAAD-Cyclopamine will be provided for the culturing of the cell(s) of the present disclosure at a concentration in the range of 0.001 µM to 100 µM, or about 0.1 µM to 10 µM. Typically, the effective amount of the SSH inhibitor(s) will be provided in a culture medium suitable for the culture of cells of the present disclosure.

In an embodiment of the present disclosure, the method utilises a protein kinase C (PKC) activator as a small molecule reprogramming factor. Suitable PKC activators for use in the present disclosure may include those shown in Table 4. However, the person skilled in the art will appreciate that the list in Table 4 is not exhaustive and that other small molecule PKC activators may be suitable for use in the present disclosure. An example of one PKC activators is Indolactam V ((2S,5S)-1,2,4,5,6,8-Hexahydro-5-(hydroxymethyl)-1-methyl-2-(1-methylethyl)-3H-pyrrolo[4,3,2-gh]-1,4-benzodiazonin-3-one; molecular weight=301.38 g/mol).

TABLE 4

Small molecule PKC activators

| Chemical name | Synonyms | Molecular weight (g/mol) |
| --- | --- | --- |
| (2S,5S)-1,2,4,5,6,8-Hexahydro-5-(hydroxymethyl)-1-methyl-2-(1-methylethyl)-3H-pyrrolo[4,3,2-gh]-1,4-benzodiazonin-3-one | Indolactam V | 301.38 |
| (4S,5S,7E,9R,11Z,13S,15S,17S,19R,21R,25R,27R,27aS)-17-(Acetyloxy)-4,5,6,9,10,11,12,13,14,15,16,17,18,19,20,21,22,23,25,26,27,27a-docosahydro-5,15,21-trihydroxy-25-[(1R)-1-hydroxyethyl]-11-(2-methoxy-2-oxoethylidene)-6,6,16,16-tetramethyl-2,23-dioxo-5,27:9,13:15,19-triepoxy-2H-furo[2,3-e]oxacyclohexacosin-4-yl-(2E,4E)-2,4-octadienoic acid ester | Bryostatin 3 | 888.99 |
| (2Z)-2-Methyl-2-butenoic acid (1aR,2S,5R,5aS,6S,8aS,9R,10aR)-1a,2,5,5a,6,9,10,10a-octahydro-5,5a-dihydroxy-4-(hydroxymethyl)-1,1,7,9-tetramethyl-11-oxo-1H-2,8a-methanocyclopenta[a]cyclopropa[e]cyclodecen-6-yl ester | PEP005; Ingenol 3-angelate | 430.53 |
| (1aR,1bS,4aR,7aS,7bS,8R,9R,9aS)-1a,1b,4,4a,5,7a,7b,8,9,9a-Decahydro-4a,7b-dihydroxy-3-(hydroxymethyl)-1,1,6,8-tetramethyl-5-oxo-1H-cyclopropa[3,4]benz[1,2-e]azulen-9,9a-diyl butanoic acid ester | Phorbol 12,13-dibutyrate | 504.61 |
| (1aR,1bS,4aR,7aS,7bS,8R,9R,9aS)-9a-(Acetyloxy)-1a,1b,4,4a,5,7a,7b,8,9,9a-decahydro-4a,7b-dihydroxy-3-(hydroxymethyl)-1,1,6,8-tetramethyl-5-oxo-1H-cyclopropa[3,4]benz[1,2-e]azulen-9-yl tetradecanoate | Phorbol 12-myristate 13-acetate; PMA | 616.83 |
| 5-Chloro-N-heptylnaphthalene-1-sulfonamide | SC-10 | 339.88 |
| 5-Chloro-N-(6-phenylhexyl)-1-naphthalenesulfonamide | SC-9 | 401.95 |

The person skilled in the art will understand that an effective amount of a PKC activator may vary depending upon, for example, the particular selected PKC activator or combination of PKC activators employed. In embodiments, the PKC activator may be used in the concentration range of 5 nM to 50 mM. In some embodiments, the PKC activator may be used in a concentration ranges selected from about 5 nM to 50 nM, 50 nM to 500 nM, 0.5 µM to 5 µM, 5 µM to 50 µM, 50 µM to 500 µM, and/or 5 mM to 50 mM. 5 nM to 50 mM, 0.01 µM to 100 µM, 0.1 mM to 10 mM, or 0.05 mM to 2 mM. In an embodiment, Indolactam V will be provided for the culturing of the cell(s) of the present disclosure at a concentration in the range of 0.001 µM to 100 µM, or 0.01 µM to 10 µM, or about 0.1 µM to 1.0 µM. Typically, the effective amount of the PKC activator(s) will be provided in a culture medium suitable for the culture of cells of the present disclosure.

In an embodiment of the present disclosure, the method utilises a retinoic acid receptor (RAR) agonist as a small molecule reprogramming factor. Suitable RAR agonists for use in the present disclosure may include those shown in Table 5. However, the person skilled in the art will appreciate that the list in Table 5 is not exhaustive and that other small molecule RAR agonists may be suitable for use in the present disclosure. An example of one RAR agonists is retinoic acid ((2E,4E,6E,8E)-3,7-dimethyl-9-(2,6,6-trimethylcyclohexen-1-yl)nona-2,4,6,8-tetraenoic acid; molecular weight=300.44 g/mol).

TABLE 5

Small molecule RAR agonists

| Chemical name | Synonyms | Molecular weight (g/mol) |
| --- | --- | --- |
| (2E,4E,6E,8E)-3,7-dimethyl-9-(2,6,6-trimethylcyclohexen-1-yl)nona-2,4,6,8-tetraenoic acid | Retinoic acid, ATRA, Tretinoin, Vitamin A acid, all-trans-Retinoic acid | 300.44 |
| 4-[(E)-2-(5,6,7,8-Tetrahydro-5,5,8,8-tetramethyl-2-naphthalenyl)-1-propenyl]benzoic acid | TTNPB; Ro 13-7410 | 348.48 |
| 4-[(5,6,7,8-Tetrahydro-5,5,8,8-tetramethyl-2-naphthalenyl)carboxamido]benzoic acid | AM580 | 351.44 |
| 6-[3-(adamantyl)-4-hydroxyphenyl]-2-naphthalene carboxylic acid | CD437 | 398.49 |

The person skilled in the art will understand that an effective amount of a RAR agonist may vary depending upon, for example, the particular selected RAR agonist or combination of RAR agonist employed. In embodiments, the RAR agonist may be used in the range of 5 nM to 50 mM. In some embodiments, the RAR agonist may be used in the ranges of about 5 nM to 50 nM, 50 nM to 500 nM, 0.5 µM to 5 µM, 5 µM to 50 µM, 50 µM to 500 µM, and/or 5 mM to 50 mM. In an embodiment, retinoic acid will be provided for the culturing of the cell(s) of the present disclosure at a concentration in the range of 0.05 μM to 50 μM, or about 0.5 μM to 5 μM. Typically, the effective amount of the RAR agonist(s) will be provided in a culture medium suitable for the culture of cells of the present disclosure.

In an embodiment of the present disclosure, the method utilises an activin receptor-like kinase (ALK) receptor inhibitor as a small molecule reprogramming factor. Suitable ALK receptor inhibitors include those that inhibit, predominantly, the TGF-β type I receptor ALK5, the Activin/Nodal receptor ALK4 and the nodal receptor ALK7. Examples of inhibitors of this type are 3-(6-Methyl-2-pyridinyl)-N-phenyl-4-(4-quinolinyl)-1H-pyrazole-1-carbothioamide (also known as A83-01; molecular weight=421.52 g/mol) and 4-(5-benzol[1,3]dioxol-5-yl-4-pyridin-2-yl-1H-imidazol-2-yl)-benzamide hydrate, 4-[4-(1,3-Benzodioxol-5-yl)-5-(2-pyridinyl)-1H-imidazol-2-yl]-benzamide hydrate, 4-[4-(3,4-Methylenedioxyphenyl)-5-(2-pyridyl)-1H-imidazol-2-yl]-benzamide hydrate (also known as SB431542; molecular weight=384.4 g/mol). A83-01 strongly inhibits ALK4, 5 and 7 (IC50 values are 12, 45 and 7.5 nM respectively) and only weakly inhibits ALK1, 2, 3 and 6, and appears to inhibit TGF-β-induced EMT via the inhibition of Smad2 phosphorylation (Tojo et al., 2004). This small molecule has also been used to generate rat and human iPS cells towards a mouse ES cell like self-renewal state (Li et al 2009). Suitable ALK receptor inhibitors for use in the present disclosure may include those shown in Table 6. However, the person skilled in the art will appreciate that the list in Table 6 is not exhaustive and that other small molecule ALK receptor inhibitors may be suitable for use in the present disclosure. An example of one ALK receptor inhibitors is A83-01 (3-(6-Methyl-2-pyridinyl)-N-phenyl-4-(4-quinolinyl)-1H-pyrazole-1-carbothioamide; molecular weight=421.5).

TABLE 6

Small molecule ALK receptor inhibitors

| Chemical name | Synonyms | Molecular weight (g/mol) |
| --- | --- | --- |
| 3-(6-Methyl-2-pyridinyl)-N-phenyl-4-(4-quinolinyl)-1H-pyrazole-1-carbothioamide | A83-01 | 421.5 |
| 4-(5-benzol[1,3]dioxol-5-yl-4-pyrldin-2-yl-1H-imidazol-2-yl)-benzamide hydrate, 4-[4-(1,3-Benzodioxol-5-yl)-5-(2-pyridinyl)-1H-imidazol-2-yl]-benzamide hydrate, 4-[4-(3,4-Methylenedioxyphenyl)-5-(2-pyridyl)-1H-imidazol-2-yl]-benzamide hydrate | SB431542 | 384.4 |
| 5-chloro-N4-(2-(isopropylsulfonyl)phenyl)-N2-(2-methoxy-4-(4-(4-methylpiperazin-1-yl)piperidin-1-yl)phenyl)pyrimidine-2,4-diamin | TAE684 NVP-TAE684 | 614.2 |
| 2-(2-(1-(2-(dimethylamino)acetyl)-5-methoxyindolin-6-ylamino)-7H-pyrrolo[2,3-d]pyrimidin-4-ylamino)-6-fluoro-N-methylbenzamide | GSK1838705A | 532.57 |
| 9-ethyl-6,6-dimethyl-8-(4-morpholinopiperidin-1-yl)-11-oxo-6,11-dihydro-5H-benzo[b]carbazole-3-carbonitrile | CH5424802 | 482.62 |
| 2-(3-(6-Methylpyridine-2-yl)-1H-pyrazol-4-yl)-1,5-naphthyridine | Repsox, E-616452, SJN 2511 | 287.32 |

The person skilled in the art will understand that an effective amount of a ALK receptor inhibitor may vary depending upon, for example, the particular selected ALK receptor inhibitor or combination of ALK receptor inhibitor employed. In embodiments, the ALK receptor inhibitor may be used in the range of 5 nM to 50 mM. In some embodiments, the ALK receptor inhibitor may be used in the ranges of about 5 nM to 50 nM, 50 nM to 500 nM, 0.5 μM to 5 μM, 5 μM to 50 μM, 50 μM to 500 μM, and/or 5 mM to 50 mM. In an embodiment, A83-01 will be provided for the culturing of the cell(s) of the present disclosure at a concentration in the range of 1 nM to 1 mM, or about 0.1 μM to 100 μM, or about 1 to 10 μM. Typically, the effective amount of the ALK receptor inhibitor(s) will be provided in a culture medium suitable for the culture of cells of the present disclosure.

In an embodiment of the present disclosure, the method utilises a pancreatic and duodenal homeobox 1 (Pdx1) inducer as a small molecule reprogramming factor. Pdx1, also known as insulin promoter factor 1, is a transcription factor necessary for pancreatic development and beta cell maturation Suitable Pdx1 inducers for use in the present disclosure may include those shown in Table 7. However, the person skilled in the art will appreciate that the list in Table 7 is not exhaustive and that other small molecule Pdx1 inducers may be suitable for use in the present disclosure. An example of one Pdx1 inducer is BRD 7552 (Methyl[2,3-O-bis(Benzo[1,3]dioxol-5-yl-carbamoyl)]-4-O-(4-ethoxycarbonyl-phenylcarbamoyl)-α-D-glucopyranoside; molecular weight=711.63 g/mol).

TABLE 7

Small molecule Pdx1 inducers

| Chemical name | Synonyms | Molecular weight (g/mol) |
| --- | --- | --- |
| Methyl [2,3-O-bis(Benzo[1,3]dioxol-5-yl-carbamoyl)]-4-O-(4-ethoxycarbonyl-phenylcarbamoyl)-α-D-glucopyranoside | BRD 7552 | 711.63 |

The person skilled in the art will understand that an effective amount of a Pdx1 inducer may vary depending upon, for example, the particular selected Pdx1 inducer or combination of Pdx1 inducer employed. In embodiments, the Pdx1 inducer may be used in the range of 5 nM to 50 mM. In some embodiments, the Pdx1 inducer may be used in the ranges of about 5 nM to 50 nM, 50 nM to 500 nM, 0.5 μM to 5 μM, 5 μM to 50 μM, 50 μM to 500 μM, and/or 5 mM to 50 mM. In an embodiment, BRD 7552 will be provided for the culturing of the cell(s) of the present disclosure at a concentration in the range of 0.01 μM to 100 μM, or about 1 μM to 10 μM. Typically, the effective amount of the Pdx1 inducer(s) will be provided in a culture medium suitable for the culture of cells of the present disclosure.

In an embodiment of the present disclosure, the method utilises a mitogen-activated protein kinase kinase (MAPK/ERK kinase or MEK) inhibitor as a small molecule reprogramming factor. MEK inhibitors are compounds that target MEK so as to block the MEK (ERK 1/2) signalling pathway. Suitable MEK inhibitors for use in the present disclosure may include those shown in Table 8. However, the person skilled in the art will appreciate that the list in Table 8 is not exhaustive and that other small molecule MEK inhibitors may be suitable for use in the present disclosure. An example of one MEK inhibitor is SB 203580 (4-(4'-Fluorophenyl)-2-(4'-methylsulfinylphenyl)-5-(4'-pyridyl)-imidazole; molecular weight=377.44 g/mol).

TABLE 8

Small molecule MEK inhibitors

| Chemical name | Synonyms | Molecular weight (g/mol) |
|---|---|---|
| 4-(4'-Fluorophenyl)-2-(4'-methylsulfinylphenyl)-5-(4'-pyridyl)-imidazole | SB203580 | 377.44 |
| 2-(2-chloro-4-iodo-phenylamino)-N-cyclopropylmethoxy-3,4-difluoro-benzamide | CI-1040, PD184352 | 478.67 |
| N-(2,3-dihydroxy-propoxy)-3,4-difluoro-2-(2-fluoro-4-iodo-phenylamino)-benzamide | PD325901, PD0325901 | 482.19 |
| [3,4-difluoro-2-[(2-fluoro-4-iodophenyl)amino]phenyl][3-hydroxy-3-[(2S)-2-piperidinyl]-1-azetidinyl]methanone | GDC 0973, XL 518 | 531.31 |
| 6-(4-bromo-2-chlorophenylamino)-7-fluoro-N-(2-hydroxyethoxy)-3-methyl-3H-benzo[d]imidazole-5-carboxamide | AZD6244, Selumetinib, ARRY-142886 | 457.68 |
| (2Z,3Z)-2,3-bis(amino-2-aminophenylthio)methylene)succinonitrile,ethanol | U0126-EtOH, UO126 EtOH, | 426.56 |
| N-(3-(3-cyclopropyl-5-(2-fluoro-4-iodophenylamino)-6,8-dimethyl-2,4,7-trioxo-3,4,6,7-tetrahydropyrido[4,3-d]pyrimidin-1(2H)-yl)phenyl)acetamide | GSK1120212, Trametinib | 615.39 |
| (R)—N-(3,4-difluoro-2-(2-fluoro-4-iodophenylamino)-6-methoxyphenyl)-1-(2,3-dihydroxypropyl)cyclopropane-1-sulfonamide | RDEA119, Refametinib, BAY 869766 | 572.33 |
| 5-bromo-N-(2,3-dihydroxypropoxy)-3,4-difluoro-2-(2-fluoro-4-iodophenylamino)benzamide | PD318088 | 561.09 |
| (S)—N-(2,3-dihydroxypropyl)-3-(2-fluoro-4-iodophenylamino)isonicotinamide | AS703026 | 431.20 |
| 2-(2-fluoro-4-iodophenylamino)-N-(2-hydroxyethoxy)-1,5-dimethyl-6-oxo-1,6-dihydropyridine-3-carboxamide | AZD8330 | 461.23 |
| (R)-3-(2,3-dihydroxypropyl)-6-fluoro-5-(2-fluoro-4-iodophenylamino)-8-methylpyrido[2,3-d]pyrimidine-4,7(3H,8H)-dione | TAK-733 | 504.23 |
| 3,4-difluoro-2-((2-fluoro-4-iodophenyl)amino)-N-(2-hydroxyethoxy)-5-((3-oxo-1,2-oxazinan-2-yl)methyl)benzamide | CH4987655, RO4987655 | 565.28 |
| 5-[(4-Bromo-2-fluorophenyl)amino]-4-fluoro-N-(2-hydroxyethoxy)-1-methyl-1H-benzimidazole-6-carboxamide | ARRY-162, MEK-162, ARRY-438162 | 441.23 |
| 2-(2-amino-3-methoxyphenyl)-4H-chromen-4-one; or 2'-Amino-3'-methoxyflavone | PD98059, CAS 167869-21-8 | 267.28 |
| (Z)-3-amino-3-(2-aminophenyl)sulfanyl-2-[3-[hydroxy(pyridin-4-yl)methyl]phenyl]prop-2-enenitrile | CHEMBL37493, CHEBI: 151234, HMS3229K14, CAS 297744-42-4 | 374.45 |
| 2-Chloro-3-(N-succinimidyl)-1,4-naphthoquinone | CAS 623163-52-0 | 289.67 |
| N-Cyclopropylmethoxy-3,4,5-trifluoro-2-(4-iodo-2-methylphenylamino)benzamide | CAS 212631-61-3 | 476.2 |
| 2-(2-Chloro-4-iodo-phenylamino)-N-cyclopropylmethoxy-3,4-difluoro-5-bromo-benzamide | CAS 212631-67-9 | 557.6 |
| 1,4-Diamino-2,3-dicyano-1,4-bis(2-aminophenylthio)butadiene | U0126, CAS 109511-58-2 | 403.5 |
| E-α-(Amino-((4-aminophenyl)thio)methylene)-2-(trifluoromethyl)benzeneacetonitrile | CAS 305350-87-2 | 335.4 |

The person skilled in the art will understand that an effective amount of a MEK inhibitor may vary depending upon, for example, the particular selected MEK inhibitor or combination of MEK inhibitor employed. In embodiments, the MEK inhibitor may be used in the range of 5 nM to 50 mM. In some embodiments, the MEK inhibitor may be used in the ranges of about 5 nM to 50 nM, 50 nM to 500 nM, 0.5 µM to 5 µM, 5 µM to 50 µM, 50 µM to 500 µM, and/or 5 mM to 50 mM. In an embodiment, SB 203580 will be provided for the culturing of the cell(s) of the present disclosure at a concentration in the range of 0.1 µM to 100 µM, or about 1 µM to 10 µM. Typically, the effective amount of the MEK inhibitor(s) will be provided in a culture medium suitable for the culture of cells of the present disclosure.

In an embodiment of the present disclosure, the method utilises a notch inhibitor as a small molecule reprogramming factor. Suitable notch inhibitors for use in the present disclosure may include those shown in Table 9. However, the person skilled in the art will appreciate that the list in Table 9 is not exhaustive and that other small molecule notch inhibitors may be suitable for use in the present disclosure. An example of one notch inhibitor is DAPT (N-[(3,5-

Difluorophenyl)acetyl]-L-alanyl-2-phenyl]glycine-1,1-dimethylethyl ester; molecular weight=300.44 g/mol). DAPT also blocks Notch signalling.

TABLE 9

Small molecule notch inhibitors

| Chemical name | Synonyms | Molecular weight (g/mol) |
|---|---|---|
| N-[(3,5-Difluorophenyl)acetyl]-L-alanyl-2-phenyl]glycine-1,1-dimethylethyl ester | DAPT | 432.46 |
| N-[(1S)-2-[[(7S)-6,7-Dihydro-5-methyl-6-oxo-5H-dibenz[b,d]azepin-7-yl]amino]-1-methyl-2-oxoethyl]-3,5-difluorobenzeneacetamide | DBZ | 463.48 |
| (5S)-(tert-Butoxycarbonylamino)-6-phenyl-(4R)-hydroxy-(2R)-benzylhexanoyl)-L-leucy-L-phenylalaninamide | L-685,458 | 672.85 |
| N-[cis-4-[(4-Chlorophenyl)sulfonyl]-4-(2,5-difluorophenyl)cyclohexyl]-1,1,1-trifluoromethanesulfonamide | MRK 560 | 517.92 |
| (R)-2-Fluoro-α-methyl[1,1'-biphenyl]-4-acetic acid | Flurizan, (R)-Flurbiprofen | 244.26 |

The person skilled in the art will understand that an effective amount of a notch inhibitor may vary depending upon, for example, the particular selected notch inhibitor or combination of notch inhibitor employed. In embodiments, the notch inhibitor may be used in the range of 5 nM to 50 mM. In some embodiments, the notch inhibitor may be used in the ranges of about 5 nM to 50 nM, 50 nM to 500 nM, 0.5 μM to 5 μM, 5 μM to 50 μM, 50 μM to 500 μM, and/or 5 mM to 50 mM. In an embodiment, DAPT will be provided for the culturing of the cell(s) of the present disclosure at a concentration in the range of 0.05 μM to 50 μM, or about 0.5 μM to 5 μM. Typically, the effective amount of the notch inhibitor(s) will be provided in a culture medium suitable for the culture of cells of the present disclosure.

In an embodiment of the present disclosure, the method utilises a notch inhibitor as a small molecule reprogramming factor. Suitable notch inhibitors for use in the present disclosure may include those shown in Table 9. However, the person skilled in the art will appreciate that the list in Table 9 is not exhaustive and that other small molecule notch inhibitors may be suitable for use in the present disclosure. An example of one notch inhibitors is DAPT (N-[(3,5-Difluorophenyl)acetyl]-L-alanyl-2-phenyl]glycine-1,1-dimethylethyl ester; molecular weight=300.44 g/mol). DAPT also blocks Notch signalling.

In an embodiment of the present disclosure, the method utilises a bone morphogenetic protein (BMP) inhibitor as a small molecule reprogramming factor. Suitable BMP inhibitors for use in the present disclosure may include those shown in Table 10. However, the person skilled in the art will appreciate that the list in Table 10 is not exhaustive and that other small molecule notch inhibitors may be suitable for use in the present disclosure. An example of one BMP inhibitor is Dorsomorphin (6-[4-(2-Piperidin-1-ylethoxy)phenyl]-3-pyridin-4-ylpyrazolo[1,5-a]pyrimidine; molecular weight=399.49).

TABLE 10

Small molecule bone morphogenetic protein (BMP) inhibitors

| Chemical name | Synonyms | Molecular weight (g/mol) |
|---|---|---|
| 6-[4-(2-Piperidin-1-ylethoxy)phenyl]-3-pyridin-4-ylpyrazolo[1,5-a]pyrimidine | Dorsomorphin, AMPK Inhibitor, Compound C | 399.49 |
| 6-[4-[2-(1-Piperidinyl)ethoxy]phenyl]-3-(4-pyridinyl)-pyrazolo[1,5-a]pyrimidine dihydrochloride | Dorsomorphin dihydrochloride, Compound C, BML-275 | 472.41 |
| 4-[6-[4-(1-Methylethoxy)phenyl]pyrazolo[1,5-a]pyrimidin-3-yl]-quinoline | DMH-1 | 380.44 |
| 4-[6-[4-[2-(4-Morpholinyl)ethoxy]phenyl]pyrazolo[1,5-a]pyrimidin-3-yl]quinoline | DMH2 | 451.52 |
| 3-[(6-Amino-5-(3,4,5-trimethoxyphenyl)-3-pyridinyl]phenol | K 02288, K 02288a | 352.38 |

The person skilled in the art will understand that an effective amount of a BMP inhibitor may vary depending upon, for example, the particular selected BMP inhibitor or combination of BMP inhibitors employed. In embodiments, the BMP inhibitor may be used in the range of 5 nM to 50 mM. In some embodiments, the notch inhibitor may be used in the ranges of about 5 nM to 50 nM, 50 nM to 500 nM, 0.5 μM to 5 μM, 5 μM to 50 μM, 50 μM to 500 μM, and/or 5 mM to 50 mM. In an embodiment, BMP inhibitor will be provided for the culturing of the cell(s) of the present disclosure at a concentration in the range of 0.5 μM to 500 μM, or about 5 μM to 50 μM. Typically, the effective amount of the BMP inhibitor(s) will be provided in a culture medium suitable for the culture of cells of the present disclosure.

In an embodiment of the present disclosure, the method utilises the small molecule reprogramming factor triiodothyronine (T3); with the chemical name 3,3',5-Triiodo-L-thyronine, O-(4-Hydroxy-3-iodophenyl)-3,5-diiodo-L-tyrosine, also known 3,3',5 Triiodothyronine, 3,3',5-Triiodo-L-thyronine sodium salt and Liothyronine; molecular weight=650.97 g/mol), and its analogues include and reverse T3. T3 is a thyroid hormone involved with many physiological processes in the human body including growth and development, metabolism, body temperature and heart rate. T3 binds to thyroid hormone nuclear receptors, which in turn bind to response elements and activate or inhibit transcription of a variety of genes. It is believed to be associated with maturation of beta cells. The person skilled in the art will understand that an effective amount of T3 may vary depending upon, for example, the particular combination of small molecule reprogramming factor(s) inhibitors employed, and the particular cell(s) undergoing reprogramming. In embodiments, T3 may be used in the concentration range of 5 nM to 50 mM. In some embodiments, T3 may be used in a concentration ranges selected from about 5 nM to 50 nM, 50 nM to 500 nM, 0.5 µM to 5 µM, 5 µM to 50 µM, 50 µM to 500 µM, and/or 5 mM to 50 mM. In an embodiment, T3 will be provided for the culturing of the cell(s) at a concentration in the range of 5 nM µM to 0.5 mM, or 0.05 µM to 50 µM, or about 0.5 µM to 5 µM. Typically, the effective amount of T3 will be provided in a culture medium suitable for the culture of the cells of the present disclosure.

Accordingly, in an embodiment, the definitive endoderm inducer is IDE1. In an embodiment, the GSK inhibitor is lithium chloride. In an embodiment, the PKC activator is indolactam V. In an embodiment, the SSH inhibitor is cyclopamine-KAAD. In an embodiment, the RAR agonist is retinoic acid. In an embodiment, the ALK receptor inhibitor is A83-01. In an embodiment, the Pdx-1 inducer is BRD 7552. In an embodiment, the MEK inhibitor is SB2033580. In an embodiment, the notch inhibitor is DAPT. In an embodiment, the BMP inhibitor is Dorsomorphin.

In other embodiments, the small molecule reprogramming factors may be any other suitable small molecule reprogramming molecule, including, for example, a DNA methylase inhibitor such as RG108 and/or a HDAC inhibitor such as sodium butyrate. RG108 and other suitable DNA methylase inhibitors, and similarly, sodium butyrate and other HDAC inhibitors are described in detail in PCT/AU2012/001525 (WO 2013/086570), the content of which is incorporated by reference herein.

In an embodiment of the present disclosure, the primary induction medium comprising an effective amount of at least one small molecule reprogramming factor(s) selected from the group consisting of a definitive endoderm inducer, a glycogen synthase kinase 3 (GSK3) inhibitor and Vitamin C. In an embodiment, the primary induction medium comprises a definitive endoderm inducer, a glycogen synthase kinase 3 (GSK3) inhibitor and Vitamin C. In an embodiment, the primary induction medium comprises a definitive endoderm inducer. In an embodiment primary induction medium comprises a glycogen synthase kinase 3 (GSK3) inhibitor. In an embodiment, the primary induction medium comprises Vitamin C. In an embodiment, the primary induction medium comprises a definitive endoderm inducer and a glycogen synthase kinase 3 (GSK3) inhibitor. In an embodiment, the primary induction medium comprises a glycogen synthase kinase 3 (GSK3) inhibitor and Vitamin C. In an embodiment, the primary induction medium comprises a definitive endoderm inducer and Vitamin C. In embodiment, the definitive endoderm inducer is IDE1. In an embodiment, the GSK inhibitor is lithium chloride.

Accordingly, in an embodiment, the primary induction medium comprises IDE1, lithium chloride and Vitamin C. However, in one embodiment, the definitive endoderm inducer is not a small molecule. In an embodiment, the definitive endoderm inducer is Activin A or Nodal. Accordingly, in an embodiment, the primary induction medium comprises the small molecule reprogramming factor(s) selected from lithium chloride and Vitamin C, and the primary induction medium further comprises Activin A or Nodal. In an embodiment, the primary induction medium may further comprise a GSK inhibitor such as CHIR99021.

In an embodiment of the present disclosure, the secondary induction medium comprises an effective amount of at least one small molecule reprogramming factor(s) selected from the group consisting of a PKC activator, a sonic hedgehog (SSH) inhibitor, a retinoic acid receptor (RAR) agonist, Vitamin C, an activin receptor-like kinase (ALK) receptor inhibitor, and a Pdx1 inducer. In an embodiment, the secondary induction medium comprises a PKC activator, a sonic hedgehog (SSH) inhibitor, a retinoic acid receptor (RAR) agonist, Vitamin C, an activin receptor-like kinase (ALK) receptor inhibitor, a Pdx1 inducer and a bone morphogenetic protein (BMP) inhibitor. In an embodiment, the secondary induction medium comprises a PKC activator. In an embodiment, the secondary induction medium comprises a retinoic acid receptor (RAR) agonist, Vitamin C, and an activin receptor-like kinase (ALK) receptor inhibitor. In an embodiment, the secondary induction medium comprises Vitamin C and an activin receptor-like kinase (ALK) receptor inhibitor. In an embodiment, the secondary induction medium comprises a PKC activator, a sonic hedgehog (SSH) inhibitor, a retinoic acid receptor (RAR) agonist, Vitamin C, an activin receptor-like kinase (ALK) receptor inhibitor. In an embodiment, the secondary induction medium comprises a PKC activator, a sonic hedgehog (SSH) antagonist, Vitamin C, an activin receptor-like kinase (ALK) receptor inhibitor. In an embodiment, the secondary induction medium comprises Vitamin C. In an embodiment, the secondary induction medium comprises Vitamin C, a RAR agonist, a SSH inhibitor, a PKC activator and a BMP inhibitor. In an embodiment, the secondary induction medium comprises Vitamin C, the RAR agonist, and the SSH inhibitor.

Accordingly, in an embodiment, the secondary induction medium comprises Indolactam V. In an embodiment, the secondary induction medium comprises retinoic acid, Vitamin C and A83-01. In an embodiment, the secondary induction medium comprises Vitamin C and A83-01. In an embodiment, the secondary induction medium comprises indolactam V, cyclopamine-KAAD, retinoic acid, Vitamin C and A83-01. In an embodiment, the secondary induction medium comprises indolactam V, cyclopamine-KAAD, Vitamin C and A83-01. In an embodiment, the secondary induction medium comprises indolactam V, cyclopamine-KAAD, retinoic acid, Vitamin C, A83-01 and BRD7552. In an embodiment, the secondary induction medium comprises indolactam V, cyclopamine-KAAD, Vitamin C, A83-01 and BRD7552. In an embodiment, the secondary induction medium comprises Vitamin C. In an embodiment, the secondary induction medium comprises Vitamin C, RA, cyclopamine-KAAD, Indolactam V and dorsomorphin. In an embodiment, the secondary induction medium comprises Vitamin C, RA, and cyclopamine-KAAD.

In an embodiment of the present disclosure, the third induction medium comprising an effective amount of at least one small molecule reprogramming factor(s) selected from the group consisting of a mitogen-activated protein kinase kinase (MEK) inhibitor, Vitamin C and a notch inhibitor. In an embodiment, the third induction medium comprises a mitogen-activated protein kinase kinase (MEK) inhibitor, Vitamin C and a notch inhibitor. In an embodiment, the third induction medium comprises a mitogen-activated protein kinase kinase (MEK) inhibitor and Vitamin C. In an embodiment, the third induction medium comprises a mitogen-activated protein kinase kinase (MEK) inhibitor. In an embodiment, the third induction medium comprises Vitamin C. In an embodiment, the third induction medium comprises a notch inhibitor. In an embodiment, the third induction medium comprises Vitamin C, the RAR agonist, the SSH inhibitor, the notch inhibitor, the ALK receptor inhibitor, and triiodothyronine. In an embodiment, the third induction medium comprises Vitamin C, the RAR agonist, the notch inhibitor, the ALK receptor inhibitor, and triiodothyronine. In an embodiment, the third induction medium comprises Vitamin C, the ALK receptor inhibitor and triiodothyronine. In an embodiment, the third induction medium comprises Vitamin C and triiodothyronine.

Accordingly, in an embodiment, the third induction medium comprises SB203580 and Vitamin C. In an embodiment, the third induction medium comprises SB203580, Vitamin C and DAPT. In an embodiment, the third induction medium comprises Vitamin C, RA, cyclopamine-KAAD, DAPT, A83-01, and triiodothyronine. In an embodiment, the third induction medium comprises Vitamin C, RA, DAPT, A83-01, and triiodothyronine. In an embodiment, the third induction medium comprises Vitamin C, A83-01 and triiodothyronine. In an embodiment, the third induction medium comprises Vitamin C and triiodothyronine.

However, it is to be understood that the any one of the induction media may comprise any of the further small molecules as described herein, or as described in PCT/AU2012/001525 (WO 2013/086570).

In an embodiment, the urine-derived cells of the present disclosure are cells obtained from a urine sample of a normal, healthy subject. While not wanting to be bound by theory, it is thought that the urine-derived cells may originate from the urinary tract system, eg the kidneys, ureters, bladder, and/or urethra, and are frequently epithelial and/or fibroblast cells. The urine-derived cells are also referred to as "urine cells" herein. Human urine-derived cells, termed HUC herein, can be characterised by expression of human cell marker human nuclear antigen (HNA), and some cells express CD13 (a renal cell marker), and vemintin (a fibroblast cell marker) and/or E-cadherin (an epithelial cell marker). This indicates that the human urine-derived cells may be a heterogeneous mixture of cells. However, the urine-derived cells of the present disclosure may be of human or other animal origin (eg mouse, rat, rabbit, cat, dog, horse and non-human primates). In an embodiment, HUC are a heterogeneous cell preparation positive for cell markers HNA, CD13, vemintin and E-cadherin, although it will be appreciated by the person skilled in the art that not all HUC will co-express all of these cell markers.

The induced endoderm cells of the present disclosure may show a changed morphology compared to the urine-derived cells, with the majority of cells showing a more rounded morphology following the primary induction step. Further, the induced endoderm cells of the present disclosure may express cell markers Foxa2 and Sox17, which are both endoderm markers.

The induced pancreatic precursor cells of the present disclosure may express pancreatic precursor markers Pdx1 and NKX6.1, with some cells having an islet-cell like morphology. In an embodiment, the induced pancreatic precursor cells also express NGN3 and/or NKX2.2. Pdx1, NKX6.1, NGN3 and NKX2.2 are pancreatic precursor cell markers.

The induced beta cells of the present disclosure have upregulated levels of beta cell markers insulin and/or C-peptide, with some cells having an islet-cell like morphology. C-peptide and insulin are both beta cell markers. In an embodiment, the induced beta cells secret insulin.

The cells of the present disclosure may be washed following isolation from urine or any of the inducing steps using methods known to the person skilled in the art, for example, in sterile PBS; however, the person skilled in the art would appreciate that a variety of other solutions or culture media would be appropriate for washing cells.

In an embodiment, urine-derived cells are obtained from a cell pellet of a urine sample, for example, following centrifugation of the urine sample. In an embodiment, cells can then be washed and resuspended in an appropriate cell culture medium and optionally cultured in a pre-induction expansion step. Accordingly, the cells may be resuspended and cultured in any tissue culture medium suitable for culturing primary cells as would be well known to the person skilled in the art.

In an embodiment, the urine-derived cells are expanded in culture, for example, in "HUC1 medium" comprising Dulbecco's modified Eagle medium (DMEM)/F-12, 10% foetal bovine serum (FBS), penicillin/streptomycin (p/s), normacin and 50 µl of each reagent from a REGM Singlequot kit (hEGF, hydrocortisone, epinephrine, insulin, triiodothyronine, transferrin, GA-1000 (gentamicin/amphotericin)) as detailed elsewhere herein. In an embodiment, the urine-derived cells are cultured in HUC1 media for an appropriate period of time, for example, two days; however, the person skilled in the art would appreciate that other time periods would be suitable, for example, one day, three days, four days, five days, six day, seven days, eight days, nine days, ten days, etc. In an embodiment, the HUC1 media is changed daily. In an embodiment, the urine-derived cells are resuspended and cultured in "HUC2 media" comprising Renal Epithelial Basal Medium (REBM), 0.5% FBS, p/s, 50 µl of each reagent from a REGM Singlequot kit (hEGF, hydrocortisone, epinephrine, insulin, triiodothyronine, transferrin, GA-1000 (gentamicin/amphotericin)) as detailed elsewhere herein. However, the person skilled in the art will appreciate that various other media could readily replace HUC2 media for culturing urine-derived cells. In an embodiment, the urine-derived cells are cultured in HUC2 media for an appropriate period of time, for example, one day, two days, three days, four days, five days, six day, seven days, eight days, nine days, ten days, eleven days, twelve days, thirteen days, fourteen days, three weeks, four weeks etc. In an embodiment, the urine-derived cells are cultured in HUC2 media until cell colonies appear, for example, for between one day and fourteen days, or between four to eight days. In an embodiment, the HUC2 media is changed daily. In an embodiment, the urine-derived cells are initially cultured in HUC1 media, and then are cultured in HUC2 media. In an embodiment, the urine-derived cells are cultured in HUC1 media for two days, and then are cultured in HUC2 media until cell colonies appear, for example, for between four to eight days. However, other culture periods may be suitable as would be readily understood by the person skilled in the art. Additionally, the urine-derived cells may be cultured in other suitable cell culture media such as Renal Epithelial Cell Growth Medium (Lonza) or Keratinocyte serum free Medium (Life Technologies):Mouse Embryonic Fibroblast (MEF) medium (Dulbecco's Modified Eagle Medium (DMEM) containing 10% Fetal Bovine Serum (FBS) in a 1:1 ratio).

In an embodiment, the culturing of cells in each of the inducing steps and, optionally, a pre-induction expanding step, is carried out for a suitable period of time to facilitate expansion, or induction or reprogramming of the cells of the present disclosure as described elsewhere herein. As would be appreciated by the person skilled in the art, the period of time of the culturing may vary depending upon which cell type is being cultured and, in an embodiment, during the inducing steps, which reprogramming factors are being used in the method. Each of the first, second, or third period of time of the present disclosure, or optionally, the period of time of the optional pre-induction expanding step, may be independently selected from, for example, one, two, three, four, five, six, seven, eight, nine, ten, eleven, twelve, thirteen, fourteen, fifteen, sixteen, seventeen, eighteen, nineteen or twenty days. However, in some cases, a period of time may be longer as would be appreciated by the person skilled in the art, for example, approximately two weeks, three weeks, four weeks, etc. In particular, a person killed in the art will understand that under some circumstances, the length of a culture period may be altered to a certain degree, for example by one day, or two days, or three days, depending upon the length of the culture period, without greatly impacting on the outcome of the culture period. In an embodiment, the culture medium may be changed as often as required or as optimal as would be understood by the person skilled in the art. For example, the culture media may be changed daily, or every second, third, fourth, fifth, sixth, seventh, eighth, ninth, tenth, eleventh, twelfth, thirteenth, fourteenth day, etc, or may be changed approximately every three weeks, four weeks, etc. However, in an embodiment, the culture media is not changed during said period of time.

It is to be understood that each of the first, second or third periods of time described herein can optionally be split into two or more portions of time, and that different induction media maybe applied for different portions of the given period.

In an embodiment, the first period of time is six days. In an embodiment, the first period of time is seven days. In an embodiment, the first period of time is five days.

In an embodiment, the second period of time is four days. In an embodiment, the second period of time is seven days. In an embodiment, the second period of time is eight days. In an embodiment, the second period of time is nine days. In an embodiment, the second period of time is ten days. In an embodiment, the second period of time is eleven days. In an embodiment, the second period of time is twelve days.

In an embodiment, the second period of time consists of a first portion and a second portion. In an embodiment, the first portion of the second period of time comprises one day. However, the person skilled in the art will appreciate that the first portion may comprise two days, three days, four days, five days, six days, etc. Accordingly, the second portion of the second period of time may comprise the remaining balance of the second period of time. In an embodiment, the second period of time consists of a first portion and a second portion and a third portion. In an embodiment, the first portion of the second period of time comprises two days. However, the person skilled in the art will appreciate that the first portion may comprise one day, three days, four days, five days, six days, etc. In an embodiment, the second portion of the second period of time comprises two days. However, the person skilled in the art will appreciate that the second portion may comprise one day, three days, four days, five days, six days, etc. In an embodiment, the third portion of the second period of time comprises five days. However, the person skilled in the art will appreciate that the first portion may comprise one day, two days, three days, four days, five days, six days, seven days, eight days, nine days, ten days, eleven days, twelve days, etc.

In an embodiment, the second inducing step may utilise a different secondary induction medium for the first portion of the second period of time as compared to the second portion of the second period of time, and where relevant, a different secondary induction medium for the third portion of the second period of time as compared to the first or second portion of the second period of time. For example, in an embodiment, the secondary induction medium may comprise an effective amount of at least one small molecule reprogramming factor(s) selected from the group consisting of a PKC activator, a sonic hedgehog (SSH) inhibitor, a retinoic acid receptor (RAR) agonist, Vitamin C, an activin receptor-like kinase (ALK) receptor inhibitor, and a Pdx1 inducer for a first portion of the second period of time. In an embodiment, the secondary induction medium may comprise an effective amount of at least one small molecule reprogramming factor(s) selected from the group consisting of a PKC activator, a sonic hedgehog (SSH) inhibitor, Vitamin C, an activin receptor-like kinase (ALK) receptor inhibitor, and a Pdx1 inducer for a second portion of the second period of time. In an alternative example, the secondary induction medium may comprise an effective amount of Vitamin C for the first portion of the second period of time. In an embodiment, the secondary induction medium may comprise an effective amount of at least one small molecule reprogramming factor(s) selected from the group consisting of Vitamin C, a RAR agonist, a SSH inhibitor, a PKC activator and a BMP inhibitor for a second portion of the second period of time. In an embodiment, the secondary induction medium may comprise an effective amount of at least one small molecule reprogramming factor(s) selected from the group consisting of and/or Vitamin C, the RAR agonist, and the SSH inhibitor for a third portion of the second period of time. However, a secondary induction medium comprising other small molecule reprogramming factor(s) may be used for the first portion, second portion or third portion of the second period of time as described elsewhere herein.

In an embodiment, the third period of time is eight days. In an embodiment, the third period of time is nine days. In an embodiment, the third period of time is ten days. In an embodiment, the third period of time is twelve days. In an embodiment, the third period of time is fourteen days. In an embodiment, the third period of time is 21 days. In an embodiment, the third period of time is 28 days. However, the person skilled in the art will appreciate that the third period of time may comprise two days, three days, four days, five days, six days, seven days, eleven days, thirteen days, fifteen days, sixteen days, seventeen days, eighteen days, nineteen days, 20 days, 22 days, 23 days, 24 days, 25 days, 26 days, 27 days, 29 days, 30 days, five weeks etc.

In an embodiment, the third period of time consists of a first portion and a second portion. In an embodiment, the third period of time consists of a first portion, a second portion and a third portion. In an embodiment, the first portion of the third period of time comprises one day. In an embodiment, the first portion of the third period of time comprises two days. In an embodiment, the first portion of the third period of time comprises four days. However, the person skilled in the art will appreciate that the first portion may comprise three days, five days, six days, etc. Accordingly, the second portion and/or third portions of the third period of time may comprise the remaining balance of the third period of time. In an embodiment, the second portion of the third period of time comprises one day. In an embodiment, the second portion of the third period of time comprises two days. In an embodiment, the second portion of the third period of time comprises three days. In an embodiment, the second portion of the third period of time comprises four days. In an embodiment, the second portion of the third period of time comprises five days. However, the person skilled in the art will appreciate that the second portion of the third period may comprise six days, seven days, eight days etc. In an embodiment, the third portion of the third period of time comprises 14 days. However, the person skilled in the art will appreciate that the third portion of the third period may comprise one day, two days, three days, four days, six days, seven days, eight days, nine days, ten days, eleven days, twelve days, thirteen days, fifteen days, sixteen days, seventeen days, eighteen days, nineteen days, 20 days, 22 days, 23 days, 24 days, 25 days, 26 days, 27 days, 29 days, 30 days, five weeks etc.

In an embodiment, the third inducing step may utilise a different tertiary induction medium for the first portion of the third period of time as compared to the second portion of the third period of time, and where relevant, a different tertiary induction medium for the third portion of the third period of time as compared to the first or second portion of the third period of time. For example, in an embodiment, the tertiary induction medium may comprise an effective amount of at least one small molecule reprogramming factor(s) selected from the group consisting of Vitamin C, a RAR agonist, a SSH inhibitor, a notch inhibitor, the ALK receptor inhibitor, and triiodothyronine for a first portion of the third period of time. In an embodiment, the tertiary induction medium may comprise an effective amount of at least one small molecule reprogramming factor(s) selected from the group consisting of Vitamin C, the RAR agonist, the notch inhibitor, the ALK receptor inhibitor, and triiodothyronine for a second portion of the third period of time. In an embodiment, the tertiary induction medium may comprise an effective amount of at least one small molecule reprogramming factor(s) selected from the group consisting of Vitamin C, the ALK receptor inhibitor and triiodothyronine for a third portion of the third period of time. In an embodiment, the tertiary induction medium may comprise an effective amount of at least one small molecule reprogramming factor(s) selected from the group consisting of Vitamin C and triiodothyronine for a third portion of the third period of time. However, a tertiary induction medium comprising other small molecule reprogramming factor(s) may be used for the first portion, second portion or third portion of the third period of time as described elsewhere herein.

It is to be understood that the period of time of any (or all) of the induction steps of the present disclosure can varied without departing from the scope of the disclosure. Moreover, it is to be understood that any one (or all) of the period(s) of time of the induction steps can be split into portions, with a different induction medium containing a different at least one small molecule reprogramming factor(s) (or combination thereof) as described herein for a first portion of the period of time, as compared to a second portion of the period of time, and optionally, as compared to a third portion of the period of time, etc, without departing from the scope of the disclosure.

In the present disclosure, an effective amount of each of at least one small molecule reprogramming factor(s) may be added to a "base" culture media to form an induction culture media as described herein. The base culture medium used in the inducing steps and any further passaging or culturing of the induced cells of the present disclosure in suspension may be any suitable medium that will support the growth of the particular cell type such as those that will be well known to the person skilled in the art. In an embodiment, the base culture media comprises RPMI supplemented with 2% FBS. In an embodiment, the base culture media comprises DMEM, supplemented with L-glutamine and B27. In an embodiment, the base culture media comprises DMEM supplemented with progesterone, putrescine, laminin, nicotinamide, insulin, transferrin, sodium selenite and B27. In an embodiment, the base culture media comprises MCDB131 medium, supplemented with bFGF, D-Glucose, NaHCO3, BSA, Insulin-Transferrin-Selenium-Ethanolamine (ITS-X), and Glutamax (L-alanine-L-glutamine dipeptide). In an embodiment, the base culture media comprises MCDB131 medium, EGF, D-Glucose, NaHCO3, BSA, ITS-X 1:200, Glutamax and Heparin. In an embodiment, the base culture media comprises CMRL 1066 supplemented with 10% FBS. All of these media and supplements are commercially available and are well known to the person skilled in the art. However, the person skilled in the art would appreciate that various other media would be appropriate for the culture of the cells of the present disclosure, and further, various other supplements may be added to the base culture media to optimise growth of the cells without departing form the scope of the present disclosure as would be appreciated by the person skilled in the art.

In an embodiment, the base culture medium used in the primary induction culture media is RPMI supplemented with 2% FBS. However, other culture media may be appropriate as a base culture media for inducing urine-derived cells to be endoderm-like cells as would be appreciated by the person skilled in the art. In an embodiment, the base culture medium used in the secondary induction culture media is DMEM, supplemented with L-glutamine and B27. In an embodiment, the base culture medium used in the secondary induction culture media is MCDB131 medium, supplemented with bFGF, D-Glucose, NaHCO3, BSA, Insulin-Transferrin-Selenium-Ethanolamine (ITS-X), and Glutamax (L-alanine-L-glutamine dipeptide). However, other culture media may be appropriate as a base culture media for inducing endoderm-like cells to be pancreatic precursor-like cells as would be appreciated by the person skilled in the art. In an embodiment, the base culture medium used in the tertiary induction culture media is DMEM supplemented with progesterone, putrescine, laminin, nicotinamide, insulin, transferrin, sodium selenite and B27. In an embodiment, the base culture medium used in the tertiary induction culture media is MCDB131 medium, EGF, D-Glucose, NaHCO3, BSA, ITS-X 1:200, Glutamax and Heparin. In an embodiment, the base culture medium used in the tertiary induction culture media is CMRL 1066 supplemented with 10% FBS. However, other culture media such as may be appropriate for inducing pancreatic precursor-like cells to be beta-like cells as would be appreciated by the person skilled in the art.

In an embodiment of the present disclosure, the obtained induced beta cells are cultured in a tertiary induction culture medium as described herein. However, other culture media may be appropriate for culturing the induced beta cells as would be appreciated by a person skilled in the art.

In an embodiment, each step of inducing of the cell(s) of the present disclosure in the presence of at least one small molecule reprogramming factor(s) may optionally be independently conducted in a single induction culture cycle, comprising, for example, a first culture of the cell(s) in a culture medium comprising the at least one small molecule reprogramming factor(s) or combination thereof, followed by at least a second culture in the same or different suitable culture medium lacking the at least one small molecule reprogramming factor(s) or combination thereof. In an embodiment, the induction cycle comprises a first culture in the presence of at least one small molecule reprogramming factor(s) as mentioned above, followed by second and third cultures in a culture medium lacking the small molecule reprogramming factor(s). It is to be understood that each of these induction cycles can optionally be repeated as necessary.

The induced beta cells of the present disclosure may advantageously be used to produce insulin. Indeed, it may ultimately be possible to use the induced beta cells of the present disclosure in method of personalised cellular therapy for treating diseases associated with insulin deficiency such as diabetes. Alternatively, the induced beta cells of the present disclosure may advantageously be used to screen drug candidates for treating diabetes. The person skilled in the art will appreciate that the induced beta cells of the present disclosure may also have other uses.

In a second aspect, the present disclosure provides a method of producing an induced endoderm cell from a urine-derived cell, the method comprising:
  (a) obtaining urine-derived cells from a urine sample of a subject; and
  (b) inducing the urine-derived cells obtained in step (a) by culturing said urine-derived cells in a primary induction culture medium comprising an effective amount of at least one small molecule reprogramming factor(s) for a first period of time to obtain induced endoderm cells.

The induced endoderm cells of the present disclosure may advantageously be transdifferentiated into pancreatic, hepatic, intestinal and/or pulmonary cell lineages.

In an embodiment, the method comprises a further step of inducing the obtained induced endoderm cells to pancreatic precursor cells using any method known to those skilled in the art. For example, the endoderm cells may be induced to become induced pancreatic precursor cells using the method described in D'Amour et al. (2006), Li et al. (2014) or Pagliuca et al. (2014).

In an embodiment, the method comprises a further step of inducing the obtained induced endoderm cells to become induced pancreatic precursor cells using any method known to those skilled in the art, and comprise a yet still further step of inducing the induced pancreatic precursor cells to become induced beta cells using any method known to the person skilled in the art. For example, the endoderm cells may be induced to become induced pancreatic precursor cells using the method described in beta cells using any method known to the person skilled in the art. For example, the induced endoderm cells may be induced to become induced beta cells using the method described in D'Amour et al. (2006), Li et al. (2014) or Pagliuca et al. (2014).

In a third aspect, the present disclosure provides a method of producing an induced pancreatic precursor cell from a urine-derived cell, the method comprising:
  (a) obtaining urine-derived cells from a urine sample of a subject;
  (b) inducing the urine-derived cells obtained in step (a) by culturing said urine-derived cells in a primary induction culture medium as described herein to obtain induced endoderm cells; and
  (c) inducing the induced endoderm cells obtained in step (b) by culturing said induced endoderm cells in a secondary induction culture medium as described herein to obtain induced pancreatic precursor cells.

The induced pancreatic-precursor cells of the present disclosure may advantageously be used to, for example, generate functional islet cell clusters or potentially an artificial pancreas for treatment of disease such as Type I or Type II diabetes or gene therapy applications. The induced pancreatic precursor cells of the present disclosure could alternatively be used to facilitate research on pancreatic precursor cell biology and/or differentiation, and/or for drug development and discovery.

In an embodiment, the method comprises a further step of inducing the obtained induced pancreatic precursor cells to become induced beta cells using any method known to those skilled in the art. For example, the induced endoderm cells may be induced to become induced beta cells using the method described in D'Amour et al. (2006), Li et al. (2014) or Pagliuca et al. (2014).

In a fourth aspect, the present disclosure provides a method of producing an induced pancreatic precursor cell from an endoderm cell, the method comprising:
  obtaining endoderm cells; and
  inducing the obtained endoderm cells by culturing said endoderm cells in a secondary induction medium as described herein to obtain induced pancreatic precursor cells.

In an embodiment, the endoderm cells may be obtained following isolation from a subject, or they may be induced by any means known to the person skilled in the art.

In a fifth aspect, the present disclosure provides a method of producing an induced beta cell from a pancreatic precursor cell, the method comprising:
  obtaining pancreatic precursor cells; and
  inducing the obtained pancreatic precursor cells by culturing said pancreatic precursor cells in a tertiary induction medium as described herein for a period of time to obtain induced beta cells.

In an embodiment, the pancreatic precursor cells may be obtained following isolation from a subject, or they may be induced by any means known to the person skilled in the art.

The method of the second, third, fourth and fifth aspects may be performed using the embodiments as described herein for the first aspect of the disclosure, as appropriate.

In a sixth aspect, the present disclosure provides the cells obtained using the method of the first, second, third, fourth or fifth aspects of the present disclosure.

The disclosure will hereinafter be described with reference to the following non-limiting examples and accompanying figures.

EXAMPLES

Example 1 Isolation and Characterisation of Human Urine Cells (HUC)

Materials and Methods
  Media
    HUC1 media—50 ml of HUC1 contained 44.15 ml Dulbecco's modified Eagle medium (DMEM)/F-12 (Invitrogen Cat No 15140-122), 5 ml foetal bovine serum (FBS; Life Technologies), 0.5 ml penicillin/streptomycin (p/s; 50 units/ml penicillin, 50 µg/ml streptomycin, 100 µl 50 µg/ml normacin (InvivoGen Cat No. ant-nr-2) and 50 µl of each reagent from a REGM Singlequot kit (Lonza Cat. No. CC-4127; that is, hEGF, hydrocortisone, epinephrine, insulin, triiodothyronine, transferrin, GA-1000 (which contains 30 mg/ml gentamicin and 15 μg/ml amphotericin), and FBS).

HUC2 media—50 ml of HUC2 media contains 48.95 ml Renal Epithelial Basal Medium (REBM; no growth factors) (Lonza Cat No CC-3191), 0.25 ml FBS, 0.5 ml p/s, 100 μl 50 μg/ml nonnacin, and 50 μl of each of the seven Singlequot kit reagents as described above.

Isolation and Initial Pre-Induction Culture of Human Urine Cells

Urine samples were collected from a 35 year old human male donor ("M-35") and a 37 year old human female donor ("F-37"), with the volume of samples typically of 150-200 ml. The samples were then transferred into 50 ml tubes and centrifuged at 400 g for 10 minutes at room temperature. The supernatant was then carefully discarded, leaving approximately 1 ml or less of urine in the tube. Pellets containing human urine cells (HUC) were individually resuspended and all of the resuspended pellets originating from the same sample collection were pooled into a single 50 ml tube. Next, about 10 ml of phosphate buffered saline (PBS) containing normacin and penicillin/streptomycin were added as described above to prevent growth of contaminant fungi or facultative bacteria residing in the urethra. Then, the samples were again centrifuged at 400 g for 10 minutes, and the supernatant carefully discarded, thereby leaving only about 0.2 ml of sample. To the residual sample, about 1 ml of HUC1 medium was added to resuspend the cell pellet. An aliquot of approximately 0.25 ml of the cells were then seeded into each well of a 4 well plate (Nunc) which were previously coated with 0.1% gelatin Sigma-Aldrich); incubated for 30 min at 37° C.) and cultured at 37° C. for day 1 (D1) and day 2 (D2). On day 3 (D3), the HUC1 media was replaced with HUC2 media, and changed daily (with HUC2 media) thereafter until cell colonies appeared (typically four to eight days).

Immunocytochemistry (ICC)

Cells from the colonies were washed with PBS and fixed with 4% paraformaldehyde for 10 min. After a further washing (2×) with PBS, the fixed cells were then permeabilised with 0.1% Triton X-100 for 20 min. The permeabilised cells were then washed twice with PBS and blocked in a solution of PBS containing 1% FBS and 4% bovine serum albumin (BSA) for 1 hour. Primary antibodies (as shown in Table 11) were diluted in blocking buffer and applied for 1 hour at room temperature or overnight at 4° C. The cells were then washed three times with PBS and the appropriate fluorescent secondary antibodies (1:1000, Cy3 or Alexa-488, see Table 12) applied with 10 μg/ml 4',6-diamidino-2-phenylindole (DAPI) fluorescent dye for 1 hour at room temperature.

TABLE 11

Primary antibodies used in immunocytochemistry

| Antibody against | Source | Catalogue number | Dilution | Species | Reactivity species |
|---|---|---|---|---|---|
| Sox17 | R&D Systems | AF1924 | 1:200 | goat | human |
| Foxa2 | Millipore | 07-633 | 1:200 | rabbit | mouse/human/rat |
| PDX1 | Cell Signaling Technology | 5679 | 1:400 | rabbit | human/rat |
| NKX6.1 | Developmental Studies Hybridoma Bank (DSHB) | F55A12 | 1:100 | mouse | mouse/human/rat |
| NGN3 | DSHB | F25A1B3 | 1:100 | mouse | mouse/human |
| Insulin | Cell Signaling Technology | 3014S | 1:100 | rabbit | mouse/human/rat |
| C-peptide | DSHB | GN-ID4 | 1:500 | rat | human/monkey |
| CD13 | GeneTex-Sapphire Bio | EPR4058 | 1:500 | rabbit | mouse/rat/human |
| HNA | millipore | MAB1281 | 1:100 | mouse | human |
| Vemintin | Santa cruz | sc-6260 | 1:100 | mouse | rat/human |
| E-cadherin | BD biosciences | 610181 | 1:500 | mouse | mouse/rat/human |

TABLE 12

Secondary antibodies used in immunocytochemistry

| Name | Catalogue number | Source |
|---|---|---|
| Donkey Anti-Mouse IgG 488 | 715-225-150 | Jackson ImmunoResearch Laboratories |
| Donkey Anti-Mouse IgG cy3 | 715-225-152 | Jackson ImmunoResearch Laboratories |
| Donkey Anti-Rabbit IgG 488 | 711-225-152 | Jackson ImmunoResearch Laboratories |
| Donkey Anti-Rabbit IgG cy3 | 711-165-152 | Jackson ImmunoResearch Laboratories |
| Donkey Anti-Sheep IgG 488 | 713-225-147 | Jackson ImmunoResearch Laboratories |
| Donkey Anti-Sheep IgG cy3 | 713-225-147 | Jackson ImmunoResearch Laboratories |

Characterisation of HUC

Cellular expression of human nuclear antigen (HNA; a human cell marker), CD13 (a renal tubular cell marker), vemintin (a fibroblast marker), and E-cadherin (an epithelial cell marker), were examined by ICC as described above.

Results and Discussion

Figures 2A, 2B:
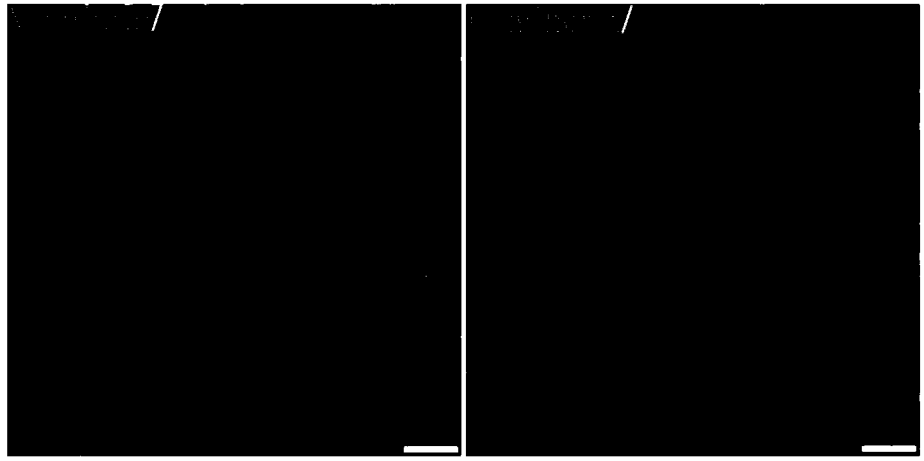
FIG. 2 provides fluorescent micrograph images of human urine cells (HUC) collected from a 35 year old human male donor ("M-35") stained for (a) vemintin, and (b) E cadherin, scale bar=100 μm.

Cells were isolated from human urine samples and characterised. The results are shown in FIG. 1. In particular, FIG. 1 shows that the HUC-M-35 cells were HNA positive (confirming that the cells are of human origin), and that some were positive for CD13 (indicating that at least some of the cells are renal cells). It was also found that many of the HUC-M-35 cells expressed the fibroblast marker vemintin and some cells expressed the epithelial marker E-cadherin (FIG. 2); this indicates that the HUC-M-35 culture contains a mixture cells. Similarly, the HUC-F-37 cells at P6 were CD13 positive, HNA positive, E-cadherin positive and vimentin positive.

Example 2 Characterisation of Cells Following Primary Induction with Activin A, Lithium Chloride and Vitamin C Materials and Methods
Primary Induction
HUC-M-35 P5 cells were prepared as described in Example 1 and then cultured on matri-gel coated wells (Geltrex™ LDEV-Free, hESC-Qualified, A1413302, Life Technologies) at a density of $5 \times 10^4/cm^2$ in primary induction media containing RPMI 1640 Medium (Life Technologies, Cat No. 11875-085), 0.2% FBS, 100 ng/ml Activin A (Recombinant Human/Mouse/Rat Activin A, 338-AC-010, R&D systems), 1 mM LiCl (Sigma-Aldrich Pty. Ltd, Cat No. L4408), 0.2 mM Vitamin C (Sigma-Aldrich Pty. Ltd, Cat No. A4403) and p/s (as described above) for six days (changed every second day). The cultured cells were then characterised; specifically, cell morphology was examined by phase contrast microscopy, and expression of Foxa2 (an endoderm cell marker) and Sox17 (an endoderm cell marker) compared by ICC prior to and following the primary induction.

Figures 3A, 3B:
FIG. 3 provides micrograph images of cells collected from the urine of a 35 year old human male donor ("M-35") (a) prior to and (b) following primary induction with primary induction media containing Activin A, LiCl, and Vitamin C for 6 days, scale bar: 100 μm.
Figure 4A:
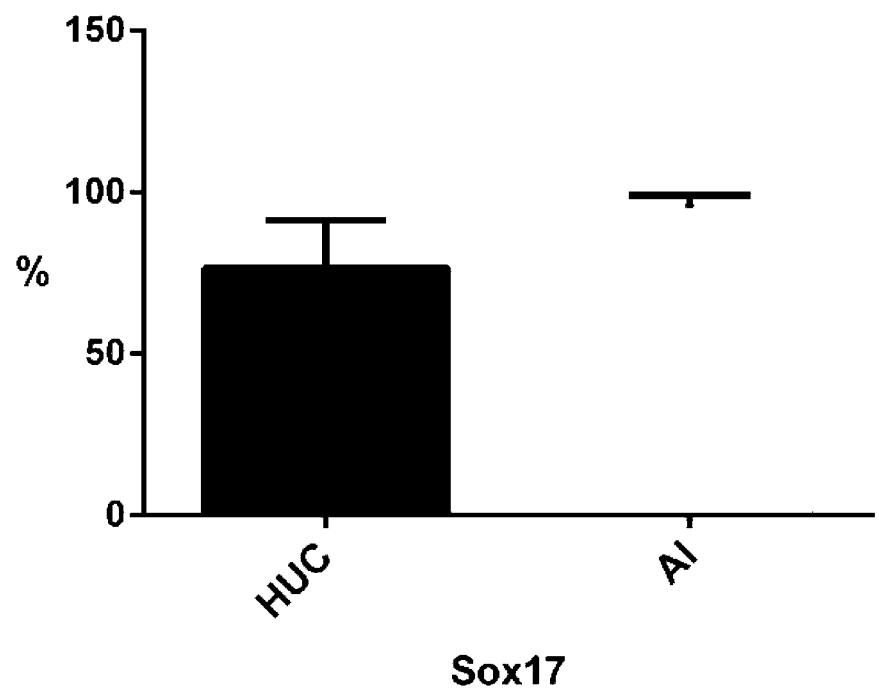
FIG. 4 provides graphical results of percentage of cells collected from the urine of a 35 year old human male donor ("M-35") positive for (a) Sox17 and (b) Foxa2 prior to (first column) and following (second column) primary induction with primary induction media containing Activin A, LiCl, and Vitamin C for 6 days (AI=after induction)
Figure 4B:
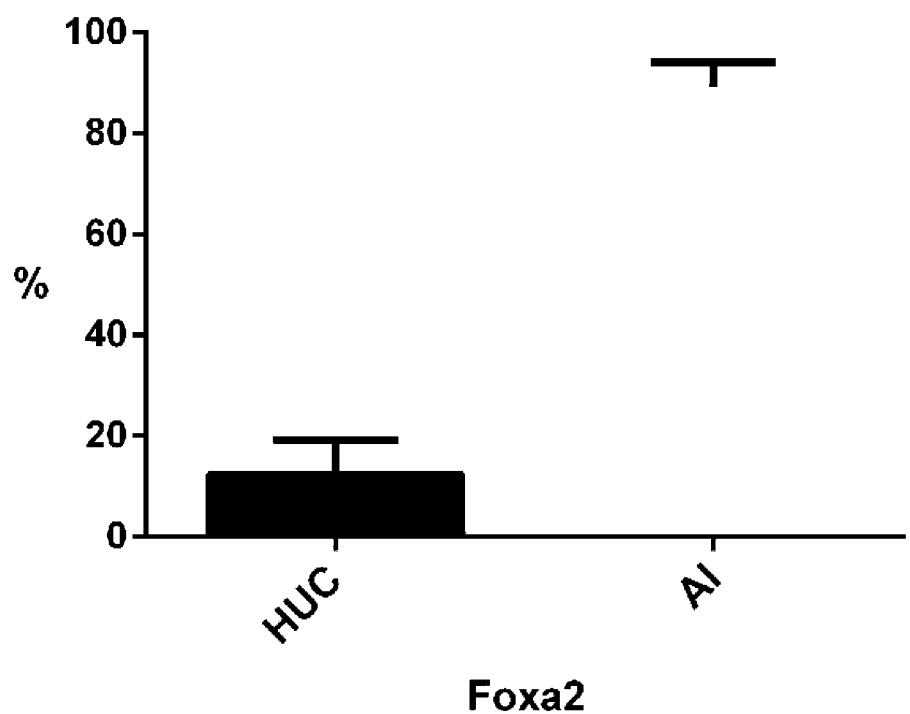

Results and Discussion
HUC-M-35 P5 cells were cultured in a primary induction media as described above. It was found that the cell morphology changed markedly (see FIG. 3 which compares the morphology of HUC-M-35 derived cells at P6 with the same cells following the primary induction), indicating that the cells are no longer urine cells. Specifically, prior to induction, the urine cells comprised a mixture of cells, some had a rounded morphology, some had a multi-angled morphology and some had spindle-shaped morphology. After the primary induction step, the morphology of most of the cells was rounded. From fluorescent micrographs of the HUC-M-35 derived cells prior to and following primary induction, it was found that both types of cells are positive for the endoderm markers Sox17 and Foxa2. However, the number of Sox17/Foxa2 positive cells is markedly increased following the primary induction, indicating that these markers are upregulated by the primary induction protocol. FIG. 4 shows that the primary induction protocol facilitates an increase in expression of Sox17 from approximately 75% of the cells to approximately 95% cells, and an increase in Foxa2 expression from approximately 12% to approximately 89%. The results indicate that the primary induction step induces the human urine cells to endoderm cells.

Example 3 Characterisation of Cells Following Primary Induction with Activin a, Lithium Chloride, Vitamin C, ChIR99201, Forskolin, Sodium Butyrate and RG108

Materials and Methods
Primary Induction
HUC-M-35 P5 cells were prepared as described in Example 1, and then induced using the primary induction method described in Example 2, except that in addition to the contents of the primary induction media described in that example, the primary induction media in this case included the small molecules ChIR99201 (CH; 3 µM), forskolin (F; 10 µM), sodium butyrate (NaB; 0.2 mM) and RG108 (RG; 0.04 µM) (all sourced from Stemgent, Inc). Additionally, the primary induction step was carried out for seven days rather than six days. A comparative induction where the primary induction media lacked the small molecules was also undertaken. Foxa2 expression of cells was examined prior to and after the primary induction step as described in Example 2.

Results and Discussion
After seven days in the primary induction media containing Activin A, lithium chloride and Vitamin C as described in Example 2, 91.8% of cells were positive for Foxa2. When the primary induction media included the small molecules CH, F, NaB and RG, 88.5% of cells were Fox2a positive. This result indicates that the additional small molecules ChIR99201, forskolin, sodium butyrate and RG108, in the tested combination, inhibit the induction of endoderm cells from urine cells.

Example 4 Characterisation of Cells Following Secondary Induction with Indolactam V Materials and Methods
Secondary Induction
HUC-M-35 P5 cells were prepared using the primary induction protocol described in Example 2. The cells were then cultured in a secondary induction medium containing DMEM, 330 nm Indolactam V, 1×2 mM L-glutamine (Life Technologies, Cat No. 25030-081), and 1×B27 (Life Technologies, Cat No. 17504044) and p/s as detailed above for four days. The morphology of the resultant cells was examined by phase contrast microscopy.

Results and Discussion
Following the secondary induction, most cells were observed to have a rounded morphology and some cells appeared to have an islet cell morphology.

Example 5 Characterisation of Cells Following Secondary Induction Using Indolactam V, Retinoic Acid, Vitamin C and A83-01

Materials and Methods
Secondary Induction
HUC-M-35 P5 cells were induced using the primary induction protocol described in Example 2. The cells were then cultured in the secondary induction medium described in Example 4 with, additionally, 2 µM retinoic acid (RA), 0.2 mM Vitamin C (VC) and 2.5 mM A83-01 for one (1) day and then 0.2 mM Vitamin C, and 2.5 µM A83-01 for seven days. The morphology of the resultant cells was assessed by phase contrast microscopy.

Results and Discussion
The morphology of the typical resultant cells is shown in FIGS. 5A and 5B. Following the secondary induction protocol, cells with an islet-like morphology were clearly observed, with different types of islet morphology visible

Example 6 Characterisation of Cell Infected with Pdx1-Cy3-Insulin-488 Lentivirus Following Secondary Induction Materials and Methods
Lentivirus Infection
The Pdx1-cy3-insulin-488 lentivirus (Szabat et al., 2009) encodes insulin fused to a fluorescent marker (Cy3) under the control of the Pdx1 promoter. HUC were induced as described in Example 5 and were then infected by culturing the cells in the presence of 50 µL of the Pdx1-cy3-insulin-488 lentivirus for 24 hours in DMEM containing 10 mg/ml polybrene.

Results and Discussion
Pdx1 is a pancreatic transcription factor and is, accordingly, a pancreatic cell marker. As shown in FIG. 6, cells induced in this Example have islet cell morphology. Moreover, FIG. 6B shows strong fluorescent staining, indicating that the Pdx promoter is active in the cells and drives expression of the lentivirus expressed insulin-488 fusion gene. This indicates the cells are pancreatic-like.

Example 7 Characterisation of Cells Following Secondary Induction with Indolactam V Materials and Methods
Primary and Secondary Induction
Cells were prepared as described in Example 1 and then underwent primary induction as described in Example 2 followed by secondary induction as described in Example 5. Cells were then characterised as described in Example 1. Specifically, cell morphology was examined by phase contrast microscopy, and expression of NKX6.1 (pancreatic precursor cell marker) and PDX1 (pancreatic precursor cell marker) were examined.
Results and Discussion
The resultant cells were observed to express the pancreatic precursor markers PDX1 and NKX6.1. This again indicates that the cells are pancreatic-like.

Figure 7:
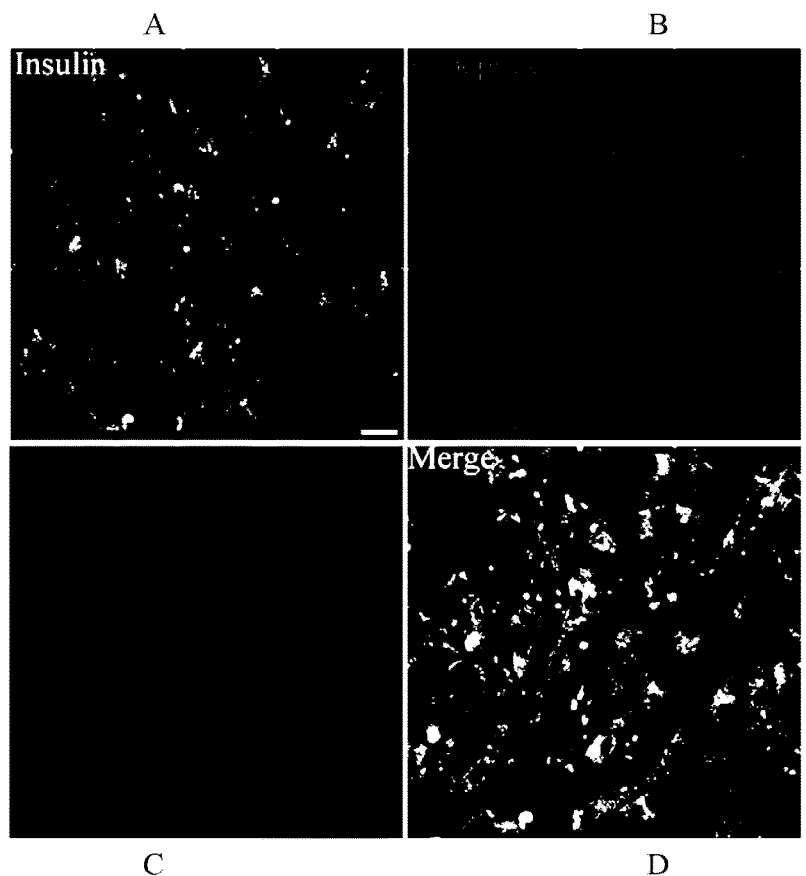
FIG. 7 provides fluorescent micrograph images of cells, collected from human urine, following primary induction with primary induction media containing Activin A, LiCl, and Vitamin C for 6 days, secondary induction in secondary induction media containing Indolactam V, RA, Vitamin C, and A83-01 for one day, and then Indolactam V, Vitamin C, A83-01 for 3 days, and tertiary induction with tertiary induction media containing SB203580 and Vitamin C for nine days, scale bar=100 μm.

Example 8 Characterisation of Cells Following Tertiary Induction with SB203580 and Vitamin C Materials and Methods
Tertiary Induction
Cells were prepared as described in Example 1 and then underwent primary induction as described in Example 2 followed by secondary induction as described in Example 5. Afterwards, the cells were then cultured in a tertiary induction medium containing DMEM, 20 nm progesterone, 100 μm putrescine (Sigma-Aldrich Pty Ltd, Cat No P-5780), 1 μg/ml laminin (Sigma-Aldrich, Cat No L2020-1MG), 10 mm nicotinamide (Sigma-Aldrich, Cat No N-3376), 25 μg/ml insulin (Sigma-Aldrich, Cat No 1-1882), 50 μg/ml transferrin (Sigma-Aldrich, Cat No T-1147), 30 nM sodium selenite (Sigma-Aldrich, Cat No S-5261), 1×B27, 5 μm SB203580 (Sigma-Aldrich, Cat No S8307) and 0.2 mM Vitamin C and p/s (as detailed above) for nine days. Cells were characterised by examining expression of insulin (beta cell marker) and C-peptide (beta cell marker).
Results and Discussion
Among the resultant cells, some were clearly expressing beta cell markers insulin (41% of the cells) and some were expressing C-peptide (36.5% of the cells) (FIG. 7). These results indicate that the cells are now beta-like.

Example 9 Characterisation of Cells Following Alternative Primary Induction with IDE1 Replacing Activin A Materials and Methods
Primary Induction
HUC-M-35 and HUC-F-35 cells were isolated and cultured and underwent a primary induction as described in Example 2, except that the primary induction media substituted inducer definite endoderm IDE1 (Borowiak et al., 2009) for Activin A. That is, the primary induction medium contained RPMI 1640 Medium, 0.2% FBS, 100 μM IDE1 (Jomar Bioscience Pty Ltd, Cat No 4015), 1 mM LiCl, and 0.2 mM Vitamin C. The cells were cultured in this medium for six days. Induced cells were assessed for the expression of the endoderm cell markers, Foxa2 and Sox17.
Results and Discussion
It was found that 100% of cells derived from HUC1-M-35 and HUC-F-35 cells respectively, expressed Foxa2 and Sox17. This indicates that the primary induction protocol using IDE1 instead of Activin A successfully induces the cells to become endoderm-like.

Example 10 Characterisation of Cells Following Alternative Secondary Induction with Cyclopamine-KAAD, Indolactam V, Retinoic Acid, Vitamin C, A83-01 and BRD 7552 Initially, Followed by Cyclopamine-KAAD, Indolactam V, Vitamin C, A83-01 and BRD 7552

Materials and Methods
Secondary Induction A
HUC-M-35 cells were induced using the primary induction protocol described in Example 9. Then, the cells were cultured in a secondary induction medium containing DMEM, 0.25 μM cyclopamine-KAAD (Sapphire Bioscience Pty Ltd, Cat No ab142146), 330 nm Indolactam V, 1×2 mM L-glutamine, 1×B27, 2 μM retinoic acid (RA), 0.2 mM Vitamin C (VC), 2.5 μM A83-01, and 5 μM BRD 7552, with pH adjusted to 7.4, for one day. Following this, the cells were cultured in another secondary induction medium containing DMEM, 0.25 μM cyclopamine-KAAD, 330 nm Indolactam V, 1× L-glutamine, 1×B27, 0.2 mM Vitamin C, 2.5 μM A83-01, and 5 μM BRD 7552, with pH adjusted to 7.4, for three days. Cells were characterised by expression of Nkx6.1 and PDx1 using ICC.
Secondary Induction B
In an alternative experiment, cells were induced using the primary induction protocol described in Example 9. Then, the cells were cultured in a secondary induction medium containing DMEM, 0.25 μM cyclopamine-KAAD, 330 nm Indolactam V, 1×2 mM L-glutamine, 1×B27, 2 μM retinoic acid (RA), 0.2 mM Vitamin C (VC), 2.5 μM A83-01, and 5 μM BRD 7552, with pH adjusted to 7.4, for one day. Then, the cells were cultured in another secondary induction medium containing DMEM, 0.25 μM cyclopamine-KAAD, 330 nm Indolactam V, 1× L-glutamine, 1×B27, 0.2 mM Vitamin C, 2.5 μM A83-01, and 5 μM BRD 7552, with pH adjusted to 7.4, for six days.
Results and Discussion
The resultant cells from both secondary Induction protocols expressed the pancreatic precursor markers NKx6.1 and Pdx1. This indicates that the cells derived from human urine cells are pancreatic-like following primary induction and secondary induction as described, when the secondary induction protocol includes cyclopamine-KAAD.

Figures 8A, 8B, 8C:
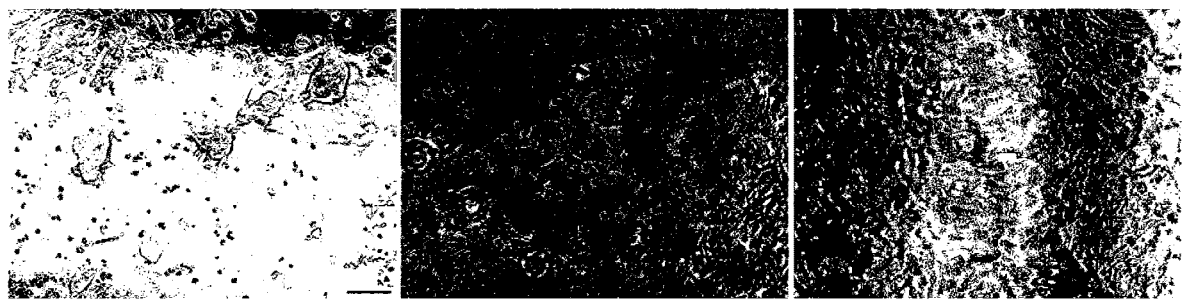
FIG. 8 provides phase contrast images of cells, collected from human urine, following primary induction with primary induction media containing inducer of definitive endoderm (IDE) 1, Lithium chloride and Vitamin C for six days, secondary induction in secondary induction media containing cyclopamine-KAAD, Indolactam V, RA, Vitamin C, A83-01 and BRD 7552 (pH adjusted to 7.4) for one day and then cyclopamine-KAAD, Indolactam V, Vitamin C, A83-01 and BRD 7552 for six days (pH adjusted to 7.4), and tertiary induction with tertiary induction media containing SB203580, Vitamin C and DAPT for nine days, scale bar=100 μm.
Figure 9:
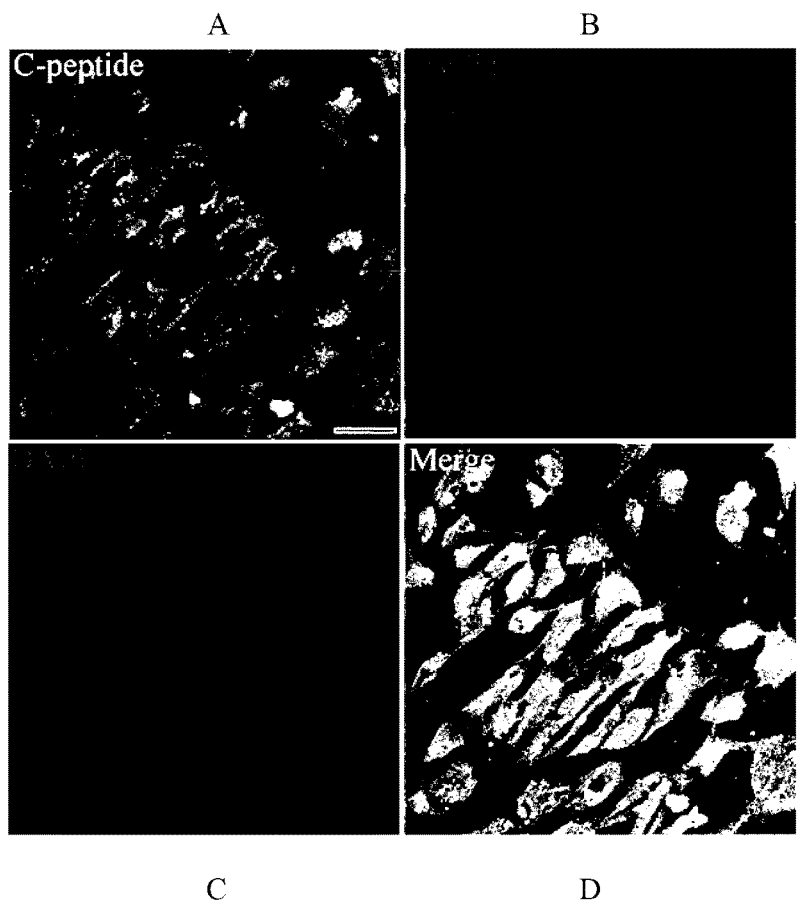
FIG. 9 provides fluorescent micrograph images of cells, collected from human urine, following primary induction with primary induction media containing IDE1, Lithium chloride and Vitamin C for six days, secondary induction in secondary induction media containing cyclopamine-KAAD, Indolactam V, RA, Vitamin C, A83-01 and BRD 7552 (pH adjusted to 7.4) for one day and then cyclopamine-KAAD, Indolactam V, Vitamin C, A83-01 and BRD 7552 for six days (pH adjusted to 7.4), and tertiary induction media containing SB203580 and Vitamin C for nine days, stained for (a) C-peptide, (b) insulin, (c) DAPI, and (d) merged images, scale bar=50 μm.
Figure 10:
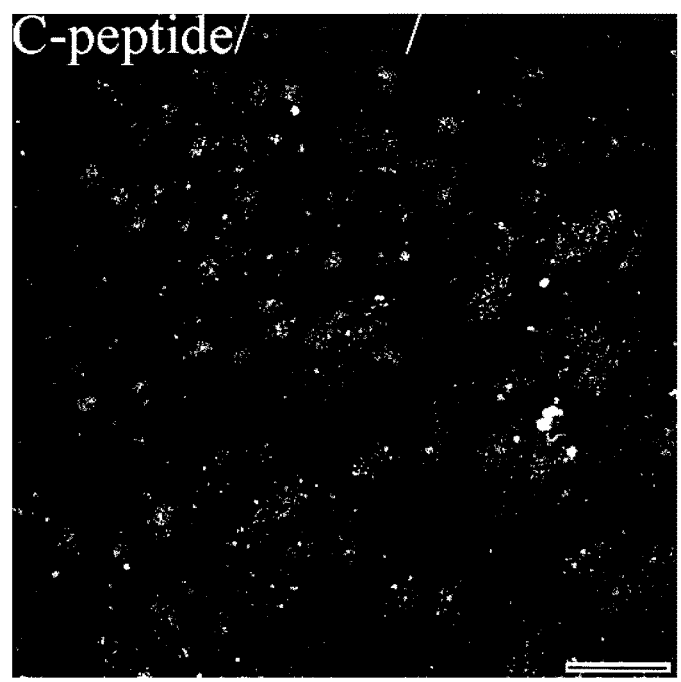
FIG. 10 provides a merged fluorescent micrograph image of cells, collected from human urine, following primary induction with primary induction media containing IDE1, Lithium chloride and Vitamin C for six days, secondary induction in secondary induction media containing cyclopamine-KAAD, Indolactam V, RA, Vitamin C, A83-01 and BRD 7552 (pH adjusted to 7.4) for one day and then cyclopamine-KAAD, Indolactam V, Vitamin C, A83-01 and BRD 7552 for six days (pH adjusted to 7.4), and tertiary induction with tertiary induction media containing SB203580 and Vitamin C for nine days, stained for C-peptide, insulin, and DAPI, scale bar=50 µm.

Example 11 Characterisation of Cells Following Alternative Tertiary Induction with SB203580, Vitamin C, and DAPT Materials and Methods
Tertiary Induction
HUC-F-37 and HUC-M-35 cells were (independently) isolated and cultured as described in Example 1 and underwent primary induction as described in Example 9 and then underwent secondary induction as described in Example 10. Then, cells were cultured in tertiary induction medium consisting of DMEM, 20 nm progesterone, 100 μm putrescine, 1 μg/ml laminin, 10 mm nicotinamide, 25 μg/ml insulin, 50 ug/ml transferrin, 30 nM sodium selenite, 1×B27, 5 μm SB203580, 0.2 mM Vitamin C, and 1 μM DAPT (also known as GSI-IX, LY-374973, N-[2S-(3,5-difluorophenyl) acetyl]-L-alanyl-2-phenyl-1,1-dimethylethyl ester-glycine; Reagents Direct), with pH 7.4, for 9 days. Cells were characterised as described in Example 1. Specifically, cell morphology was examined by phase contrast microscopy, and expression of C-peptide (beta cell marker), insulin (beta cell marker) and DAPI were compared by ICC.
Results and Discussion
As shown in FIG. 8, some cells derived from HUC-F-37 died during the tertiary induction and others showed islet-like morphology, which is consistent with the cells being beta-like. FIG. 9A shows that approximately 100% of cells expressed the beta cell marker c-peptide, FIG. 9B shows that approximately 100% of cells express insulin. Accordingly, these cells are beta-like. However, FIG. 10 is a micrograph of different area of the same dish as that of FIG. 9. As is apparent from FIG. 10, the result is not consistent across the dish with some cells being C-peptide and insulin negative. This suggests that there may be a mixed population of cells present. Similar results were seen when the cells derived from HUC-M-35 were examined. Specifically, some islet-like cells could be seen, and C-peptide positive and insulin positive cells were observed.

Example 12 Alternative Protocol and Conclusions from Above Examples

Materials and Methods
The optimised protocol from the above Examples was determined to be as follows. The HUC cells were obtained and cultured as described in Example 1 and seeded on matri-gel coated dishes at a density of $5 \times 10^4/cm^2$ and then cultured using the induction protocol as below:
Primary Induction (6 Days):
  Media: RPMI+0.2% FBS;
  Small molecule reprogramming factors: 100 μM IDE1, 1 mM LiCl, 0.2 mM Vitamin C (VC);
Secondary Induction (Step 1, 1 Day)
  Media—DMEM+1× L-glutamine+1×B27;
  Small molecule reprogramming factors: 0.25 μM cyclopamine-KAAD, 330 nm Indolactam V, 2 μM RA, 0.2 mM VC, 2.5 μM A83-01, 5 μM BRD 7552; followed by
Secondary Induction (Step 2, 6 Days)
  Media: DMEM+1× L-glutamine+1×B27 (pH 7.4);
  Small molecule reprogramming factors: 0.25 μM cyclopamine-KAAD, 330 nM Indolactam V, 0.2 mM VC, 2.5 μM A83-01, 5 μM BRD 7552;
Tertiary Induction (9 Days):
  Media: DMEM+20 nM progesterone+100 μK putrescine+1 μg/ml laminin+10 mM nicotinamide+25 μg/ml insulin+50 ug/ml transferrin+30 nM sodium selenite+1×B27, pH 7.4;
  Small molecule reprogramming factors: 5 μM SB203580+0.2 mM VC+1 μM DAPT.
Results and Discussion
Following primary induction, the resulting induced cells express very high levels of Sox17 and Foxa2, up to 100% of cells are Sox17 and Fox2a positive. Activin A can be replaced by IED1 in the primary induction medium.
Following secondary induction, most cells express NKX6.1 and Pdx1, but not NGN3. Accordingly, a longer induction time may be required to further optimise results.
Following tertiary induction, the induced cells form islet-like morphologies and some cells are insulin and C-peptide positive. It is anticipated that these cells are insulin secreting.

Example 13 Independent Verification of Alternative Protocol

Materials and Methods
The method as described in Examples, specifically using the induction protocol described in Example 12, was repeated by a different researcher at another institution, with the exception that the cells were cultured on gelatin coated plates. HUC cells were obtained from a 35 year old human female (F35) and a 32 year old human female (F32). The primary induction was started when the density of cells reached $5 \times 10^4$ cells/cm². The HUC cells in culture (ie non-induced) were used as a negative control. ICC was used to examine cell characteristics as described in Example 1.
Quantitative RT-PCR
Total RNA was extracted using the RNeasy Mini Kit (Qiagen) with on-column DNA digestion. Total RNA (500 ng) was converted to cDNA by Superscript III Direct cDNA Synthesis System (Life Technologies). PCR was performed using the primers described in Table 13 and standard methods. The RT profiler PCR array was carried out using the Mouse Neurogenesis and NSC PCR Array (Qiagen).

TABLE 13

PCR primers

| Genes | Forward Primer (5' to 3') | Reverse Primer (5' to 3') | Probe sequence (5' to 3') |
| --- | --- | --- | --- |
| Sox17 | GCTTTCATGGTGTGGGCTAAG (SEQ ID NO: 1) | CGACTTGCCCAGCATCTTG (SEQ ID NO: 2) | AGCAGAATCCAGACCTGCACAACGC (SEQ ID NO: 3) |
| Foxa2 | CGGGCGAGTTAAAGTATG (SEQ ID NO: 4) | TCTGCATAGTAGCTGCTC (SEQ ID NO: 5) | CCTTCCATCTTCACCGCTCC (SEQ ID NO: 6) |
| Nestin | CAGCGTTGGAACAGAGGTT (SEQ ID NO: 7) | CTCTGTAGGCCCTGTTTCT (SEQ ID NO: 8) | TCCACAGCCAGCTGGAACTT (SEQ ID NO: 9) |
| CXCR4 | GGTTGTGTTCCAGTTTCA (SEQ ID NO: 10) | GACAGCTTGGAGATGATAA (SEQ ID NO: 11) | CTTATCCTGCCTGGTATTGTCATCCT (SEQ ID NO: 12) |
| PDX1 | TGCTAGAGCTGGAGAAGGAGT (SEQ ID NO: 13) | TCTTGATGTGTCTCTCGGTCA (SEQ ID NO: 14) | CTATTCAACAAGTACATCTCACGGCCGC (SEQ ID NO: 15) |

TABLE 13-continued

PCR primers

| Genes | Forward Primer (5' to 3') | Reverse Primer (5' to 3') | Probe sequence (5' to 3') |
|---|---|---|---|
| NGN3 | AAGAGCGAGTTGGCACTGA (SEQ ID NO: 16) | GATGTAGTTGTGGGCGAAGC (SEQ ID NO: 17) | CAATCGAATGCACAACCTCAACTCGG (SEQ ID NO: 18) |
| HNF4a | GGACAAAGACAAGAGGAA (SEQ ID NO: 19) | CCTCATAGCTTGACCTTC (SEQ ID NO: 20) | CGCTCATTCTGGACGGCTTC (SEQ ID NO: 21) |
| HNF6 | GGCAAGACAAATGATGAG (SEQ ID NO: 22) | CATGGTAGAACAGATGAGA (SEQ ID NO: 23) | AGATGTCCGCTCAATGGCTCA (SEQ ID NO: 24) |
| HB9 | CTTCCCTTTTAAGCAAGG (SEQ ID NO: 25) | CCAGAGTTCAAGTTTCAG (SEQ ID NO: 26) | CGCCTCACCTGCTCTTCAAG (SEQ ID NO: 27) |
| Pax6 | CAGTCACAGCGGAGTGAAT (SEQ ID NO: 28) | CTTTTGCATCTGCATGGGTCT (SEQ ID NO: 29) | CCACTGCCGGACTCCACCC (SEQ ID NO: 30) |
| Insulin 1 | GCATCTGCTCCCTCTACCAG (SEQ ID NO: 31) | GGTTCAAGGGCTTTATTCCA (SEQ ID NO: 32) | TGGAGAACTACTGCAACTAGACGCAGCC (SEQ ID NO: 33) |
| Somatostatin | CCAACCAGACGGAGAATGAT (SEQ ID NO: 34) | TAGCCGGGTTTGAGTTAGCA (SEQ ID NO: 35) | ATGAAATGAGGCTTGAGCTGCAGAGATC (SEQ ID NO: 36) |
| Glut-2 | GGACCTGCAATTTCATTG (SEQ ID NO: 37) | CTCCAGCAAAGAGGAAAA (SEQ ID NO: 38) | TAAGGTCCACAGAAGTCCGCAAT (SEQ ID NO: 39) |
| Glucagon | CACGATGAATTTGAGAGA (SEQ ID NO: 40) | CAGAGAAAGAACCATCAG (SEQ ID NO: 41) | CTTCAACAATGGCGACCTCTTCTG (SEQ ID NO: 42) |
| Occludin | CCCGTTTGGATAAAGAATTG (SEQ ID NO: 43) | CCTTCACTTGCTTCAGTC (SEQ ID NO: 44) | ATTGTATTCATCAGCAGCAGCCAT (SEQ ID NO: 45) |
| Claudin1 | CTCCTTGCTGAATCTGAG (SEQ ID NO: 46) | CCACAAAGATTGCTATCAC (SEQ ID NO: 47) | CAACCACCATCAAGGCACGG (SEQ ID NO: 48) |
| KRT7 | CTCCCAGACATCTTTGAG (SEQ ID NO: 49) | GCGGTGGTTAATTTCATC (SEQ ID NO: 50) | AGTCCTCCACCACATCCTGC (SEQ ID NO: 51) |
| NR3C2 | GCTCAAAACCAGATACAG (SEQ ID NO: 52) | GACACATCCAAGAATACTG (SEQ ID NO: 53) | TCTCCACGCTCAACCGCTTA (SEQ ID NO: 54) |
| L1CAM | ACCTCTACTTTGCCAATG (SEQ ID NO: 55) | CTGTCAATCATGCTGTTG (SEQ ID NO: 56) | ACCTCCGACAACCACTCAGAC (SEQ ID NO: 57) |
| SLC2A1 | CGTCTTCATCATCTTCAC (SEQ ID NO: 58) | TGGGATAGAAGCTTTGTA (SEQ ID NO: 59) | TGCTCCTGGTTCTGTTCTTCATCT (SEQ ID NO: 60) |
| CD13 | CAGAGCAACTGGAAGAAG (SEQ ID NO: 61) | CTCGTTGTCCTTCTTGAA (SEQ ID NO: 62) | TGGTGGCTCGTTCTCCTTCTC (SEQ ID NO: 63) |
| Vimentin | GACCTGCTCAATGTTAAG (SEQ ID NO: 64) | CAACCGTCTTAATCAGAAG (SEQ ID NO: 65) | CTTGACATTGAGATTGCCACCTACAG (SEQ ID NO: 66) |
| Col1a1 | GTGCTAAAGGTGCCAATG (SEQ ID NO: 67) | GTCCTTGAACACCAACAG (SEQ ID NO: 68) | TCCTGGTATTGCTGGTGCTCC (SEQ ID NO: 69) |

TABLE 13-continued

PCR primers

| Genes | Forward Primer (5' to 3') | Reverse Primer (5' to 3') | Probe sequence (5' to 3') |
|---|---|---|---|
| Col3a1 | GGGAATGGAGCAAAACAGTCTT (SEQ ID NO: 70) | CCAACGTCCACACCAAATTCT (SEQ ID NO: 71) | TCGAACACGCAAGGCTGTGAGACTACC (SEQ ID NO: 72) |
| GAPDH | ACCACAGTCCATGCCATCAC (SEQ ID NO: 73) | TCCACCACCCTGTTGCTGTA (SEQ ID NO: 74) | CTGCACCACCAACTGCTTAGC (SEQ ID NO: 75) |

Results and Discussion

Generation of Urine-Derived Cell Lines

Two types of cells were observed at p0, but type II cells become dominant when the cell colonies are mixed up (from p1). At earlier passage, most cells have small round or triangular morphology, while big round forms of cells are generated at higher passage (over p5 to p20). Therefore, the cells from p5 to p10 are usually used. The characteristics of the obtained HUC were similar to urine-derived cell lines described above.

Primary Induction

Some cells were aggregated following primary induction as visualised by phase contrast microscopy. These aggregations were maintained through to the three-step induction process. Further, during the entire three-step induction protocol, the cells grew well. Cells following the primary induction were examined for definitive endoderm cell markers with anti-FOXA2 and anti-SOX17 antibodies. Both FOXA2 and SOX17 were strongly expressed in the treated cells, but these markers were also weakly expressed in the control cells. Accordingly, mRNA samples of the cells before and after primary induction will be examined to confirm the upregulation.

Secondary Induction

By the sixth day of the secondary induction, the size of cell aggregates was markedly larger than at the second day of the secondary induction. The cells were growing well. The induced and mainly aggregated cells were stained strongly for using specific antibody for PDX1 and NKX6.1. The cell aggregates stained for cell marker PDX1, NXK6.1 and NGN3 strongly. Negative control cells were negative for PDX1, and were weakly positive for NX6.1 and NGN3 and did not have cell aggregates.

Tertiary Induction

Figure 11:
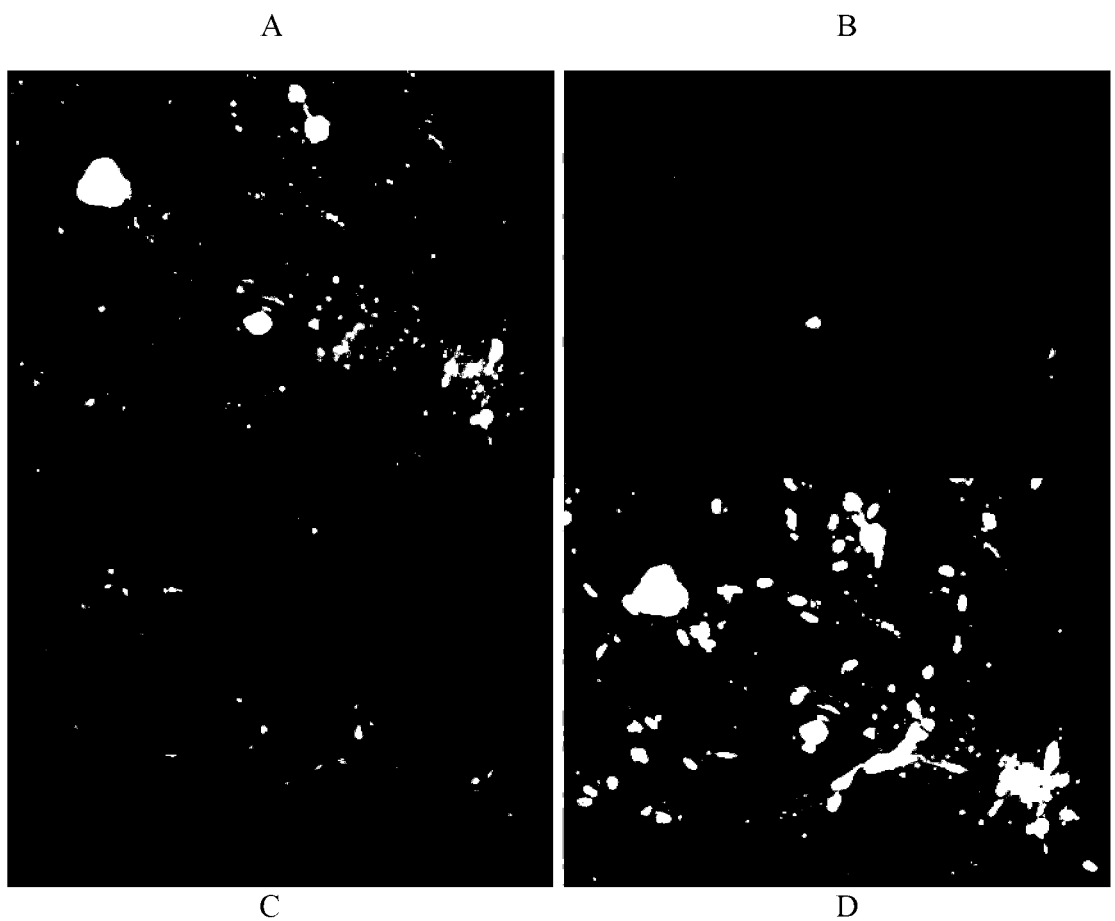
FIG. 11 provides fluorescent micrograph images of cells, collected from human urine, following primary induction with primary induction media containing IDE1, LiCl and Vitamin C for 6 days, secondary induction with secondary induction media containing cyclopamine-KAAD, Indolactam V, RA, VC, A83-01, BRD 7552 for 1 day; followed by cyclopamnine-KAAD, Indolactam V, VC, A83-01, and BRD 7552 (pH adjusted to 7.4) for 6 days; and tertiary induction media containing SB203580, VC and DAPT for 9 days, stained for (a) insulin, (b) C-peptide, (c) DAPI and (d) merged, scale bar=50 µm.
Figure 12:
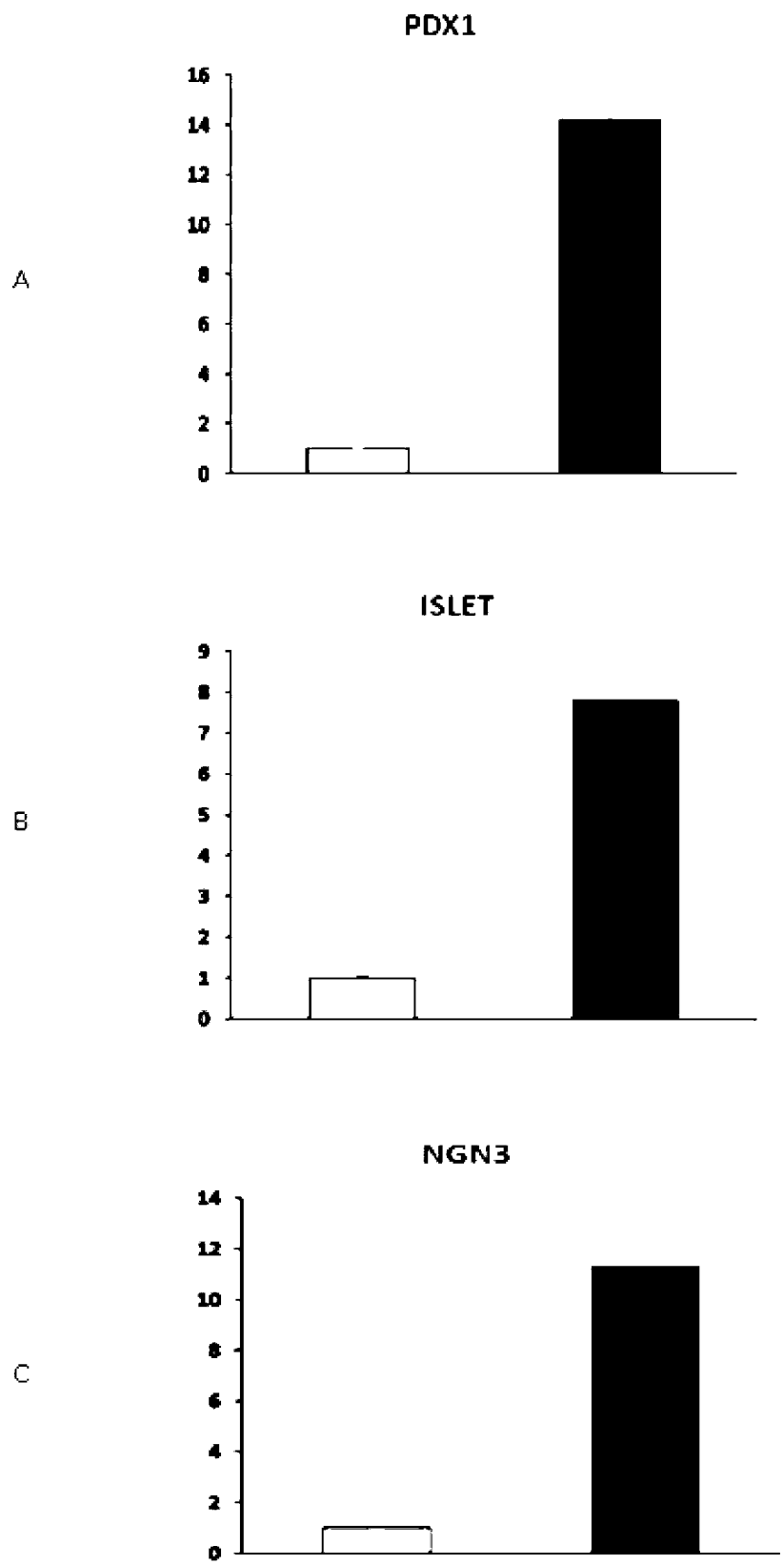
FIG. 12 provides graphical representation of (a) PDX1, (b) islet (ISL), and (c) NGN3 mRNA relative gene expression levels for cells collected from human urine before induction (white column) and following primary induction with primary induction media containing IDE1, LiCl and Vitamin C for 6 days, secondary induction with secondary induction media containing cyclopamine-KAAD, Indolactam V, RA, VC, A83-01, BRD 7552 for 1 day (pH adjusted to 7.4); followed by cyclopamine-KAAD, Indolactam V, VC, A83-01, and BRD 7552 (pH adjusted to 7.4) for 6 days; and tertiary induction media containing SB203580, VC and DAPT for 9 days (black column)

There were a large number of aggregated cell groups, which remained aggregated following the tertiary induction process. Some of aggregated cells tend to be detached in the 3rd step, which are similar to those shown in Pennarossa et al. 2013. Large numbers of cells were detached when they were fixed with 4% PFA. This may be as gelatin was used as a coating material, although induction has also been carried out on the matri-gel coated dish also. After the tertiary induction step, insulin expression and C-peptide was examined. Some of cells (36.6±5%) expressed insulin and C-peptide (FIG. 11). Insulin expression was also checked using an alternative anti-insulin antibody (H-86, Santa Cruz, Cat No. sc-9168). Accordingly, following the tertiary induction, insulin expression in cells was detected by different types of human insulin-specific antibodies. The quantitative RT-PCR results also indicated that the cells following the tertiary induction were committed into a pancreatic lineage (FIG. 12) compared to negative control cells. The mRNA expression levels of PDX1, Ngn3 and ISL (another beta cell marker) were up-regulated in the induced cells, indicating the induced cells were committed into a pancreatic lineage.

Example 14 C-Peptide Release Assay

Materials and Methods

HUC cells were induced as described in Example 12. The culture medium was removed and cells were rinsed with PBS for 3 times and then stimulated for 1 h and 24 h with 20 mM D-glucose in MCDB 131 (Life Technologies) supplemented with 10% (vol/vol) FBS and 2 mM L-glutamine (Life Technologies). Glucose-dependent C-peptide release was assessed with a Human C-peptide ELISA Kit (EIAab, E0447h), following the manufacturer's instructions.

Results and Discussion

The induced cells released C-peptide at a concentration of approximately 145 ng/ml. There was no difference between 1 and 24 hours of stimulation with by 20 mM D-glucose. Accordingly, a one-hour incubation with glucose is sufficient to establish that the induced beta cells can secrete c-peptide.

Example 15 Incubation of Cells Following Further Alternative Protocol with Three Step Secondary Induction (First Step: Vitamin C; Second Step: Vitamin C, RA, Cyclopamine-KAAD, Indolactam V, and Dorsomorphin; Third Step: Vitamin C, RA and Cyclopamine-KAAD) and Alternative Three Step Tertiary Induction (First Step: Vitamin C, RA, Cyclopamine-KAAD, DAPT, A83-01, and Triiodothyronine; Second Step: Vitamin C, RA, DAPT, A83-01, and Triiodothyronine; Third Step: Vitamin C, A83-01 and Triiodothyronine)

Materials and Methods

S2 media contains MCDB131 medium (Life Technologies)+8 mM D-Glucose+1.23 g/L NaHCO3+2% BSA, Insulin-Transferrin-Selenium-Ethanolamine (ITS-X) 1:50+2 mM Glutamax (L-alanine-L-glutamine dipeptide; Life Technologies)+0.25 mM Vitamin C+1% p/s; S3 media contains MCDB31 medium+8 mM D-Glucose+1.23 g/L NaHCO3+2% BSA+ITS-X 1:200+2 mM Glutamax+0.25 mM Vitamin C+1% p/s; S5 media contains MCDB131 medium+20 mM D-Glucose+1.754 g/L NaHCO3+2% BSA+ITS-X 1:200+2 mM Glutamax+0.25 mM Vitamin C+1% p/s+Heparin 10 µg/ml (Sigma; H3149; 1 mg=100 units); and S6 media contains CMRL 1066 (Mediatech; 99-603-CV) supplemented with 10% FBS (HyClone, VWR; 16777)+1% p/s. Note that CMRL 1066 media contains 0.28 mM ascorbic acid, a form of Vitamin C. After the addition of 10% FBS and 1% p/s, the concentration of Vitamin C would be approximately 0.25 mM.

Primary and Secondary Induction

HUC cells were isolated and cultured as described in Example 1 and underwent primary induction as described in Example 9 (ie, the primary induction medium contained RPMI 1640 Medium, 0.2% FBS, 100 µM IDE1, 1 mM LiCl, and 0.2 mM Vitamin C, and the cells were cultured in this medium for six days). The cells then underwent secondary induction as follows: The cells were incubated in S2 medium (including Vitamin C) and 100 ng/ml basic fibroblast factor (bFGF) for two days; then in S2 medium (including Vitamin C) containing 100 ng/ml bFGF, 200 nM RA, 0.25 µM cyclopamine-KAAD, and 30 nm Indolactam V and 10 µM dorsomorphin (Reagents Direct) for 2 days; and then S3 medium (including Vitamin C) containing 100 ng/ml bFGF, 100 nM RA, and 0.25 µM cyclopamine-KAAD for 5 days.

Tertiary Induction

Following secondary induction, the cells then underwent tertiary induction as follows. The cells were incubated in S5 media (including Vitamin C) containing 100 mM RA, 0.25 µM cyclopamine-KAAD, 1 µM DAPT, 2.5 µM A83-01, 1 µM triiodothyronine (T3; Sigma-Aldrich; 3,3',5-Triiodo-L-thyronine sodium salt, Catalogue No. T6397), and 20 ng/ml EGF for 4 days; then S5 media (including Vitamin C) containing 25 mM RA, 1 µM DAPT, 2.5 µM A83-01, 1 µM T3, and 20 ng/ml EGF for 3 days; and then S6 medium (including Vitamin C) containing 2.5 µM A83-01, and 1 µM T3 for 14 days.

Results and Discussion

It was observed that cells were not thriving in the final 14 day incubation step of the tertiary induction protocol. Accordingly, it was decided to re-test the protocol without A83-01 in the final 14 day incubation step.

Example 16 Characterisation of Cells Following Three Step Secondary Induction (First Step: Vitamin C; Second Step: Vitamin C, RA, Cyclopamine-KAAD, Indolactam V, and Dorsomorphin; Third Step: Vitamin C, RA and Cyclopamine-KAAD) and Three Step Tertiary Induction (First Step: Vitamin C, RA, Cyclopamine-KAAD, DAPT, A83-01, and Triiodothyronine; Second Step: Vitamin C, RA, DAPT, A83-01, and Triiodothyronine; Third Step: Vitamin C and Triiodothyronine)

Materials and Methods

Cells were induced as described in Example 15, except that A83-01 was omitted from the final incubation step of the tertiary induction protocol.

Cell Characterisation

Aliquots of cells were taken after each of the primary, secondary and tertiary induction protocols and were characterised using the immunocytochemistry protocols above, specifically, following the primary induction protocol, cells were tested for the presence of definitive endoderm markers Sox17 and Foxa2; following the secondary induction protocol, cells were tested for the presence of pancreatic markers PDX1, NKX6.1, and NGN3; and following the tertiary induction protocol, cells were tested for the presence of insulin and C-peptide. Cells following each step of the induction protocol also underwent qualitative RT-PCT (q-PCR) as described above, with the total RNA of 500 ng used for cDNA synthesis. The cells resulting from the tertiary induction protocol were also tested for C-peptide expression as described above. The cells were also examined by FACS analysis for insulin and C-peptide expression using standard techniques and the antibodies described above.

C-Peptide Release

Following tertiary induction, the culture medium was collected (sample "0"), the cells were then washed twice with Kreb's buffer (0.126 M NaCl, 2.5 mM KCl, 25 mM NaHCO3, 1.2 mM NaH2PO4, 1.2 mM MgCl2, 2.5 mM CaCl2, pH adjusted to 7.2), and then incubated in Kreb's buffer containing low (2 mM) glucose in for 2 hours to remove residual c-peptide. Cells were then washed twice with Kreb's buffer, and then incubated in Kreb's buffer containing low (2 mM) glucose for 30 mins. After 30 mins, the supernatant were collected (sample "1-2"). The cells were washed twice as above and incubated in Kreb's buffer containing high (20 mM) glucose for 30 min, and the supernatant were collected (sample "1-20"). The cells were washed twice as above, and incubated in Kreb's buffer containing low (20 mM) glucose for 30 min, and the supernatant were collected (sample "2-2"). The cells were washed twice as above, and incubated in Kreb's buffer containing high (20 mM) glucose for 30 mins and the supernatant were collected (sample "2-20"). Finally, the cell number was counted by TC-20 automated cell counter (Bio-Rad). C-peptide levels were measured in each sample using a C-peptide were tested by the human C-peptide ELISA kit from EIAAB following the manufacturer's instructions. Urine-derived cells that had not undergone the induction protocol and human islet cells (Prodo Laboratories, Inc) were examined in tandem as controls. For each of the high and low glucose samples, the results are shown as mean±SD of the first and second samples.

Results and Discussion

Following the secondary induction protocol, immunocytochemistry experiments showed the cells were 100% positive for NKX6.1, 33.8% NGN3 positive and 23.1% PDX1 positive (data not shown). This confirms the presence of pancreatic precursor-like cells, and indicates that pancreatic precursor cells have been induced.

Following tertiary induction, immunocytochemistry experiments showed that 85±2.5% of the cells were double positive for C-peptide and insulin. This result confirms the presence of beta-like cells, and indicates that beta cells have been induced.

Figure 13:
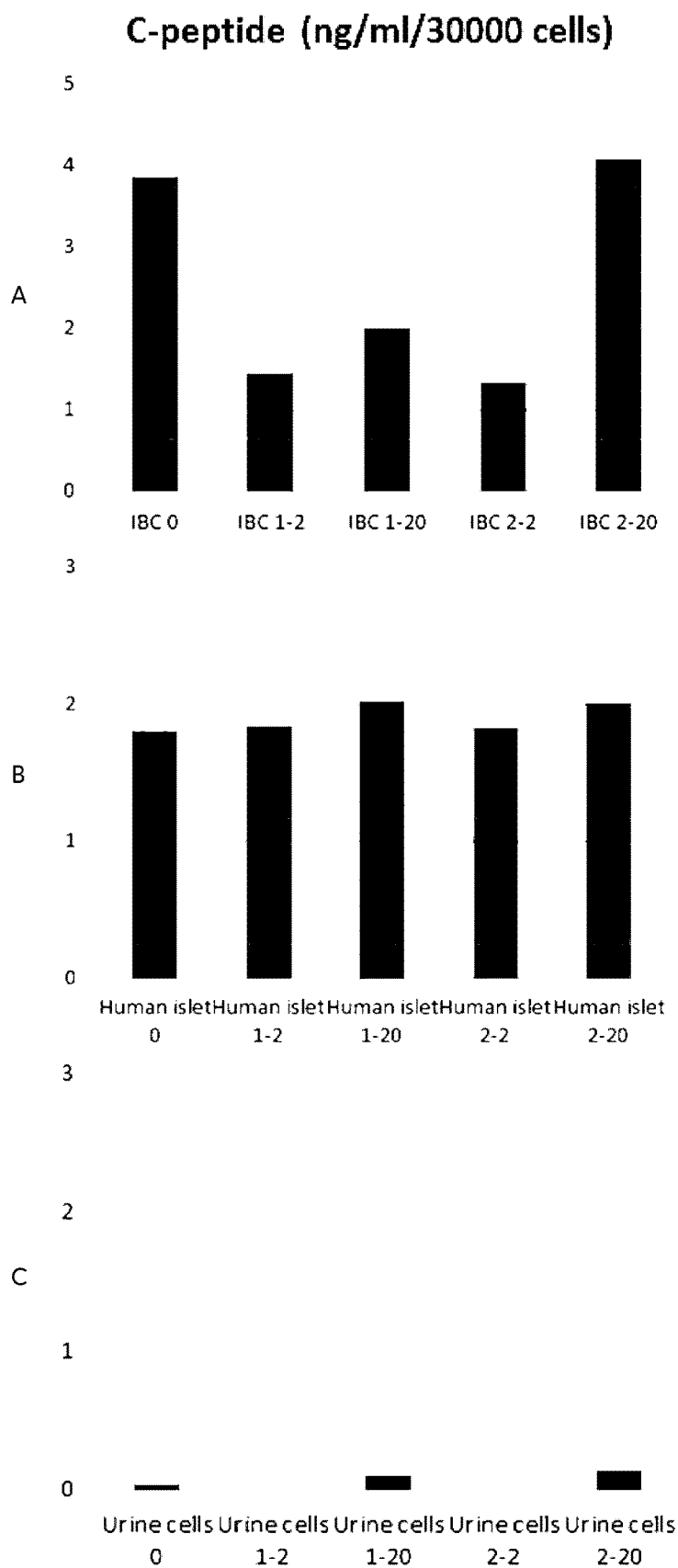
FIG. 13 provides graphical representation of C-peptide released in ng/ml/30000 cells in (A) cells following tertiary induction (referred to as "IBC"), (B) human islet cells and (C) urine cells; wherein the "0" sample refers to culture medium supernatant, "1-2" refers to the sample obtained following the first stimulation of cells with low (2 mM) glucose, "1-20" refers to the sample obtained following the first stimulation of cells with high (20 mM) glucose, "2-2" refers to the sample obtained following the second stimulation cells with low (2 mM) glucose, and "2-20" refers to the sample obtained following the second stimulation of cells with high (20 mM)

As shown in FIG. 13A, C-peptide released from cells following the tertiary induction protocol (referred to as induced beta cells (IBC)) culture medium sample was 3.86 ng/ml/30000 cells, and was 1.39±0.05 ng/ml/30,000 cells in the 2 mM glucose samples, while it was 3.04±1.04 in the 20 mM glucose samples. In comparison, the C-peptide from human islet culture medium was 1.81 ng/ml/30000 cells, while it was 1.84±0.01 in 2 mM glucose sample and 2.01±0.01 in 20 mM glucose sample, as shown in FIG. 13B. The C-peptide released from the urine cell culture medium sample was 0.04 ng/ml/30000 cells, whereas C-peptide was not detected in either of the 2 mM glucose samples, and was 0.13±0.02 ng/ml/30000 cells in the 20 mM glucose samples. This data indicates that the induced beta cells following the tertiary induction protocol are able to release as much or more C-peptide than human islets cells, and the urine derived cells (ie in the absence of the induction protocol) release very low or undetectable levels of C-peptide. This data confirms that the tertiary induction protocol produces cells that are beta-cell like, and provides further support that the cells are induced beta cells.

Figure 14A:
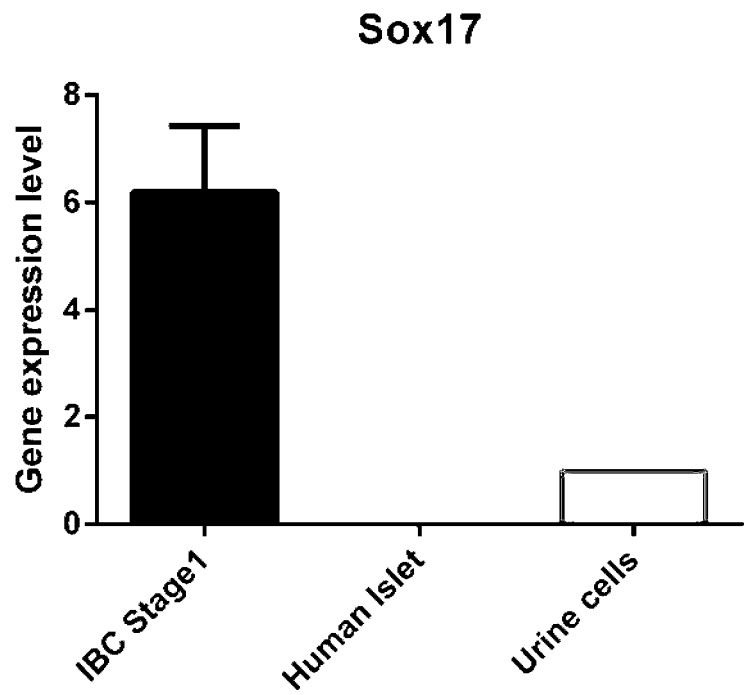
FIG. 14 provides graphical representation of gene expression levels following q-PCR for (A) sox17 or (B) Foxa2 expression of cells following the primary induction protocol (referred to as "IBC stage1"), human islet cells or urine cells; (C) Pdx1 or (D) NGN3 expression of cells following the secondary induction protocol (referred to as "IBC stage2"), human islet cells or urine cells; or (E) insulin or (F) somatostatin (SST) expression of cells following the tertiary induction protocol (referred to as "IBC stage 3"), human islet cells or urine cells.
Figure 14B:
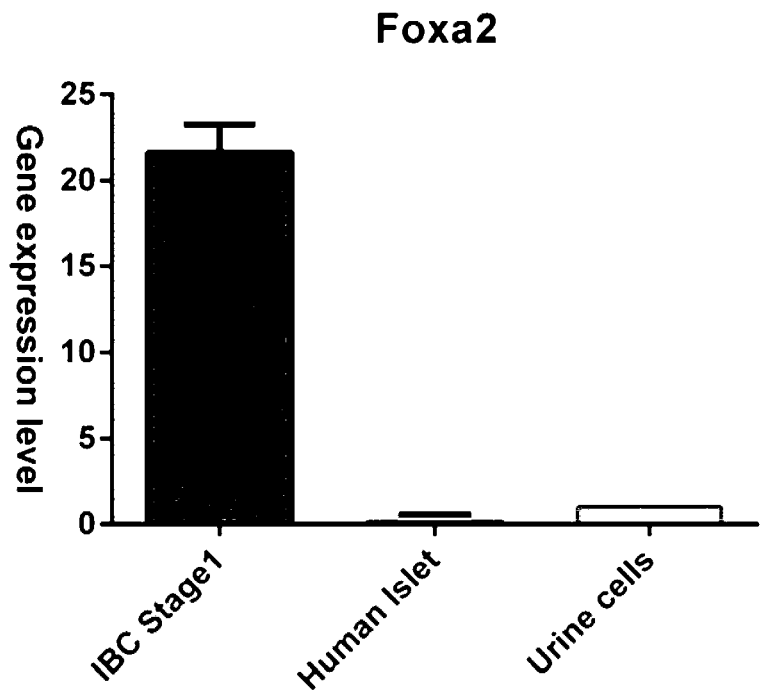
Figure 14C:
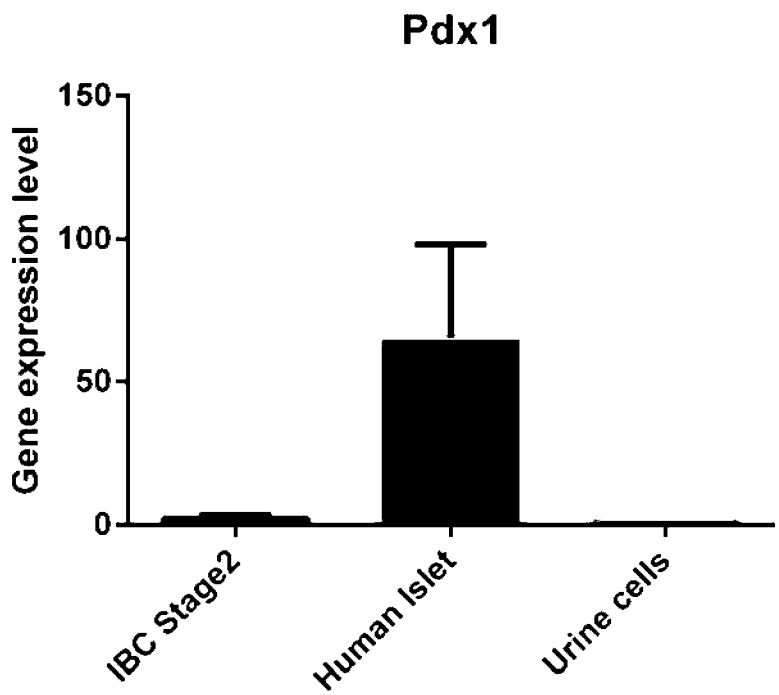
Figure 14D:
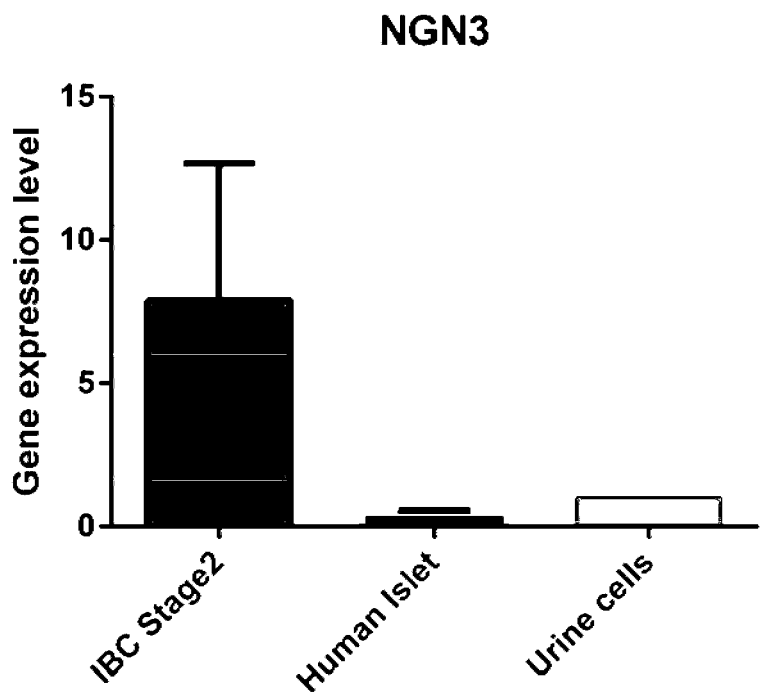
Figure 14E:
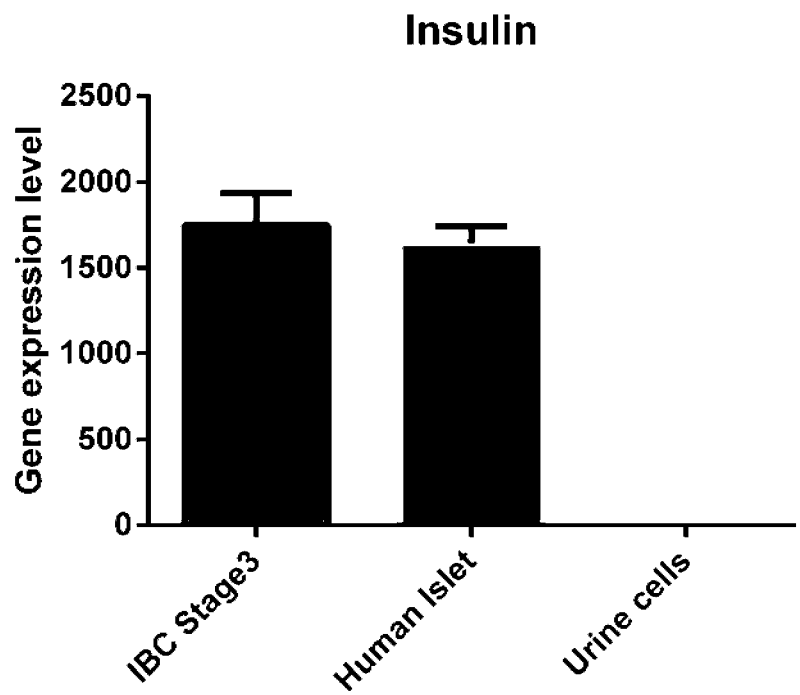
Figure 14F:
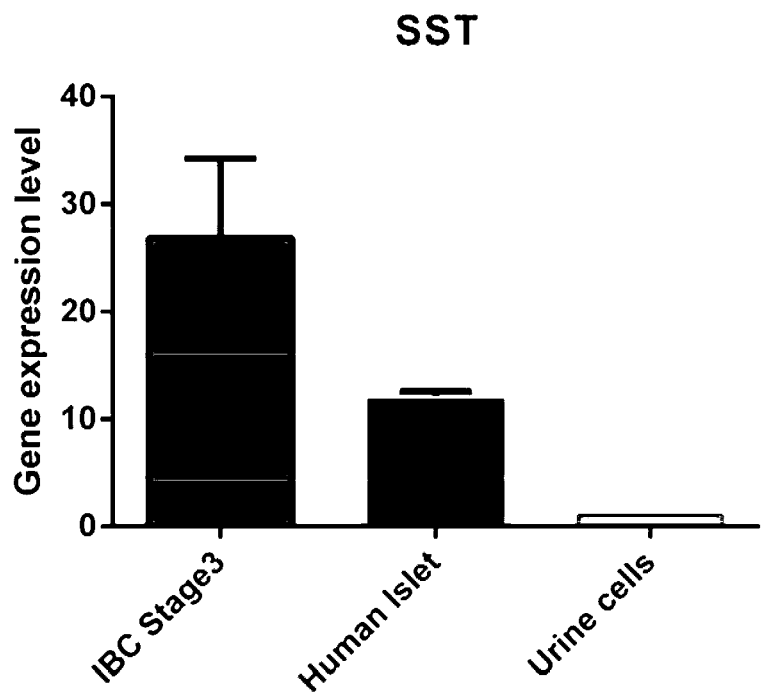

As shown in FIGS. 14A and 14B, the primary induction protocol resulted in cells (referred to as "IBC stage 1") that have increased expression of Sox17 and Foxa2 genes by 6 and 21 times, respectively, compared to urine cells as determined by q-PCR, confirming the cells are definitive endoderm-like and accordingly indicating the cells are induced definitive endoderm cells. Following the secondary induction protocol, cells (referred to as "IBC stage 2") had 2 and 8 times higher Pdx1 and NGN3 expression, as compared to urine cells, confirming the cells are pancreatic-precursor-like and accordingly indicating that the cells are induced pancreatic precursor cells, as shown in FIGS. 14C and 14D, respectively. Following the tertiary induction protocol, cells (referred to as "IBC stage 3") expressed 1751 and 26 times more insulin and somatostatin (SST), respectively, compared to urine cells (FIGS. 14E and 14F). Further, the cells following the tertiary induction protocol expressed similar levels of insulin as human islet cells, and approximately twice as much somatostatin as human islet cells. This data indicates that the cells following the tertiary induction protocol are beta cell-like, and accordingly indicates that the cells are induced beta cells.

Figure 15:
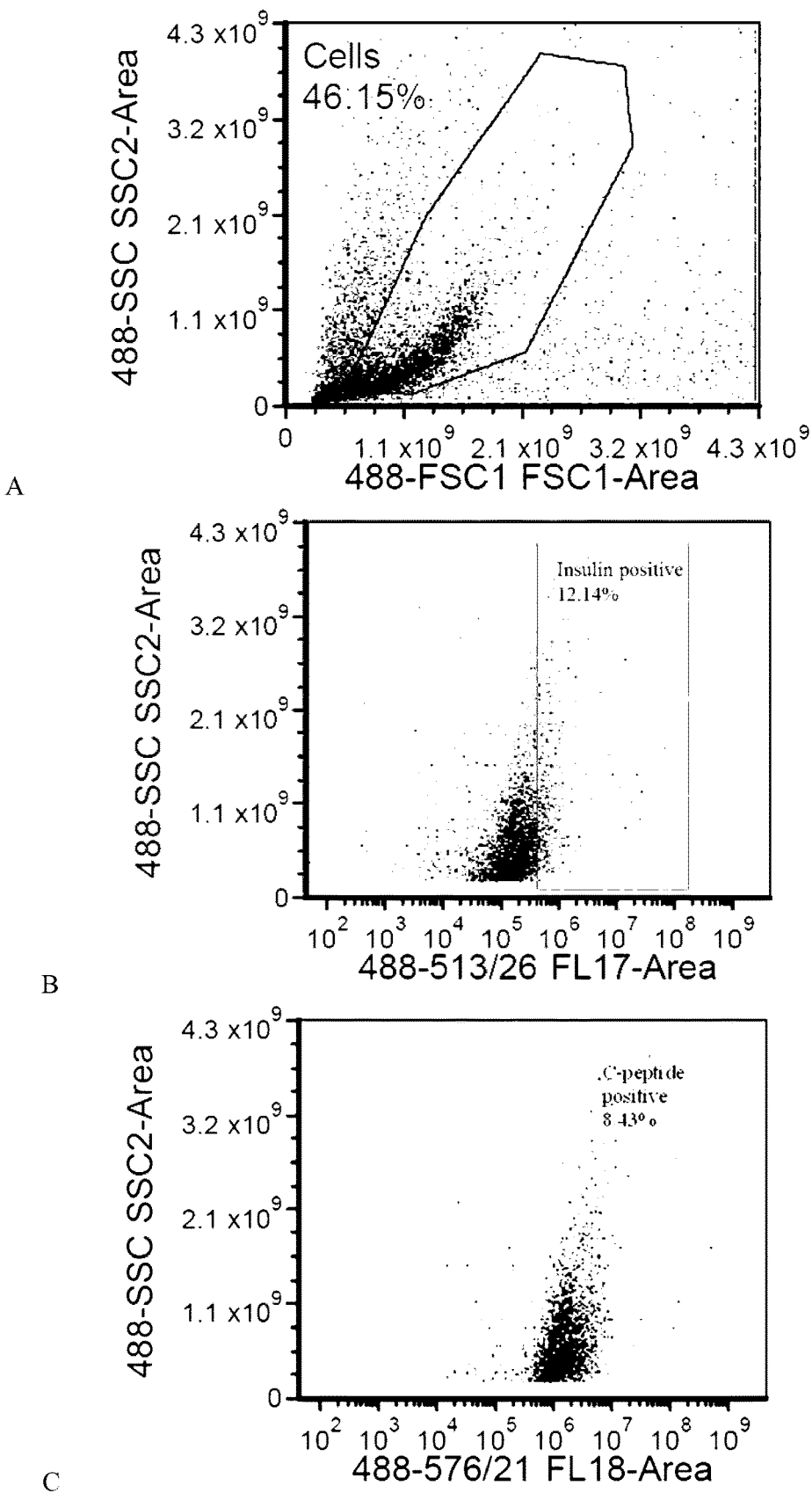
FIG. 15 provides FACS histograms of cells following tertiary induction, with (A) indicating gating for live cells; (B) showing staining using an anti-insulin antibody; and (C) showing staining using anti-C-peptide antibody.

FIG. 15B shows that following the tertiary induction, 12.14% of cells were positive for insulin expression, and FIG. 15C shows that 8.43% of cells were positive for C-peptide expression. FIG. 15A indicates the gating for live cells applied in accordance with standard methods.

Accordingly, this further alternative protocol was also successful at inducing urine derived cells into, ultimately, beta-like cells. The induction protocol was as below:

Primary Induction (6 Days):
  Media: RPMI+0.2% FBS;
  Small molecule reprogramming factors: 100 µM IDE1, 1 mM LiCl, 0.2 mM Vitamin C (VC);
Secondary Induction (Step 1, 2 Days)
  Media: MCDB131 medium+bFGF+8 mM D-Glucose+1.23 g/L NaHCO3+2% BSA, Insulin-Transferrin-Selenium-Ethanolamine (ITS-X) 1:50+2 mM Glutamax (L-alanine-L-glutamine dipeptide+1% p/s;
  Small molecule reprogramming factors: 0.25 mM Vitamin C;
Secondary Induction (Step 2, 2 Days)
  Media: MCDB131 medium+bFGF+8 mM D-Glucose+1.23 g/L NaHCO3+2% BSA, Insulin-Transferrin-Selenium-Ethanolamine (ITS-X) 1:50+2 mM Glutamax (L-alanine-L-glutamine dipeptide+1% p/s;
  Small molecule reprogramming factors: 0.25 mM Vitamin C, 200 nM RA, 0.25 µM cyclopamine-KAAD, and 30 nm Indolactam V and 10 µM dorsomorphin;
Secondary Induction (Step 3, 5 Days)
  Media: MCDB131 medium+bFGF+8 mM D-Glucose+1.23 g/L NaHCO3+2% BSA+ITS-X 1:200+2 mM Glutamax+0.25 mM Vitamin C+1% p/s;
  Small molecule reprogramming factors: 0.25 mM Vitamin C, 100 nM RA, and 0.25 µM cyclopamine-KAAD;
Tertiary Induction (Step 1, 4 Days)
  Media: MCDB131 medium+20 ng/nl EGF+20 mM D-Glucose+1.754 g/L NaHCO3+2% BSA+ITS-X 1:200+2 mM Glutamax+1% p/s+10 µg/ml Heparin;
  Small molecule reprogramming factors: 100 mM RA, 0.25 µM cyclopamine-KAAD, 1 µM DAPT, 2.5 µM A83-01, 1 µM triiodothyronine;
Tertiary Induction (Step 2, 3 Days)
  Media: MCDB131 medium+20 ng/nl EGF+20 mM D-Glucose+1.754 g/L NaHCO3+2% BSA+ITS-X 1:200+2 mM Glutamax+1% p/s+10 µg/ml Heparin;
  Small molecule reprogramming factors: 25 mM RA, 1 µM DAPT, 2.5 µM A83-01, 1 µM T3;
Tertiary Induction (Step 3, 14 Days)
  Media: CMRL 1066 supplemented with 10% FBS (includes Vitamin C);
  Small molecule reprogramming factors: 1 µM T3

Example 17 Characterising Urine Cells

Materials and Methods

Three difference human urine cell samples and primary fibroblasts isolated using standard techniques were characterised by q-PCR (using taqman primers) as described above, with 500 ng total RNA used for cDNA synthesis.

Results and Discussion

Figure 16A:
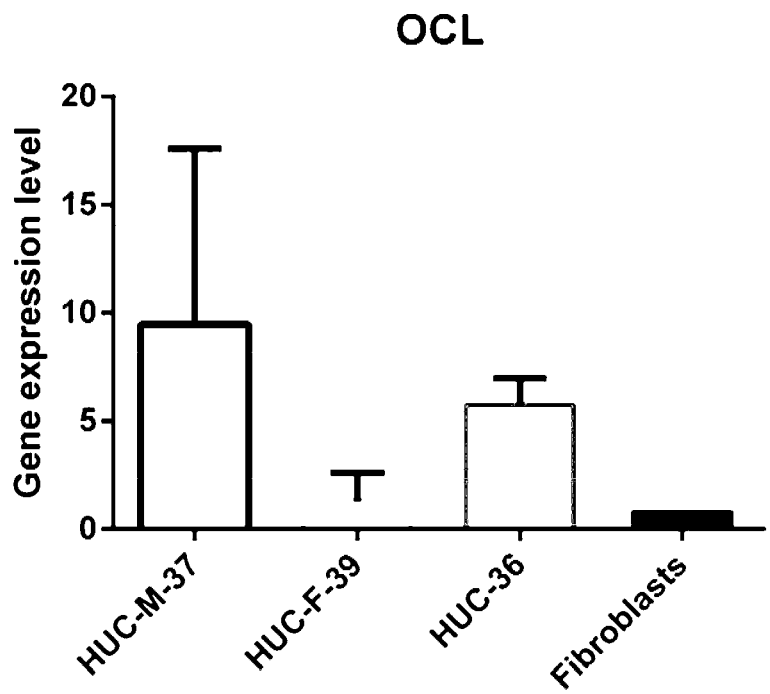
FIG. 16 provides graphical representation of gene expression levels following q-PCR for three different urine cell samples and a fibroblast sample, for (A) Occludin (OCL), (B) KRT7, (C) NR3C2, (D) L1CAM, (E) SLC2A1, and (F) VIMENTIN.
Figure 16B:
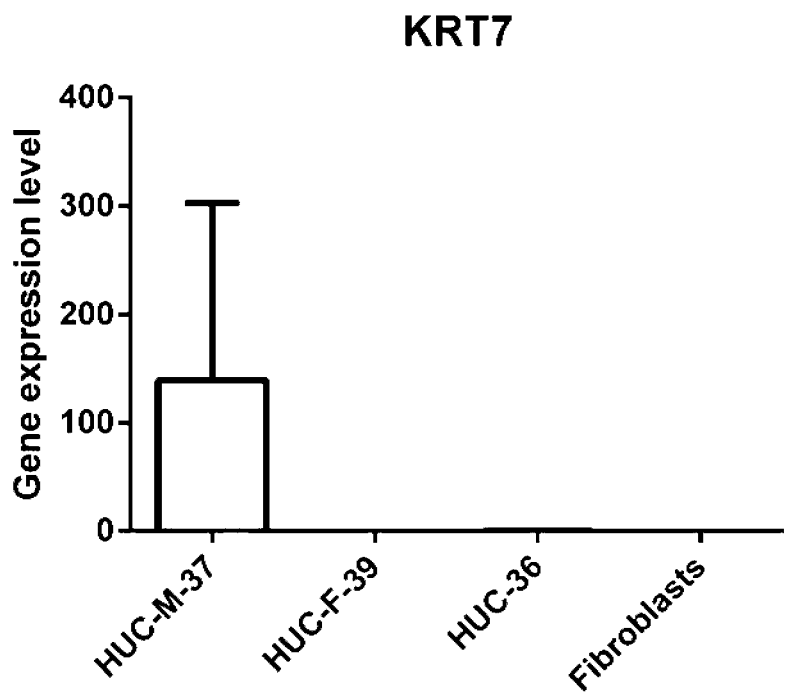
Figure 16C:
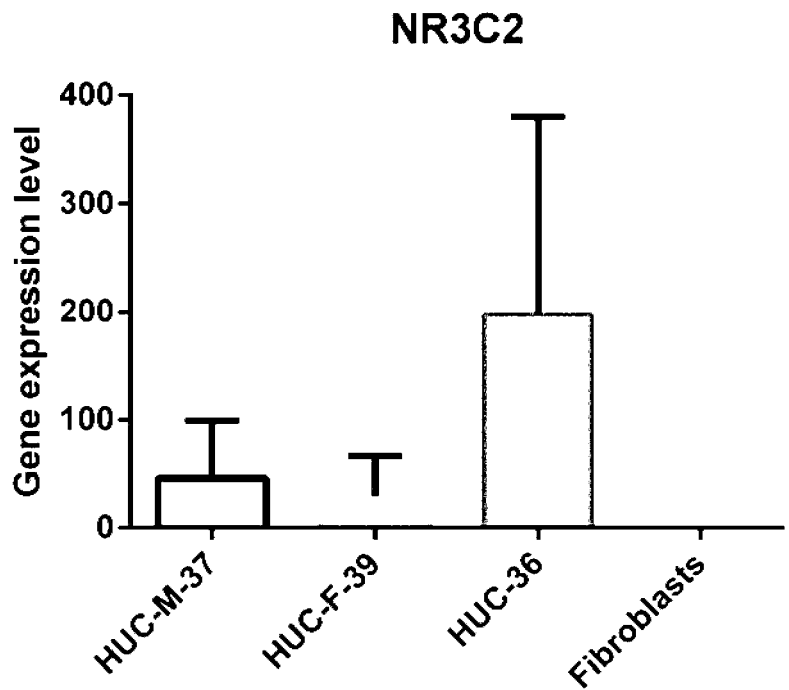
Figure 16D:
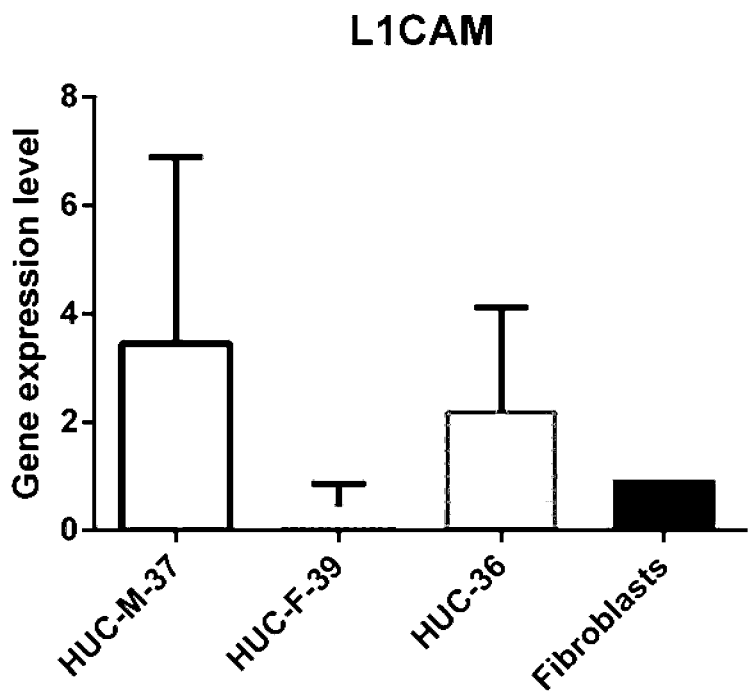
Figure 16E:
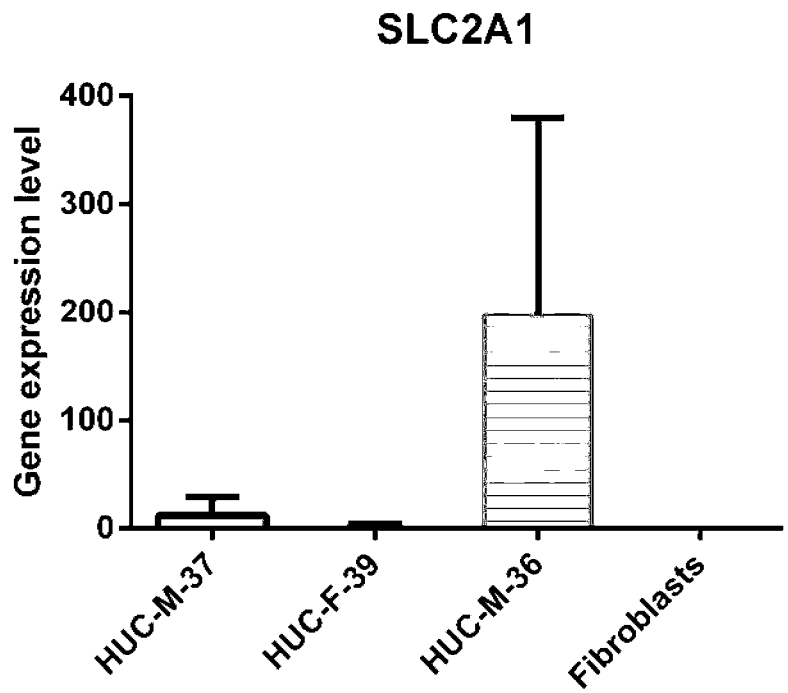
Figure 16F:
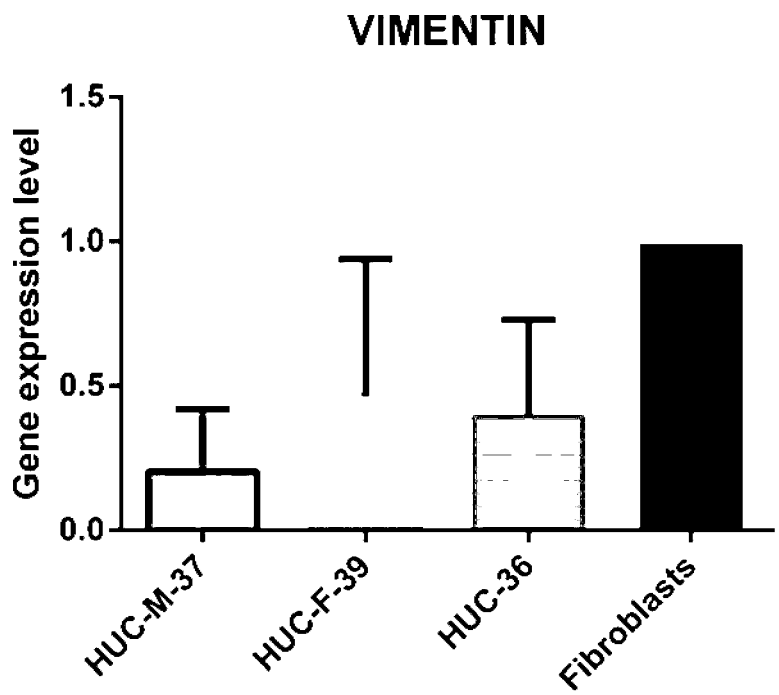

Only one urine cell line expressed epithelial marker KRT7 (FIG. 16A), whereas all three urine cell lines expressed epithelial marker Occludin (OCL; FIG. 16B). All of the urine cell lines express renal tubular markers NR3C2 (FIG. 16C) and L1CAM (FIG. 16D), and variable levels of the renal tubular marker SLC2A1 (FIG. 16E). All the urine cell lines expressed low levels of the fibroblast marker VIMENTIN (FIG. 16F). This indicates that there is variation in urine cells obtained from different individuals, and also indicates that the urine cells are of mixed origin.

In conclusion, the protocols described herein are able to, in embodiments, transdifferentiate cells, from urine derived cells to induced definitive endoderm cells using the primary induction protocol, to induced pancreatic precursors using the secondary protocols and induced beta cells using the tertiary protocols described herein.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

REFERENCES

Borowiak M et al., *Cell Stem Cell* 4(4):348-358 (2009).
D'Amour K A et al., *Nat Biotechnol* 24:1392-1401 (2006).
Davis R L et al., *Cell* 51 (6): 987-1000 (1987)
Efe, J A et a. *Nature Cell Biology* 13 (3): 215-222 (2011)
Hori Y et al., *PloS Medicine* 2:e103 (2005).
Huangfu D et al., *Nat Biotechnol* 26:795-797 (2008).
Kuwabara T et al., *EMBO Molecular Medicine* 3:742-754 (2011).
Li W. et al., *Cell Stem Cell* 4:16-19 (2009)
Li K et al., *Cell Stem Cell* 14: 228 (2014)
Maherali, N & Hochedlinger, K, *Curr Biol* 19:1718-1723 (2009).
Pagliuca F W et al., *Cell* 159:428-439 (2014).
Pasca di Magliano, M & Hebrok, M, *Nat Rev Cancer* 3: 903-911 (2003).

Pennarossa G et al., *Proc Natl Acad Sci USA* 110:8948-8953 (2013).
Shi Y, *Nat Rev Genet* 8:829-833 (2007)
Shi Y et al., *Cell Stem Cell* 2:525-528 (2008).
Szabat M et al *Endocrinol* 150:1627-1635. (2009)

Tojo M et al., *Cancer Sci* 96:791-800 (2005).
Vierbuchen T et al., *Nature* 463 (7284): 1035-1041 (2010).
Wild S et al., *Diabetes Care* 27:1047-1053 (2004).
Zhou Q et al., *Nature* 455 (7213): 627-632 (2008).

The invention claimed is:

1. A method of producing induced beta cells from urine-derived cells, the method comprising:
   (a) providing urine-derived cells; wherein the urine-derived cells express human nuclear antigen, CD13, vimentin and E-cadherin
   (b) inducing the urine-derived cells provided in step (a) to obtain induced endoderm cells by an induction process consisting of culturing said urine-derived cells in a primary induction culture medium comprising an effective amount of a combination of small molecule reprogramming factor(s) comprising a definitive endoderm inducer, a glycogen synthase kinase 3 (GSK3) inhibitor and Vitamin C for a first period of time;
   (c) inducing the induced endoderm cells obtained in step (b) by culturing said induced endoderm cells in a secondary induction culture medium comprising an effective amount of at least one small molecule reprogramming factor(s) selected from the group consisting of a PKC activator, a sonic hedgehog (SSH) inhibitor, a retinoic acid receptor (RAR) agonist, Vitamin C, an activin receptor-like kinase (ALK) receptor inhibitor, a Pdx1 inducer and a bone morphogenetic protein (BMP) inhibitor for a second period of time to obtain induced pancreatic precursor cells; and
   (d) inducing the induced pancreatic precursor cells obtained in step (c) by culturing said pancreatic precursor cells in a tertiary induction culture medium comprising an effective amount of at least one small molecule reprogramming factor(s) selected from the group consisting of a mitogen-activated protein kinase kinase (MEK) inhibitor, Vitamin C, a notch inhibitor, an ALK receptor inhibitor, triiodothyronine, an RAR agonist, and a SSH inhibitor for a third period of time to obtain induced beta cells; and
wherein the method excludes the use of reprogramming factors that are not small molecules.

2. The method of claim 1, wherein the second period of time consists of a first portion and a second portion, and wherein the secondary induction medium comprises an effective amount of at least one small molecule reprogramming factor(s) selected from the group consisting of:
   a PKC activator, a sonic hedgehog (SSH) inhibitor, a retinoic acid receptor (RAR) agonist, Vitamin C, an activin receptor-like kinase (ALK) receptor inhibitor, and a Pdx1 inducer for a first portion of the second period of time; and
   a PKC activator, a sonic hedgehog (SSH) inhibitor, Vitamin C, an activin receptor-like kinase (ALK) receptor inhibitor, and a Pdx1 inducer for a second portion of the second period of time.

3. The method of claim 1, wherein the second period of time consists of a first portion, a second portion and a third portion, and wherein the secondary induction medium comprises an effective amount of at least one small molecule reprogramming factor(s) selected from the group consisting of:
Vitamin C for the first portion of the second period of time;
Vitamin C, a RAR agonist, a SSH inhibitor, a PKC activator and a BMP inhibitor for a second portion of the second period of time; and
Vitamin C, a RAR agonist, and a SSH inhibitor for a third portion of the second period of time.

4. The method of claim 1, wherein the tertiary induction medium comprises an effective amount of a combination of small molecule reprogramming factor(s) comprising the MEK inhibitor, Vitamin C, and the notch inhibitor.

5. The method of claim 1, wherein the third period of time consists of a first portion, a second portion and a third portion, and wherein the tertiary induction medium comprises an effective amount of at least one small molecule reprogramming factor(s) selected from the group consisting of:
Vitamin C, a RAR agonist, a SSH inhibitor, a notch inhibitor, an ALK receptor inhibitor, and triiodothyronine for the first portion of the third period of time,
Vitamin C, a RAR agonist, a notch inhibitor, an ALK receptor inhibitor, and triiodothyronine for the second portion of the third period of time, and
Vitamin C and triiodothyronine for the third portion of the third period of time.

6. The method of claim 1, wherein:
the primary induction medium comprises an effective amount of IDE1, lithium chloride and Vitamin C;
the secondary induction medium comprises an effective amount of
Indolactam V, cyclopamine-KAAD, Vitamin C, retinoic acid, A83-01 and BRD 7552 for a first portion of the second period of time, and
Indolactam V, cyclopamine-KAAD, Vitamin C, A83-01 and BRD 7552 for a second portion of the second period of time; and
the tertiary induction medium comprises an effective amount of SB203580, Vitamin C and DAPT.

7. The method of claim 1, wherein:
the primary induction medium comprises an effective amount of IDE1, lithium chloride and Vitamin C;
the secondary induction medium comprises an effective amount of
Vitamin C for a first portion of the second period of time;
Vitamin C, RA, cyclopamine-KAAD, Indolactam V and dorsomorphin for a second portion of the second period of time; and
Vitamin C, RA, and cyclopamine-KAAD for a third portion of the second period of time; and
the tertiary induction medium comprises an effective amount of
Vitamin C, RA, cyclopamine-KAAD, DAPT, A83-01, and triiodothyronine for a first portion of the third period of time,
Vitamin C, RA, DAPT, A83-01, and triiodothyronine for a second portion of the third period of time, and
Vitamin C and triiodothyronine for a third portion of the third period of time.

8. A method of producing induced endoderm cells from urine-derived cells, the method comprising:
(a) providing urine-derived cells; wherein the urine-derived cells express human nuclear antigen, CD13, vimentin and E-cadherin and
(b) inducing the urine-derived cells provided in step (a) to obtain induced endoderm cells by an induction process consisting of culturing said urine-derived cells in a primary induction culture medium comprising an effective amount of a combination of small molecule reprogramming factor(s) comprising a definitive endoderm inducer, a glycogen synthase kinase 3 (GSK3) inhibitor and Vitamin C for a first period of time; and
wherein the method excludes the use of reprogramming factors that are not small molecules.

9. A method of producing induced pancreatic precursor cells from urine-derived cells, the method comprising:
(a) providing urine-derived cells; wherein the urine-derived cells express human nuclear antigen, CD13, vimentin and E-cadherin
(b) inducing the urine-derived cells provided in step (a) to obtain induced endoderm cells by an induction process consisting of culturing said urine-derived cells in a primary induction culture medium comprising an effective amount of a combination of small molecule reprogramming factor(s) comprising a definitive endoderm inducer, a glycogen synthase kinase 3 (GSK3) inhibitor and Vitamin C for a first period of time to obtain induced endoderm cells; and
(c) inducing the induced endoderm cells obtained in step (b) by culturing said induced endoderm cells in a secondary induction culture medium comprising an effective amount of at least one small molecule reprogramming factor(s) selected from the group consisting of a PKC activator, a sonic hedgehog (SSH) inhibitor, a retinoic acid receptor (RAR) agonist, Vitamin C, an activin receptor-like kinase (ALK) receptor inhibitor, a Pdx1 inducer and a bone morphogenetic protein (BMP) inhibitor for a second period of time to obtain induced pancreatic precursor cells; and
wherein the method excludes the use of reprogramming factors that are not small molecules.

10. The method of claim 1, wherein the urine-derived cells are obtained from a urine sample of a subject.

11. The method of claim 1, wherein step (a) further comprises expanding the urine-derived cells by culturing the urine-derived cells in an appropriate tissue culture medium.

* * * * *